(12) United States Patent
Aizenberg et al.

(10) Patent No.: US 9,932,484 B2
(45) Date of Patent: Apr. 3, 2018

(54) SLIPPERY LIQUID-INFUSED POROUS SURFACES AND BIOLOGICAL APPLICATIONS THEREOF

(75) Inventors: Joanna Aizenberg, Boston, MA (US); Benjamin Hatton, Cambridge, MA (US); Donald Ingber, Boston, MA (US); Michael Super, Lexington, MA (US); Tak Sing Wong, Allston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 282 days.

(21) Appl. No.: 13/980,858

(22) PCT Filed: Jan. 19, 2012

(86) PCT No.: PCT/US2012/021929
§ 371 (c)(1),
(2), (4) Date: Feb. 28, 2014

(87) PCT Pub. No.: WO2012/100100
PCT Pub. Date: Jul. 26, 2012

(65) Prior Publication Data
US 2014/0187666 A1    Jul. 3, 2014

Related U.S. Application Data

(60) Provisional application No. 61/434,217, filed on Jan. 19, 2011, provisional application No. 61/466,352, (Continued)

(51) Int. Cl.
*C09D 5/16* (2006.01)
*A61L 15/24* (2006.01)
(Continued)

(52) U.S. Cl.
CPC ............ *C09D 5/1693* (2013.01); *A61L 15/24* (2013.01); *A61L 15/34* (2013.01); *A61L 15/42* (2013.01);
(Continued)

(58) Field of Classification Search
CPC .................................................... C09D 5/1693
See application file for complete search history.

(56) References Cited

U.S. PATENT DOCUMENTS 3,068,187 A    12/1962   Bolstad et al.
3,274,007 A     9/1966   Jones
(Continued)

FOREIGN PATENT DOCUMENTS

CN    1360618 A    7/2002
CN    1884398 A    12/2006
(Continued)

OTHER PUBLICATIONS

Afessa, B. et al., "Association Between a Silver-Coated Endotracheal Tube and Reduced Mortality in Patients With Ventilator-Associated Pneumonia," Chest, vol. 137, pp. 1015-1021 (May 2010).

(Continued)

*Primary Examiner* — Michael Pepitone
(74) *Attorney, Agent, or Firm* — Wilmer Cutler Pickering Hale and Dorr LLP

(57) ABSTRACT

A self-healing, scratch resistant slippery surface that is manufactured by wicking a chemically-inert, high-density liquid coating over a roughened solid surface featuring micro and nanoscale topographies is described. Such a slippery surface shows anti-wetting properties, as well as exhibits significant reduction of adhesion of a broad range of biological materials, including particles in suspension or solution. Specifically, the slippery surfaces can be applied to (Continued)

medical devices and equipment to effectively repel biological materials such as blood, and prevent, reduce, or delay coagulation and surface-mediated clot formation. Moreover, the slippery surfaces can be used to prevent fouling by microorganisms such as bacteria.

27 Claims, 53 Drawing Sheets

Related U.S. Application Data filed on Mar. 22, 2011, provisional application No. 61/470,973, filed on Apr. 1, 2011, provisional application No. 61/496,883, filed on Jun. 14, 2011, provisional application No. 61/509,488, filed on Jul. 19, 2011, provisional application No. 61/529,734, filed on Aug. 31, 2011, provisional application No. 61/538,100, filed on Sep. 22, 2011.

(51) Int. Cl.

| | | |
|---|---|---|
| A61L 15/34 | (2006.01) | |
| A61L 15/42 | (2006.01) | |
| A61L 15/46 | (2006.01) | |
| A61L 27/28 | (2006.01) | |
| A61L 27/34 | (2006.01) | |
| A61L 27/50 | (2006.01) | |
| A61L 33/00 | (2006.01) | |
| A61L 33/06 | (2006.01) | |
| F15D 1/02 | (2006.01) | |
| F15D 1/10 | (2006.01) | |
| B05D 5/08 | (2006.01) | |

(52) U.S. Cl.
CPC ............. *A61L 15/46* (2013.01); *A61L 27/28* (2013.01); *A61L 27/34* (2013.01); *A61L 27/50* (2013.01); *A61L 33/0094* (2013.01); *A61L 33/064* (2013.01); *C09D 5/1656* (2013.01); *C09D 5/1681* (2013.01); *F15D 1/02* (2013.01); *F15D 1/10* (2013.01); *A61L 2400/12* (2013.01); *B05D 5/083* (2013.01)

(56) References Cited

U.S. PATENT DOCUMENTS

| | | | |
|---|---|---|---|
| 4,386,170 A | 5/1983 | Monroe | |
| 4,633,004 A | 12/1986 | Boutevin et al. | |
| 4,787,991 A | 11/1988 | Morozumi et al. | |
| 4,937,596 A | 6/1990 | Schmid | |
| 5,358,719 A | 10/1994 | Mellul et al. | |
| 5,372,888 A | 12/1994 | Ogawa et al. | |
| 5,602,214 A | 2/1997 | Lin et al. | |
| 5,620,778 A | 4/1997 | Clatworthy | |
| 5,624,713 A | 4/1997 | Ramer | |
| 5,630,846 A | 5/1997 | Hara et al. | |
| 5,798,409 A | 8/1998 | Ho | |
| 5,804,318 A | 9/1998 | Pinchuk et al. | |
| 6,071,981 A | 6/2000 | Johnson et al. | |
| 6,232,379 B1 | 5/2001 | Takita | |
| 6,247,603 B1 | 6/2001 | Farrell et al. | |
| 6,511,753 B1 | 1/2003 | Teranishi et al. | |
| 7,189,934 B2 | 3/2007 | Youngner | |
| 7,192,993 B1 | 3/2007 | Sarangapani et al. | |
| 7,560,492 B1 | 7/2009 | Claude et al. | |
| 7,666,514 B2 | 2/2010 | Sakamoto et al. | |
| 7,723,405 B2 | 5/2010 | Braun et al. | |
| 7,811,666 B2 | 10/2010 | Dry | |
| 2001/0014711 A1 | 8/2001 | Levy | |
| 2003/0212232 A1 | 11/2003 | Majeti et al. | |
| 2004/0034941 A1 | 2/2004 | Iwato et al. | |
| 2004/0186211 A1* | 9/2004 | Howell | C10M 107/38 524/404 |
| 2005/0164008 A1 | 7/2005 | Rukavina | |
| 2006/0024504 A1 | 2/2006 | Nelson et al. | |
| 2006/0153993 A1 | 7/2006 | Schmidt et al. | |
| 2006/0159645 A1 | 7/2006 | Miller et al. | |
| 2007/0039832 A1 | 2/2007 | Heikenfeld | |
| 2007/0141306 A1 | 6/2007 | Kasai et al. | |
| 2007/0166344 A1 | 7/2007 | Qu et al. | |
| 2007/0184733 A1 | 8/2007 | Manley | |
| 2007/0224391 A1 | 9/2007 | Krupenkin et al. | |
| 2007/0254000 A1 | 11/2007 | Guo et al. | |
| 2008/0195170 A1 | 8/2008 | Asgari | |
| 2009/0078153 A1 | 3/2009 | Shchukin et al. | |
| 2009/0098299 A1 | 4/2009 | Cheng | |
| 2009/0209922 A1 | 8/2009 | Boisjoly | |
| 2010/0009583 A1 | 1/2010 | Bringley et al. | |
| 2010/0021748 A1 | 1/2010 | Hu et al. | |
| 2010/0210745 A1 | 8/2010 | McDaniel et al. | |
| 2011/0165206 A1 | 7/2011 | Liu et al. | |
| 2011/0283778 A1 | 11/2011 | Angelescu et al. | |
| 2011/0287987 A1* | 11/2011 | Mordukhovich | C10M 171/00 508/103 |
| 2012/0052241 A1 | 3/2012 | King et al. | |
| 2012/0141052 A1 | 6/2012 | Drew et al. | |
| 2013/0032316 A1 | 2/2013 | Dhiman et al. | |

FOREIGN PATENT DOCUMENTS

| | | |
|---|---|---|
| CN | 101052667 A | 10/2007 |
| CN | 101198542 A | 6/2008 |
| CN | 101374607 A | 2/2009 |
| CN | 101444777 A | 6/2009 |
| CN | 101538395 A | 9/2009 |
| CN | 101580753 A | 11/2009 |
| CN | 101675156 A | 3/2010 |
| CN | 101918621 A | 12/2010 |
| CN | 102388180 A | 3/2012 |
| DE | 19818956 A1 | 11/1998 |
| EP | 0166998 A2 | 1/1986 |
| EP | 0338418 A1 | 10/1989 |
| EP | 0497204 A2 | 8/1992 |
| EP | 0893164 A2 | 1/1999 |
| EP | 1002825 A2 | 5/2000 |
| EP | 1487590 A2 | 12/2004 |
| EP | 1487590 B1 | 12/2004 |
| EP | 2228053 A1 | 9/2010 |
| EP | 2363438 A1 | 9/2011 |
| JP | S60-259269 A | 12/1985 |
| JP | 62-063219 A | 3/1987 |
| JP | S62-252477 A | 11/1987 |
| JP | 1-170932 A | 7/1989 |
| JP | 04-270649 A | 9/1992 |
| JP | 05-229402 A | 9/1993 |
| JP | 5240251 B2 | 9/1993 |
| JP | H06-48685 U | 7/1994 |
| JP | 07-242769 A | 9/1995 |
| JP | H08-12816 A | 1/1996 |
| JP | 2000-510353 A | 8/2000 |
| JP | 2003-170540 A | 6/2003 |
| JP | 2004-037764 A | 2/2004 |
| JP | 2005-082848 A | 3/2005 |
| JP | 2005-231084 A | 9/2005 |
| JP | 2006-280843 A | 10/2006 |
| JP | 2008-223003 A | 9/2008 |
| JP | 2009-523890 A | 6/2009 |
| JP | 2010-047890 A | 3/2010 |
| WO | WO-92/10532 A1 | 6/1992 |
| WO | WO-93/17077 A1 | 9/1993 |
| WO | WO-99/36490 A1 | 7/1999 |
| WO | WO-01/78800 A1 | 10/2001 |
| WO | WO-02/09647 A2 | 2/2002 |
| WO | WO-03013827 A1 | 2/2003 |
| WO | WO-2005091309 A1 | 9/2005 |
| WO | WO-2005/121288 A1 | 12/2005 |
| WO | WO-2006091235 A1 | 8/2006 |
| WO | WO-2006/118460 A1 | 11/2006 |
| WO | WO-2007/130734 A2 | 11/2007 |
| WO | WO-2008/013825 A2 | 1/2008 |

(56) References Cited

FOREIGN PATENT DOCUMENTS

| WO | WO-2010028752 A1 | 3/2010 | | |
|---|---|---|---|---|
| WO | WO-2010/042804 A2 | 4/2010 | | |
| WO | WO-2010/065960 A2 | 6/2010 | | |
| WO | WO-2010116045 A1 | 10/2010 | | |
| WO | WO-2011005200 A1 | 1/2011 | | |
| WO | WO 2011005200 A1 * | 1/2011 | ......... | A61B 17/8802 |
| WO | WO-2011/049896 A2 | 4/2011 | | |
| WO | WO-2012/055821 A1 | 5/2012 | | |
| WO | WO-2012/055825 A1 | 5/2012 | | |
| WO | WO-2012/100099 A2 | 7/2012 | | |
| WO | WO-2012/100100 A2 | 7/2012 | | |
| WO | WO-2013/022467 A2 | 2/2013 | | |
| WO | WO-2013/106588 A1 | 7/2013 | | |
| WO | WO-2013/115868 A2 | 8/2013 | | |

OTHER PUBLICATIONS

Ahuja, A. et al., "Nanonails: A Simple Geometrical Approach to Electrically Tunable Superlyophobic Surfaces," Langmuir, vol. 24, pp. 9-14 (No Month Listed 2008).
Badrossamay, Mohammad Reza, et al., "Nanofiber Assembly by Rotary Jet-Spinning," Nano Letters, vol. 10, No. 6, pp. 2257-2261, 11 pages (Jun. 9, 2010).
Bai, Joseph R. et al., "Core-Annular Flows," Annual Review Fluid Mechanics, vol. 29, pp. 65-90 (Jan. 1997).
Banerjee, I. et al., "Antifouling coatings: recent developments in the design of surfaces that prevent fouling by proteins, bacteria, and marine organisms," Advanced Materials, pp. 690-718 (No Month Listed 2011).
Banerjee, S. et al., "Infection control during GI endoscopy," Gastrointest Endosc, vol. 67, pp. 781-790 (May 2008).
Banhart, John, "Manufacture, characterisation and application of cellular metals and metal forms," Progress in Materials Science, vol. 46, pp. 559-632 (No Month Listed 2001).
Barstad, R. M. et al., "Monocyte procoagulant activity induced by adherence to an artificial surface is reduced by end-point immobilized heparin-coating of the surface", Thrombosis and haemostatis, vol. 79, pp. 302-305, Downloaded from www.thrombosis-online.com on (Mar. 17, 2014).
Barthlott, W. & Neinhuis, C., "Purity of the sacred lotus, or escape from contamination in biological surfaces," Planta, vol. 202, pp. 1-8 (Apr. 1997).
Beilenhoff, U. et al., "ESGE-ESGENA guideline: Cleaning and disinfection in gastrointestinal endoscopy Update 2008," Endoscopy, vol. 40, pp. 939-957 (Sep. 23, 2008).
Bhardwaj, U. et al., "A review of the development of a vehicle for localized and controlled drug delivery for implantable biosensors," J. Diabetes Sci Technol., vol. 2, pp. 1016-1029 (Nov. 2008).
Bocquet, L. & Lauga, E., "A smooth future?," Nature Mater, vol. 10, pp. 334-337 (May 2011).
Bos, R. et al., "Retention of bacteria on a substratum surface with micro patterned hydrophobicity," Fems Microbiology Letters, vol. 189, No. 2, pp. 311-315 (Aug. 15, 2000).
Chaudhury, Manoj K. and Whitesides, George M., Direct Measurement of Interfacial Interactions between Semispherical Lenses and Flat Sheets of Poly (dimethysiloxane) and Their Chemical Derivatives, Langmuir, vol. 7, pp. 1013-1025 (No Month Listed 1991).
Chen, S. et al., "Surface hydration: Principles and applications toward low-fouling/nonfouling biomaterials," Polymer, vol. 51, pp. 5283-5293 (Aug. 10, 2010).
Clark, Jr., Leland C. and Gollan, Frank, "Survival of Mammals Breathing Organic Liquid Equilibriated With Oxygen at Atmospheric Pressure", Science, vol. 152, pp. 1755-1756 (Jun. 24, 1966).
Costerton, J. et al., "Bacterial biofilms: a common cause of persistent infections," Science, vol. 284, No. 5418, pp. 1318-1322 (May 21, 1999).
Costerton, J.W. et al., "Bacterial biofilms in nature and disease," Ann. Rev. Microbiol, vol. 41, pp. 435-464 (No Month Listed 1987).

Cribier, A. et al., "Percutaneous transcatheter implantation of an aortic valve prothesis for calcific aortic stenosis—First human case description," Circulation, vol. 106, pp. 3006-3008 (Nov. 25, 2002).
Crnich, C.J. & G. Maki, D.G., "The Promise of Novel Technology for the Prevention of Intravascular Device-Related Bloodstream Infection. I. Pathogenesis and Short-Term Devices," Clinical Infectious Diseases, vol. 34, pp. 1232-1242 (May 1, 2002).
De Beer, D. & Stoodley, P., "Microbial Biofilms," Prokaryotes, vol. 1, pp. 904-937 (No Month Listed 2006).
de Gennes, P.-G. Et al., "Capillarity and Wetting Phenomena: drops, bubbles, pearls, waves," Springer, New York, 151 pages ( No Month Listed 2004).
Dieter, R.S., "Coronary artery stent infection," Clin. Cardiol., vol. 23, pp. 808-810 (Jan. 6, 2000).
Dismukes et al., "Prosthetic valve endocarditis. Analysis of 38 cases," Circulation, vol. 48, pp. 365-377 (Aug. 1973).
Drelich, et al., "Measurement of Interfacial Tension in Fluid-Fluid Systems", Encyclopedia of Surface and Colloid Science, pp. 3152-3166 (Jan. 2002).
Fowkes, F.M. , "Attractive forces at interfaces," Ind. Eng. Chem., vol. 56, pp. 40-52 (Dec. 1964).
Fuerstman, et al., "Coding/Decoding and Reversibility of droplet trains in Microfluidic networks," Science, vol. 315, No. 5813, pp. 828-832 (Feb. 9, 2007).
Gao, L. and McCarthy, T.J., "Teflon is Hydrophobic Comments on Definitions of Hydrophobic, Shear versus Tensile Hydrophobicity, and Wettability Characterization," Langmuir, vol. 24, pp. 9183-9188 (Sep. 2, 2008).
Garg, N. et al., "Acute Coronary Syndrome Caused by Coronary Artery Mycotic Aneurysm Due to Late Stent Infection Localized With Radiolabeled Autologous Leukocyte Imaging," Clin. Nucl. Med., vol. 34, pp. 753-755 (Nov. 2009).
George, P.A. et al., Self-assembling polystyrene-block poly(ethylene oxide) copolymer surface coatings: resistance to protein and cell adhesion, Biomaterials, vol. 30 pp. 2449-2456 (May 2009).
Gristina, A.G. Et al., "Biomaterial-centered sepsis and the total artifical heart. Microbial adhesion vs tissue integration," JAMA, vol. 259, pp. 870-874 (Feb. 1988).
Hall-Stoodley, L. et al., Bacterial biofilms: from the natural environment to infectious diseases, Nature Reviews Microbiology, vol. 2, No. 2, pp. 95-108 (Feb. 2004).
Hatton, et al., "Assembly of large-area, highly ordered, crack-free inverse opal films," Proceedings of the National Academy of Science of the United States of America, vol. 107, No. 23, pp. 10354-10359 (Jun. 8, 2010).
Hearn, A.T. et al., "Endovascular stent infection with delayed bacterial challenge," American Journal of Surgery, vol. 174, pp. 157-159 (Aug. 1997).
Inazaki, S. et al., Surface modification of poly (tetrafluoroethylene) with ArF excimer laser irradiation, J. Photopoly. Sci. Technol. vol. 7, No. 2, pp. 389-395 (1994).
International Search Report and Written Opinion Issued by the U.S. Patent and Trademark Office as International Searching Authority for International Application No. PCT/US09/48880 dated Nov. 17, 2009 (14 pgs.).
International Search Report and Written Opinion Issued by the U.S. Patent and Trademark Office as International Searching Authority for International Application No. PCT/US11/44553 dated Oct. 31, 2011 (12 pgs.).
Israelachvili, Jacob N., "Intermolecular and Surface Forces—Third Edition," Academic Press, 706 pages (No Month Listed 2011).
Karchmer, A.W. et al., "*Staphylococcus epidermidis* causing prosthetic valve endocarditis: microbiologic and clinical observations as guides to therapy," Ann Intern Med, vol. 98, pp. 447-455 (Apr. 1, 1983).
Kim, et al., "Structural Transformation by Electrodeposition on Patterned Substrates (STEPS): A new Versatile Nano-fabrication Method," Nano Letters, vol. 12, No. 2, pp. A-G (Mar. 2011).
Kobayashi, H. and Owen, M.J., "Surface tension of poly[(3,3,4,4,5,5,6,6-nanoflur-ohexyl methlisiloxane]," Macromolecules, vol. 23, No. 23, pp. 4929-4933 (No Month Listed 1990).

(56) References Cited

OTHER PUBLICATIONS

Koschwanez, H.E. et al., "In vitro and in vivo characterization of porous poly-L-lactic acid coatings for subcutaneously implanted glucose sensors," Journal of Biomedical Materials Research Part A, pp. 792-807 (Dec. 2008).
Lee, Woo, et al., "Fast fabrication of long-range ordered porous alumina membranes by hard anodization," Nature Mater, vol. 5, pp. 741-747 (Sep. 2006).
Li, Yang, et al., "Bioinspired Self-Healing Superhydrophobic Coatings," Angewandte Chemie, vol. 49, No. 35, pp. 6129-6133 (Aug. 16, 2010).
Lillehoj, et al., "A self-pumping lab-on-a-chip for rapid detection of botulinium toxin," Lab Chips, vol. 10, pp. 2265-2270 (Jun. 11, 2010).
Lin, T-K, et al., "Surface modification of polytetrafluoroethylene films by plasma pretreatment and graft copolymierization to improve their adhesion to bismaleimide," Polym. Int., vol. 58, No. 1, pp. 46-53 (Jan. 2009).
Matsunaga, Mariko, et al., "Controlling the Stability and Reversibility of Micropillar Assembly by Surface Chemistry," J. Am. Chem. Soc., vol. 133, No. 14, pp. 5545-5553, 4 pages (Dec. 2, 2011).
Meuler, Adam J. et al., Relationships between Water Wettability and Ice Adhesion, ACS Applied Materials and Interfaces, vol. 2, No. 11, 31 pages (Oct. 15, 2010).
Munro, W.A. et al., "Deterioration of pH electrode response due to biofilm formation on the glass membrane," Sensor Actuat B-Chem, vol. 37, pp. 187-194 (Dec. 1996).
Niimi, Y. et al., "The effects of heparin coating of oxygenator fibers on platelet adhesion and protein adsorption," Anesth. Analg., vol. 89, pp. 573-579 (May 12, 1999).
Noetzel, M.J. & Baker, R.P., "Shunt fluid examination: risks and benefits in the evaluation of shunt malfunction and infection," J. Neurosurg., vol. 61, pp. 328-332 (Aug. 1984).
O'Toole, G. Et al., "Biofilm Formation as Microbial Development," Annu. Rev. Microbiol., vol. 54, pp. 49-79, 35 pages (No Month Listed 2000).
Park, K.D. et al., "Bacterial adhesion on PEG modified polyurethane surfaces," Biomaterials, vol. 19, No. 7-9, pp. 851-859 (Apr.-May 1998).
Poetes, et al., "Metastable Underwater Superhydrophobicity," Physical Review Letters, vol. 105, Issue 16, pp. 166104.1-166104.4 Published (Oct. 14, 2010).
Pokroy, B. et al., "Fabrication of Bio-Inspired Actuated Nanostructures with Arbitrary Geometry and Stiffness," Adv. Mater, vol. 21, pp. 463-469 (Jan. 26, 2009).
Prakash and Gershenfeld, "Microfluidic Bubble Logic," Science, vol. 315, No. 5813, 176 pages (Sep. 2008).
Prime, K.L. & Whitesides, G.M., "Self-assembled organic monolayers: model systems for studying adsorption of proteins at surfaces," Science, vol. 252, No. 5009, p. 1164-1167 (May 24, 1991).
Quere, D., "Wetting and roughness," Annu. Rev. Mater. Res., vol. 38, pp. 71-99 (Apr. 7, 2008).
Rothemund, Paul W.K., "Folding DNA to create nanoscale shapes and patterns," Nature, vol. 440, 82 pages (Mar. 16, 2006).
Shaffer, T.H. et al., "State of art review: liquid ventilation," Pediatric Pulmonology, vol. 14, pp. 102-109 (Oct. 1992).
Shafrin, E.G. & Zisman, W.A., "Constitutive relations in the wetting of low energy surfaces and the theory of the retraction method of preparing monolayers," J. Phys. Chem., vol. 64, pp. 519-524 (May 1960).
Skattum, L. et al., "Complement deficiency states and associated infections," Mol. Immunol., vol. 48, No. 14, pp. 1643-1655 (Aug. 2011).
Sohail, M.R. et al., "Risk factor analysis of permanent pacemaker infection," Clin Infect Dis, vol. 45, pp. 166-173 (Jul. 15, 2007).
Trevors, J., "Silver resistance and accumulation in bacteria," Enzyme and Mircobial Technology, vol. 9, No. 6, pp. 331-333 (Jun. 1987).
Tuli, S. et al., "Risk factors for repeated cerebrospinal shunt failures in pediatric patients with hydrocephalus," J. Neurosurg., vol. 92, pp. 31-38 (Jan. 2000).
Tuteja, Anish, et al., "Designing Superoleophobic Surfaces," Science, vol. 318, No. 5856, pp. 1618-1622 (Dec. 7, 2007) www.sciencemag.org.
Tuteja, Anish, et al., "Robust omniphobic surfaces," PNAS, vol. 105, No. 47, pp. 18200-18205 (Nov. 25, 2008).
Varanasi, Kripa K. et al., Frost formation and ice adhesion on superhydrophobic surfaces, Applied Physics Letters, vol. 97, pp. 234102-1-234102-3 (No Month Listed 2010).
Voskerician, G. Et al., "Biocompatibility and biofouling of MEMS drug delivery devices," Biomaterials, vol. 24, pp. 1959-1967 (2003).
Williams, Kirt R., et al., "Etch Rates for Micromachining Processing—Part II," Journal of Microelectromechanical Systems, vol. 12, No. 6, pp. 761-778 (Dec. 2003).
Wilson, G.S. & Gifford, R., "Biosensors for real-time in vivo measurements," Biosens. Bioelectron, vol. 20, pp. 2388-2403 (Jan. 15, 2005).
Wong, P.K. et al., "Deformation of DNA Molecules by Hydrodynamic Focusing," Journal of Fluid Mechanics, vol. 497, pp. 55-65 (No Month Listed 2003).
Wong, Pak Kin, et al., "Closed-loop control of cellular functions using combinatory drugs guided by a stochastic search algorithm," Proceedings of National Academy of Science for the United States of America, vol. 105, No. 13, pp. 5105-5110 (Apr. 1, 2008).
Xu, Q. et al., "Approaching Zero: Using Fractured Crystals in Metrology for Replica Molding," J. Am. Chem. Soc., vol. 127, No. 3, pp. 854-855 (No Month Listed 2005).
Zhao, L. et al., "Antibacterial coatings on titanium implants," Journal of Biomedical Materials Research Part B: Applied Biomaterials, vol. 91, No. 1, pp. 470-480 (No Month Listed 2009).
Bico, J. et al., "Rough wetting," Europhysics Letters, vol. 55, No. 2, pp. 214-220 (Jul. 15, 2001).
Bico, J. et al., "Wetting of textured surfaces," Colloids and Surfaces, A: Physicochemical and Engineering Aspects, vol. 206, pp. 41-46 (No Month Listed 2002).
Ahuja, A. et al., "Nanonails: A Simple Geometrical Approach to Electrically Tunable Superlyophobic Surfaces," Langmuir, vol. 24, pp. 9-14 (2008).
Banerjee, I. et al., "Antifouling coatings: recent developments in the design of surfaces that prevent fouling by proteins, bacteria, and marine organisms," Advanced Materials, pp. 690-718 (2011).
Banerjee, S. et al., "Infection control during GI endoscopy," Gastrointest. Endosc., vol. 67, pp. 781-790 (May 2008).
Banhart, John, "Manufacture, characterisation and application of cellular metals and metal foams," Progress in Materials Science, vol. 46, pp. 559-632 (2001).
Berger, R. G., "Flavours and Fragrances: Chemistry, Bioprocessing and Sustainability," Springer, 15 pages—Title Page, Copyright Page and Table of Contents Only (2007).
Bhardwaj, U. et al., "A review of the development of a vehicle for localized and controlled drug delivery for implantable biosensors," J. Diabetes Sci. Technol., vol. 2, pp. 1016-1029 (Nov. 2008).
Bocquet, L. & Lauga, E., "A smooth future?," Nature Mater., vol. 10, pp. 334-337 (May 2011).
Bohn, et al., "Insect Aquaplaning: Nepenthes Pitcher Plants Capture Prey with the Peristome, a Fully Wettable Water-Lubricated Anisotropic Surface", PNAS, 101(39):14138-14143, Sep. 28, 2004, 6 pages.
Bos, R. et al., "Retention of bacteria on a substratum surface with micro-patterned hydrophobicity," FEMS Microbiology Letters, vol. 189, No. 2, pp. 311-315 (Aug. 15, 2000).
Cassie, A.B.D. & Baxter, S., "Large contact angles of plant and animal surfaces," Nature, vol. 155, pp. 21-22 (Jan. 6, 1945).
Chaudhury, Manoj K. and Whitesides, George M., "Direct Measurement of Interfacial Interactions between Semispherical Lenses and Flat Sheets of Poly(dimethylsiloxane) and Their Chemical Derivatives," Langmuir, vol. 7, pp. 1013-1025 (1991).
Clark, Jr., Leland C. and Gollan, Frank, "Survival of Mammals Breathing Organic Liquid Equilibrated With Oxygen at Atmospheric Pressure", Science, vol. 152, pp. 1755-1756 (Jun. 24, 1966).

(56) References Cited

OTHER PUBLICATIONS

Costerton, J.W. et al., "Bacterial biofilms in nature and disease," Ann. Rev. Microbiol., vol. 41, pp. 435-464 (1987).
Cribier, A. et al., "Percutaneous Transcatheter Implantation of an Aortic Valve Prosthesis for Calcific Aortic Stenosis," Circulation, vol. 106, pp. 3006-3008 (Nov. 25, 2002).
Database WPI Weekly 198933, Thomson Scientific, London, GB, AN 1989-237086, XP002694116 & JP1170932A (Nippon Sheet Glass Co. Ltd.) 1 page (Jul. 6, 1989) (abstract).
De Beer, D. & Stoodley, P., "Microbial Biofilms," Prokaryotes, vol. 1, pp. 904-937 (2006).
de Gennes, P.G. et al., "Capillarity and Wetting Phenomena: drops, bubbles, pearls, waves," Springer, New York, 151 pages (2004).
Dismukes et al., "Prosthetic valve endocarditis: Analysis of 38 cases," Circulation, vol. 48, pp. 365-377 (Aug. 1973).
Fadeev, A. Y. and McCarthy, T. J., "Surface Modification of Poly(ethylene terephthalate) to Prepare Surfaces with Silica-Like Reactivity," Langmuir, vol. 14, No. 19, pp. 5586-5593 (1998).
Fowkes, F.M., "Attractive forces at interfaces," Ind. Eng. Chem., vol. 56, pp. 40-52 (Dec. 1964).
Gao, L. and McCarthy, T.J., "Teflon is Hydrophilic. Comments on Definitions of Hydrophobic, Shear versus Tensile Hydrophobicity, and Wettability Characterization," Langmuir, vol. 24, pp. 9183-9188 (Sep. 2, 2008).
George, P.A. et al., "Self-assembling polystyrene-block poly(ethylene oxide) copolymer surface coatings: resistance to protein and cell adhesion," Biomaterials, vol. 30, pp. 2449-2456 (May 2009).
Hall-Stoodley, L. et al., "Bacterial biofilms: from the natural environment to infectious diseases," Nature Reviews Microbiology, vol. 2, No. 2, pp. 95-108 (Feb. 2004).
Hejazi, et al., "Wetting Transitions in Two-, Three-, and Four-Phase Systems", Langmuir, vol. 28, pp. 2173-2180, (2012).
Inazaki, S. et al., "Surface modification of polytetrafluoroethylene with ArF excimer laser irradiation," J. Photopoly. Sci. Technol. vol. 7, No. 2, pp. 389-396 (1994).
International Search Report and Written Opinion issued by the European Patent Office as International Searching Authority for International Application No. PCT/US2013/021056 dated Jun. 6, 2013 (21 pages).
International Search Report and Written Opinion issued by the European Patent Office as International Searching Authority for International Application No. PCT/US2013/050403 dated Dec. 4, 2013 (21 pages).
International Search Report and Written Opinion issued by the International Searching Authority for International Application No. PCT/US14/25935 dated Jan. 23, 2015 (11 pages).
International Search Report and Written Opinion issued by the International Searching Authority for International Application No. PCT/US2013/050406 dated Nov. 20, 2013 (20 pages).
International Search Report issued by the European Patent Office as International Searching Authority for International Application No. PCT/US2012/021928, dated Aug. 10, 2012, 6 pages.
Israelachvili, Jacob N., "Intermolecular and Surface Forces—Third Edition," Academic Press, 706 pages (2011).
Karchmer, A.W. et al., "*Staphylococcus epidermidis* causing prosthetic valve endocarditis: microbiologic and clinical observations as guides to therapy," Ann. Intern. Med., vol. 98, pp. 447-455, (Apr. 1, 1983).
Keck et al., "Preparation of partially fluorinated aryl/alkyl vinylene ether polymers," Polymer International, vol. 62, Issue 10, pp. 1485-1491, Oct. 2013.
Khoo, X. et al., "Directed assembly of PEGylated-peptide coatings for infection-resistant titanium metal," J. Am. Chem. Soc., vol. 131, pp. 10992-10997 (No month listed 2009).
Kim, et al., "Structural Transformation by Electrodeposition on Patterned Substrates (STEPS): A new Versatile Nanofabrication Method," Nano Letters, vol. 12, No. 2, pp. A-G (Mar. 2011).
Kobayashi, H. and Owen, M.J., "Surface tension of poly[(3,3,4,4,5,5,6,6,6-nonafluorohexyl)-methylsiloxane]," Macromolecules, vol. 23, No. 23, pp. 4929-4933 (1990).
Lee, Woo, et al., "Fast fabrication of long-range ordered porous alumina membranes by hard anodization," Nature Mater., vol. 5, pp. 741-747 (Sep. 2006).
Lillehoj, et al., "A self-pumping lab-on-a-chip for rapid detection of botulinum toxin," Lab Chip, vol. 10, pp. 2265-2270 (Jun. 11, 2010).
Lin, T-K, et al., "Surface modification of polytetrafluoroethylene films by plasma pretreatment and graft copolymerization to improve their adhesion to bismaleimide," Polym. Int., vol. 58, No. 1, pp. 46-53 (Jan. 2009).
Meuler, Adam J. et al., "Relationships between Water Wettability and Ice Adhesion," ACS Applied Materials and Interfaces, vol. 2, No. 11, 31 pages (Oct. 15, 2010).
MicroSurfaces, Inc., "Anti-Stiction Coatings in MEMS Devices," MicroSurfaces, Inc., retreived from website URL: http://memsurface.com/stiction.html, 2 pages (retrieved on Dec. 8, 2011).
Munro, W.A. et al., "Deterioration of pH electrode response due to biofilm formation on the glass membrane," Sensors and Actuators B-Chem, vol. 37, pp. 187-194 (Dec. 1996).
Nguyen, et al., "Quantitative Testing of Robustness on Superomniphobic Surfaces by Drop Impact", Langmuir, 26(23):18369-18373, Dec. 7, 2010, 5 pages.
Nosonovsky, et al., "Biomimetic Superhydrophobic Surfaces: Multiscale Approach", Nano Letters, vol. 7, No. 9, pp. 2633-2637, Aug. 17, 2007.
O'Toole, G., et al., "Biofilm Formation as Microbial Development," Annu. Rev. Microbiol., vol. 54, pp. 49-79, 35 pages (2000).
Pokroy, B. et al., "Fabrication of BioInspired Actuated Nanostructures with Arbitrary Geometry and Stiffness," Adv. Mater., vol. 21, pp. 463-469 (Jan. 26, 2009).
Prakash and Gershenfeld, "Microfluidic Bubble Logic," Science, vol. 315, No. 5813, 5 pages (Feb. 9, 2007).
Rothemund, Paul W.K., "Folding DNA to create nanoscale shapes and patterns," Nature, vol. 440, pp. 297-302, Mar. 16, 2006.
Rowe, David J., "Chemistry and Technology of Flavors and Fragrances," Blackwell Publishing Ltd, 12 pages—Title Page, Copyright Page and Table of Contents Only (2005).
Shaffer, T.H. et al., "Liquid Ventilation," Pediatric Pulmonology, vol. 14, pp. 102-109 (Oct. 1992).
Skattum, L. et al., "Complement deficiency states and associated infections," Mol. Immunol., vol. 48, No. 14, pp. 1643-1655 (Aug. 2011).
Sohail, M.R. et al., "Risk factor analysis of permanent pacemaker infection," Clin. Infect. Dis., vol. 45, pp. 166-173 (Jul. 15, 2007).
Stober, W. and Fink, A., "Controlled growth of monodisperse silica spheres in the micron size range," Journal of Colloid and Interface Science, vol. 26, No. 1, pp. 62-69 (Jan. 1968).
Trevors, J.T., "Silver resistance and accumulation in bacteria," Enzyme Microb. Technol., vol. 9, No. 6, pp. 331-333 (Jun. 1987).
Varanasi, Kripa K. et al., "Frost formation and ice adhesion on superhydrophobic surfaces," Applied Physics Letters, vol. 97, pp. 234102-1-234102-3 (2010).
Vogel et al., "A Convenient Method to Produce Close- and Non-close-Packed Monolayers using Direct Assembly at the Air-Water Interface and Subsequent Plasma-Induced Size Reduction," Macromolecular Chemistry and Physics, vol. 212, pp. 1719-1734 (2011).
Vogel et al., "From soft to hard: the generation of functional and complex colloidal monolayers for nanolithography," Soft Matter, vol. 8, pp. 4044-4061 (2012).
Vogel, et al., "Wafer-Scale Fabrication of Ordered Binary Colloidal Monolayers with Adjustable Stoichiometries," Advanced Functional Materials, vol. 21, pp. 3064-3073, (2011).
Wasserscheid, P. and Welton, T., "Ionic Liquids in Synthesis," Wiley-VCH Verlag GmbH & Co., 380 pages (2002).
Wong, P.K. et al., "Deformation of DNA Molecules by Hydrodynamic Focusing," Journal of Fluid Mechanics, vol. 497, pp. 55-65 (2003).
Wong, T. S. et al., "Bioinspired self-repairing slippery surfaces with pressure-stable omniphobicity," Nature, vol. 477, No. 7365, pp. 443-447 (Sep. 22, 2011).
Xu, Q. et al., "Approaching Zero: Using Fractured Crystals in Metrology for Replica Molding," J. Am. Chem. Soc., vol. 127, No. 3, pp. 854-855 (2005).

(56) References Cited

OTHER PUBLICATIONS

Zhao, L. et al., "Antibacterial coatings on titanium implants," Journal of Biomedical Materials Research Part B: Applied Biomaterials, vol. 91, No. 1, pp. 470-480 (2009).
Liu et al., "Organogel-based Thin Films for Self-Cleaning on Various Surfaces," Advanced Materials, 5 pages, (2013).
Miller-Chou et al., "A review of polymer dissolution," Progress in Polymer Science, vol. 28, pp. 1223-1270, (2003).
Zhu et al., "Ice-phobic Coatings Based on Silicon-Oil-Infused Polydimethylsiloxane," American Chemical Society Applied Materials & Interfaces, vol. 5, pp. 4053-4062, (2013).
Abbott, et al., "Mass Production of Bio-Inspired Structured Surfaces", Proceedings of the Institution of Mechanical Engineers, Part C: Journal of Mechanical Engineering Science, 221(10):1181-1191, Oct. 1, 2007, 11 pages.
Bauer, et al., "The Insect-Trapping Rim of Nepenthes Pitchers", Plant Signaling & Behavior, 4(11):1019-1023, Nov. 1, 2009, 5 pages.
Bohn, et al., "Insect Aquaplaning: Nepenthes Pitcher Plants Capture Prey with the Peristome, a Fully Wettable Water-Lubricated Anisotropic Surface", PNAS, 101(39):14138-14143, Sep. 21, 2008, 6 pages.
Cassie, et al., "Wettability of Porous Surfaces", Transactions of the Faraday Society, vol. 40, pp. 546-551, Jan. 1944, 6 pages.
Hejazi, et al., "Wetting Transitions in Two-, Three-, and Four-Phase Systems", Langmuir, 2B:2173-2180, Nov. 5, 2011, 8 pages.
International Search Report and Written Opinion issued in PCT/US2012/021929, dated Aug. 21, 2012. 23 pages.
Ishino, et al., "Wicking Within Forests of Micropillars", EPL Journal, vol. 79, pp. 56005-p1-56005-p5, Sep. 2007, 5 pages.
Nguyen, "Quantitative Testing of Robustness on Superomniphobic Surfaces by Drop Impact", Langmuir, 26(23):18369-18373, Dec. 7, 2010, 5 pages.
Nosonovsky, "Multiscale Roughness and Stability of Superhydrophobic Biomimetic Interfaces", Langmuir, 23(6):3157-3161, Feb. 13, 2007, 5 pages.
Nosonovsky, et al., "Biomimetic Superhydrophobic Surfaces: Multiscale Approach", Nano Lett, 7(9):2633-2637, Aug. 17, 2007, 5 pages.
Raza, et al., "Superhydrophobic Surfaces by Anomalous Fluoroalkylsilane Self-Assembly on Silica Nanosphere Arrays", Langmuir, 26(15):12962-12972, Aug. 3, 2010, 11 pages.
Wenzel, "Resistance of Solid Surfaces to Wetting by Water", Industrial and Engineering Chemistry, 28(8):988-994, Aug. 1936, 7 pages.
Wong, et al., "Bioinspired Self-Repairing Slippery Surfaces with Pressure-Stable Omniphobicity", Nature, 477(7365):443-447, Jan. 1, 2011, 5 pages.
Wool, "Self-Healing Materials: A Review", Soft Matter, 4:400-418, Advance Article published online, Jan. 10, 2008, 19 pages.
Chinese Office Action issued by the State Intellectual Property Office of the People's Republic of China for Application No. 201280012205.0 dated May 13, 2015 (20 pages).
Chinese Office Action issued by the State Intellectual Property Office of the People's Republic of China for Application No. 201280012210.1 dated May 21, 2015 (30 pages).
Saido et al., "A Growth of Aspergillus Niger on Surface of Polymer Films was Observed by FT-IR and Scanning Electron Microscope," Materials Life, Oct. 8, 1991, vol. 3 No. 4, pp. 218-224. English translation.
Hozumi et al., "Hydrophobization of Metal/Metal Oxide Surfaces Using Monolayer Films," Journal of the Surface Finishing Society of Japan, Oct. 9, 2009, vol. 60, No. 1, pp. 16-20. English translation.

* cited by examiner

3D POROUS SOLID

REPLICA OF 3D POROUS SOLID
INFILTRATED WITH LIQUID B

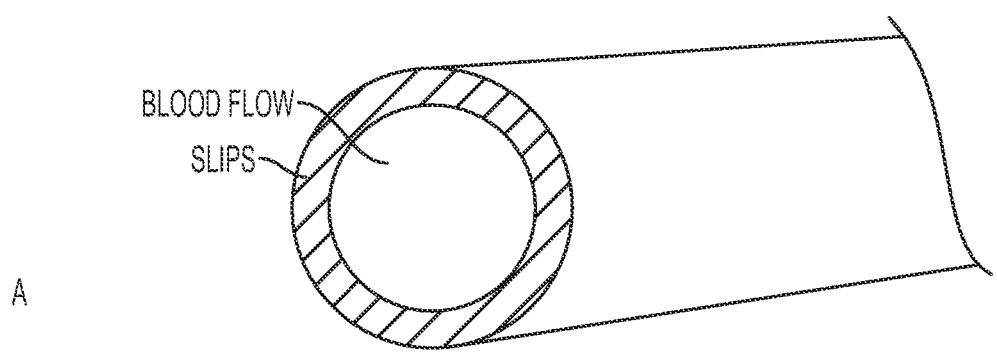
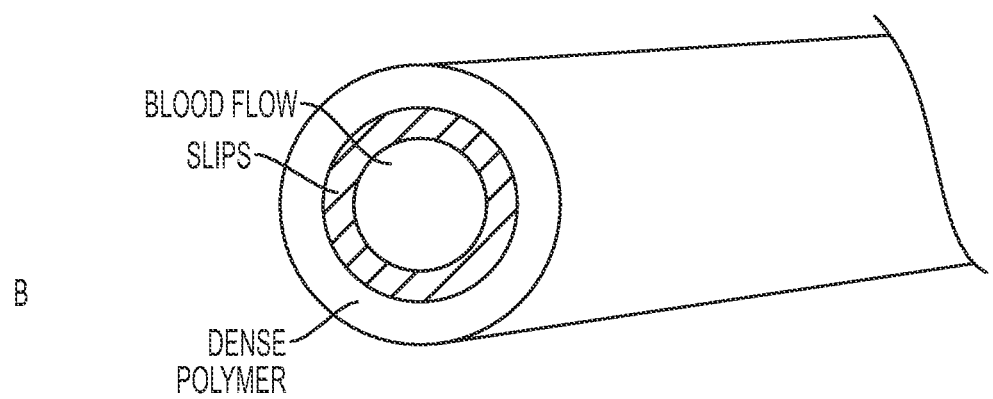
FIG. 22

SLIPPERY LIQUID-INFUSED POROUS SURFACES AND BIOLOGICAL APPLICATIONS THEREOF

RELATED APPLICATIONS

This application is a national stage application of International Application No.: PCT/US2012/021929, filed on Jan. 19, 2012, which claims priority to U.S. Patent Application No. 61/434,217, filed on Jan. 19, 2011; U.S. Patent Application No. 61/466,352, filed on Mar. 22, 2011; U.S. Patent Application No. 61/470,973, filed on Apr. 1, 2011; U.S. Patent Application No. 61/496,883, filed on Jun. 14, 2011; U.S. Patent Application No. 61/509,488, filed on Jul. 19, 2011, U.S. Patent Application No. 61/529,734 filed on Aug. 31, 2011; U.S. Patent Application No. 61/538,100, filed on Sep. 22, 2011, the contents of which are incorporated by reference herein in their entireties.

STATEMENT OF FEDERAL FUNDING

This invention was made with government support under Grant No. N66001-11-1-4180 awarded by the U.S Department of Defense. The government has certain rights in the invention.

INCORPORATION BY REFERENCE

All patents, patent applications, and publications cited herein are hereby incorporated by reference in their entirety in order to more fully describe the state of the art as known to those skilled therein as of the date of the invention described herein.

FIELD OF THE INVENTION

The present disclosure relates generally to surfaces that prevent adsorption or deposition from fluids, solids, or mixtures of fluids and solids of biological origin, and uses thereof.

BACKGROUND

Current development of liquid-repellent surfaces is inspired by the self-cleaning abilities of many natural surfaces on animals, insects, and plants. Water droplets on these natural surfaces maintain a near-spherical shape and roll off easily, carrying dirt away with them. The water-repellency function has been attributed to the presence of micro/nanostructures on many of these natural surfaces. These observations have led to enormous interest in the past decade in manufacturing biomimetic water-repellent surfaces, owing to their broad spectrum of potential applications, which range from water-repellent fabrics to friction reduction surfaces.

More specifically, synthetic liquid-repellent surfaces in the art are inspired by the lotus effect (Barthlott, W. & Neinhuis, C. Purity of the sacred lotus, or escape from contamination in biological surfaces. *Planta* 202, 1-8 (1997)) in which water droplets are supported by surface textures on a composite solid/air interface that enables water droplets to easily roll off the surface (Cassie, A. B. D. & Baxter, S. Wettability of porous surfaces. *Trans. Faraday Soc.* 40, 0546-0550 (1944); Cassie, A. B. D. & Baxter, S. Large contact angles of plant and animal surfaces. *Nature* 155, 21-22 (1945)). However, this approach has inherent limitations that severely restrict its applicability. First, trapped air is a largely ineffective cushion against organic fluids or complex mixtures that, unlike water, have low surface tension that strongly destabilizes suspended droplets (Shafrin, E. G. & Zisman, W. A. Constitutive relations in the wetting of low energy surfaces and the theory of the retraction method of preparing monolayers. *J. Phys. Chem.* 64, 519-524 (1960)).

Moreover, air trapped within surface textures cannot withstand pressure, so that liquids—particularly those with low surface tension—can easily penetrate the surface texture under even slightly elevated pressures or upon impact, conditions commonly encountered with driving rain or in underground transport pipes (Nguyen, T. P. N., Brunet, P., Coffinier, Y. & Boukherroub, R. Quantitative testing of robustness on superomniphobic surfaces by drop impact. *Langmuir* 26, 18369-18373 (2010)). Furthermore, synthetic textured solids are prone to irreversible defects arising from mechanical damage and fabrication imperfections (Quere, D. Wetting and roughness. *Annu. Rev. Mater. Res.* 38, 71-99 (2008); Bocquet, L. & Lauga, E. A smooth future? *Nature Mater.* 10, 334-337 (2011)). Because each defect enhances the likelihood of the droplet pinning and sticking in place, textured surfaces are not only difficult to optimize for liquid mobility but inevitably stop working over time as damage accumulates. Recent progress in pushing these limits with increasingly complex structures and chemistries remains outweighed by substantial tradeoffs in physical stability, optical properties, large-scale feasibility, and/or difficulty and expense of fabrication (Tuteja, A. et al., *Science* 318, 1618-1622 (2007); Tuteja, A., et al., *Proc. Natl. Acad. Sci. USA* 105, 18200-18205 (2008); Ahuja, A., et al., *Langmuir* 24, 9-14 (2008); Li, Y., et al., *Angew. Chem. Int. Ed.* 49, 6129-6133 (2010)).

Despite over a decade of intense research, surfaces in the art are still plagued with problems that restrict their practical applications: they exhibit limited oleophobicity with high contact angle hysteresis; fail under pressure; cannot self-heal when damaged; and are expensive to produce.

For example, no surfaces that delay or prevent blood clotting, a process that relies on adhesion of platelets and proteins to a surface as a first step, have been developed. Soluble anti-coagulants, such as heparin, must be added to flowing blood in any extracorporeal shunt to prevent clot formation. Certain polymeric species, such as polyethylene glycol (PEG) chains, can influence the surface hydration layer to prevent protein adsorption and control blood clotting to a limited extent (Barstad, R. M, et al., *Thrombosis and haemostasis* 79, 302-305 (1998); Niimi, Y., et al., *Anesth. Analg.* 89, 573-579 (1999); Chen, S. et al., *Polymer* 51, 5283-5293 (2010)). However, they are not fully effective and soluble anticoagulants still must be added to the blood.

Bacteria exist in their natural state predominantly as members of biofilms—structured, multicellular communities adherent to surfaces in natural and anthropogenic environments. These communities are composed of many cells embedded within a polymeric organic matrix. Biofilm formation is of concern to industry and healthcare because it causes contamination of plumbing, oil wells, heat exchangers, building ventilation, food storage, medical implants, and other systems. Biofilms threaten human health by triggering an immune response, releasing harmful endotoxins and exotoxins, and clogging indwelling catheters; in fact, biofilms are responsible for nearly 100,000 nosocomial deaths annually in the United States and 80% or more of all microbial infections in humans.

Systemic and topical antimicrobial products have become extensively used to combat biofilm contamination in health care, agriculture, and industrial settings, and increasingly by the general public as well. Commercial products employ a wide variety of active chemical agents, or biocides, often delivered in liquid form and sometimes as vapor. One review of antiseptics and disinfectants identifies 12 classes of liquid agents and 5 common types of vapor-phase sterilants. Regardless of the particular chemistry or mechanism, biocides must be able to reach the target cell to cause damage. At the multicellular level, therefore, the effective biocide must penetrate into the extracellular matrix (ECM)—the slime-like "cement" of biofilm. Biofilms, however, offer their member cells protection from environmental threats. It has been reported that ECM acts as a diffusion barrier and as a charged binding filter for certain antibiotics, and that it complements enzymes and multidrug resistance pumps on cells that remove antimicrobials. The resistance to threats covers a wide range of treatments: biofilms exposed to chlorine bleach for 60 minutes are reported to still have live cells; biofilms in pipes continuously flushed over 7 days with multiple biocides recolonize the pipes, and biofilms have been reported to survive in bottled iodine solution for up to 15 months. Biofilms' resistance to antimicrobials may be related to the extreme nonwettability of their surface as well as resistance to vapor penetration.

Developing biomedical materials that are resistant to biofilm formation before it causes damage or that prevent its robust attachment would significantly reduce the rate of nosocomial infections and the costs associated with treating them. Many negative effects of bacterial colonization stem from the formation of biofilms as protective structures and the associated cooperative behavior of bacterial cells. Persistently bacteria-resistant materials are difficult to achieve by surface chemistry alone. Even if bacteria are unable to attach directly to a material, nonspecific adsorption of proteins or secreted surfactants to the surface eventually masks the underlying chemical functionality with a "conditioning film." These organic molecules will change the wettability and surface charge of the original surface, and after about 4 hours, a certain degree of uniformity is reached and the composition of the adsorbed material becomes material independent. Materials that rely on leaching impregnated antimicrobials such as silver ion (Ag+) for their function are furthermore limited by the finite reservoir of the active agent. Furthermore, the use of leaching paints containing copper or triorganotin to resist biofouling on ship hulls is increasingly prohibited because of their high environmental toxicity. Some recent research on the effects of nano- or microscale topographical features on bacterial adhesion and subsequent biofilm formation has suggested a possibly more persistent and environmentally sustainable form of controlling bacterial attachment to surfaces, but no evidence yet suggests that this approach can effectively prevent mature biofilm formation or attachment.

There exists a need for an inexpensive, chemically inactive, synthetic slippery surface capable of repelling fluids, withstanding high-impact pressure, and self-healing.

SUMMARY OF THE INVENTION

Disclosed herein are synthetic slippery liquid-infused porous surfaces ("SLIPS") for repelling fluids of biological origin.

In one embodiment, an article for repelling a biological material comprising a lubricating fluid layer is disclosed. The lubricating fluid layer is immiscible with the repelled biological material, and forms an ultra-smooth surface. In some embodiments, the lubricating fluid layer is stabilized in place by the underlying substrate. The article has a solid substrate on which the lubricating fluid adheres. The substrate is preferentially wetted by the lubricating fluid. The solid substrate and lubricating fluid form a slippery surface configured and arranged to contact a biological material.

In another embodiment, an article having a repellant surface is disclosed. A lubricating fluid wets and adheres to a solid substrate comprising a roughened surface to form a stabilized liquid overlayer. The roughened surface and the liquid covering it have an affinity for each other such that the lubricating liquid is substantially immobilized on the substrate.

In another embodiment, a device capable of repelling a biological material comprising a lubricating fluid layer is disclosed. The lubricating fluid layer is immiscible with the repelled biological material, and forms an ultra-smooth surface. The device has a solid substrate on which the lubricating fluid adheres. The substrate is preferentially wetted by the lubricating fluid. The solid substrate and lubricating fluid form a slippery surface configured and arranged to contact a biological material.

In another embodiment, a method of preventing adhesion, adsorption, surface-mediated clot formation, or coagulation of a biological material is disclosed. The method comprises providing a lubricating fluid layer, wherein the lubricating fluid is immiscible with the biological material; providing a solid substrate, wherein the lubricating fluid adheres to the substrate to form a slippery liquid-infused surface; and contacting the biological sample to the surface.

In one or more embodiments, a method of making an article having a slippery surface is disclosed. A solid substrate is roughened and contacted with a lubricating liquid that forms a lubricating fluid layer. The roughened solid substrate and the lubricating layer form a slippery surface, and are configured and arranged for contact with a material that is immiscible with the lubricating liquid.

In another embodiment, an optically transparent device that prevents adhesion of biological material is disclosed. A roughened surface that is a transparent window is wetted by a lubricating fluid that adheres to the roughened surface to form an over-coated layer. The roughened surface of the transparent window has a greater affinity towards the lubricating fluid as compared to a biological material. Moreover, the index of refraction of the lubricating liquid is substantially similar to the index of refraction of the roughened surface. The lubricating liquid and the biological material are substantially chemically inert with each other. In one or more aspects, the device is a biological sensor window.

In one or more embodiments, an article having a low adhesion surface for preventing or reducing biofilm attachment is disclosed. The article comprises a solid substrate having a roughened surface and a lubricating fluid that adheres to and preferentially wets the substrate to form a liquid upper surface. The liquid upper surface is configured and arranged to contact a biological material of interest. The lubricating fluid is immiscible with the biological material, and the biological material exhibits little or no adhesion to the article.

In any of the preceding embodiments, the following condition is satisfied: $\gamma_{BX} \cos \theta_{BX} - \gamma_{AX} \cos \theta_{AX} > 0$ (e1), wherein $\gamma_{AX}$ is the interfacial energies of the biological material with a surrounding medium, and wherein $\gamma_{BX}$ is the interfacial energies of the lubricating fluid with the surrounding medium, and wherein $\theta_{AX}$ is the equilibrium contact angle of the biological material on a flat solid surface immersed under the surrounding medium, and wherein $\theta_{BX}$ is the equilibrium contact angle of the liquid of the lubricating fluid on a flat solid surface immersed under the surrounding medium.

In one or more embodiments, the following two conditions are satisfied when the article is exposed to Medium X, where X is air/gas/water/immiscible biological material: $R(\gamma_{BX} \cos \theta_{BX} - \gamma_{AX} \cos \theta_{AX}) - \gamma_{AB} > 0$ (e2) and $R(\gamma_{BX} \cos \theta_{BX} - \gamma_{AX} \cos \theta_{AX}) + \gamma_{AX} - \gamma_{BX} > 0$ (e3), wherein $\gamma_{AX}$ is the interfacial energies of the biological material with a surrounding medium, $\gamma_{BX}$ is the interfacial energies of the lubricating fluid with the surrounding medium, $\gamma_{AB}$ is the interfacial energies of the biological material and the lubricating fluid interface, $\theta_{AX}$ is the equilibrium contact angle of the biological material on a flat solid surface immersed under the surrounding medium, $\theta_{BX}$ is the equilibrium contact angle of the lubricating fluid on a flat solid surface immersed under the surrounding medium, and R is a roughness factor of the roughened surface.

In one or more aspects, the lubricating fluid prevents adhesion, coagulation, or clot formation of biological materials.

In the above embodiments, wherein the method further mediates inflammation, wound healing, plaque disposition, or foreign body response.

In the above embodiments, the method inhibits inflammation, wound healing, plaque disposition, or foreign body response.

In the above embodiments, the method prevents inflammation, wound healing, plaque disposition, or foreign body response.

In the above embodiments, the method further prevents bacterial contamination.

In one or more aspects, wherein the biological material is contacted with the surface at a fluid impact pressures is on the order of $10^3$-$10^7$ Pa.

In one or more aspects, the surface is selected from the group consisting of a cannula, connector, catheter, needle, capillary tube, tubing, syringe and combinations thereof.

In one or more aspects, the surface is selected from the group consisting of a slide, plate, film, work surface, well, well plate, Petri dish, tile, jar, flask, beaker, vial, test tube, column, container, cuvette, bottle, drum, vat, tank, and combinations thereof.

In one or more aspects, the surface is selected from the group consisting of a clamp, skin hook, cuff, retractor, shunt, needle, capillary tube, tubing, and combinations thereof.

In one or more aspects, the surface is selected from the group consisting of an endotracheal tube, ventilator, associated ventilator tubing, drug delivery vehicle, syringe, endoscope, dialysis equipment, central veno-venous hemofiltration device, extracorporeal membrane oxygenation equipment, and combinations thereof.

In one or more aspects, the surface is selected from the group consisting of an organ, artificial organ, implant, and combinations thereof.

In one or more aspects, the surface is selected from the group consisting of a biosensor, biological microelectromechanical devices (bioMEMs), bioelectrode, and combinations thereof.

In one or more aspects, the surface is a wound dressing.

In one or more aspects, the substrate is preferentially wetted by the lubricating fluid. In one or more aspects, the lubricating fluid infiltrates the substrate by capillary action.

In one or more aspects, the solid substrate is electrically conductive, non-conductive, magnetic, non-magnetic, elastic, non-elastic, light sensitive, or not light sensitive.

In one or more aspects, the solid substrate is silanized.

In one or more aspects, the substrate is a roughened surface comprising a porous material.

In the above embodiments, microparticles or nanoparticles are applied to a flat substrate to form a roughened, porous substrate.

In the above embodiments, microparticles or nanoparticles are applied to the substrate using photolithography, projection lithography, e-beam writing or lithography, depositing nanowire arrays, growing nanostructures on the surface of a substrate, soft lithography, replica molding, solution deposition, solution polymerization, electropolymerization, electrospinning, electroplating, vapor deposition, layered deposition, rotary jet spinning of polymer nanofibers, contact printing, etching, transfer patterning, microimprinting, self-assembly, boehmite (γ-AlO(OH)) formation, spray coated, and combinations thereof.

In one or more aspects, the substrate consists of a fluoropolymer.

In one or more aspects, the biological material is a fluid selected from the group consisting of whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, and combinations thereof.

In one or more aspects, the biological material is a solution or suspension containing bacteria selected from the group consisting of *Actinobacillus* (e.g., *Actinobacillus actinomycetemcomitans*), *Acinetobacter* (e.g., *Acinetobacter baumannii*), *Aeromonas, Bordetella* (e.g., *Bordetella pertussis, Bordetella bronchiseptica*, and *Bordetella parapertussis*), *Brevibacillus, Brucella, Bacteroides* (e.g., *Bacteroides fragilis*), *Burkholderia* (e.g., *Burkholderia cepacia* and *Burkholderia pseudomallei*), *Borelia* (e.g., *Borelia burgdorfen*), *Bacillus* (e.g., *Bacillus anthracis* and *Bacillus subtilis*), *Campylobacter* (e.g., *Campylobacter jejuni*), *Capnocytophaga, Cardiobacterium* (e.g., *Cardiobacterium hominis*), *Citrobacter, Clostridium* (e.g., *Clostridium tetani* or *Clostridium difficile*), *Chlamydia* (e.g., *Chlamydia trachomatis, Chlamydia pneumoniae*, and *Chlamydia psiffaci*), *Eikenella* (e.g., *Eikenella corrodens*), *Enterobacter, Escherichia* (e.g., *Escherichia coli*), *Francisella* (e.g., *Francisella tularensis*), *Fusobacterium, Flavobacterium, Haemophilus* (e.g., *Haemophilus ducreyi* or *Haemophilus influenzae*), *Helicobacter* (e.g., *Helicobacter pylori*), *Kingella* (e.g., *Kingella kingae*), *Klebsiella* (e.g., *Klebsiella pneumoniae*), *Legionella* (e.g., *Legionella pneumophila*), *Listeria* (e.g., *Listeria monocytogenes*), *Leptospirae, Moraxella* (e.g., *Moraxella catarrhalis*), *Morganella, Mycoplasma* (e.g., *Mycoplasma hominis* and *Mycoplasma pneumoniae*), *Mycobacterium* (e.g., *Mycobacterium tuberculosis* or *Mycobacterium leprae*), *Neisseria* (e.g., *Neisseria gonorrhoeae* or *Neisseria meningitidis*), *Pasteurella* (e.g., *Pasteurella multocida*), *Proteus* (e.g., *Proteus vulgaris* and *Proteus mirablis*), *Prevotella, Plesiomonas* (e.g., *Plesiomonas shigelloides*), *Pseudomonas* (e.g., *Pseudomonas aeruginosa*), *Providencia, Rickettsia* (e.g., *Rickettsia rickettsii* and *Rickettsia typhi*), *Stenotrophomonas* (e.g., *Stenotrophomonas maltophila*), *Staphylococcus* (e.g., *Staphylococcus aureus* and *Staphylococcus epidermidis*), *Streptococcus* (e.g., *Streptococcus viridans, Streptococcus pyogenes* (group A), *Streptococcus agalactiae* (group B), *Streptococcus bovis*, and *Streptococcus pneumoniae*), *Streptomyces* (e.g., *Streptomyces hygroscopicus*), *Salmonella* (e.g., *Salmonella enteriditis, Salmonella typhi*, and *Salmonella typhimurium*), *Serratia*

(e.g., *Serratia marcescens*), *Shigella*, *Spirillum* (e.g., *Spirillum minus*), *Treponema* (e.g., *Treponema pallidum*), *Veillonella*, *Vibrio* (e.g., *Vibrio cholerae*, *Vibrio parahaemolyticus*, and *Vibrio vulnificus*), *Yersinia* (e.g., *Yersinia enterocolitica*, *Yersinia pestis*, and *Yersinia pseudotuberculosis*), *Xanthomonas* (e.g., *Xanthomonas maltophilia*) and combinations thereof.

In one or more aspects, the biological material is a solution or suspension containing particles selected from the group consisting of a member of the genus *Aspergillus* (e.g., *Aspergillus flavus*, *Aspergillus fumigatus*, *Aspergillus glaucus*, *Aspergillus nidulans*, *Aspergillus niger*, and *Aspergillus terreus*), *Blastomyces dermatitidis*, *Candida* (e.g., *Candida albicans*, *Candida glabrata*, *Candida tropicalis*, *Candida parapsilosis*, *Candida krusei*, and *Candida guillermondii*), *Coccidioides immitis*, *Cryptococcus* (e.g., *Cryptococcus neoformans*, *Cryptococcus albidus*, and *Cryptococcus laurentii*), *Histoplasma capsulatum* var. *capsulatum*, *Histoplasma capsulatum* var. *duboisii*, *Paracoccidioides brasiliensis*, *Sporothrix schenckii*, *Absidia corymbifera*; *Rhizomucor pusillus*, *Rhizopus arrhizous*, and combinations thereof.

In one or more aspects, the biological material is a solution or suspension containing particles selected from the group consisting of normal cells, diseased cells, parasitized cells, cancer cells, foreign cells, stem cells, and infected cells, microorganisms, viruses, virus-like particles, bacteria, bacteriophage, proteins, cellular components, cell organelles, cell fragments, cell membranes, cell membrane fragments, viruses, virus-like particles, cytosolic proteins, secreted proteins, signaling molecules, embedded proteins, nucleic acid/protein complexes, nucleic acid precipitants, chromosomes, nuclei, mitochondria, chloroplasts, flagella, biominerals, protein complexes, and minicells.

In one or more aspects, the lubricating fluid is capable of self-healing by wicking back to the damaged region of the substrate after physical damage of the substrate to form an ultra-smooth surface.

In the above embodiments, a recovery time for self-healing occurs in less than 50 ms, 60 ms, 70 ms, 80 ms, 90 ms, 100 ms, 110 ms, 120 ms, 130 ms, 140 ms, 150 ms, 160 ms, 170 ms, 180 ms, 190 ms, 200 ms, 210 ms, 220 ms, 230 ms, 240 ms, 250 ms, 1 second, 5 seconds 10 seconds, 30 seconds, 60 seconds, 90 seconds, or 120 seconds or more.

In one or more aspects, the substrate has a plurality of holes, three-dimensionally interconnected network of holes and one or more materials, or random array of fibrous materials.

In one or more aspects, the substrate consists of a material selected from the group consisting of polymers, metals, sapphire, glass, diamond, graphite, black carbon, or ceramics. In one or more embodiments, the substrate is a hemocompatible material. In one aspect, the hemocompatible material is a silicon rubber or polysulfone.

In one or more aspects, the substrate is a polymer selected from the group consisting of polytetrafluoroethylene, polyvinylfluoride, polyvinylidene fluoride, and fluorinated ethylene propylene.

In one or more aspects, the lubricating fluid has a density greater than the density of the biological material.

In one or more aspects, the lubricating fluid has a density greater than lubricating fluid has a density that is more than 1.0 g/cm$^3$, 1.6 g/cm$^3$, or 1.9 g/cm$^3$.

In one or more aspects, the lubricating fluid comprises a fluid selected from the group consisting of tertiary perfluoroalkylamines, perfluorotri-n-butylamine, perfluoroalkylsulfides, perfluoroalkylsulfoxides, perfluoroalkylethers, perfluorocycloethers, perfluoropolyethers, perfluoroalkylphosphines, and perfluoroalkylphosphineoxides, and combinations thereof.

BRIEF DESCRIPTION OF THE DRAWINGS

FIG. 22 is a schematic illustrating the whole wall of a catheter with SLIPS (22A) and a catheter lined with a dense, nonporous material and SLIPS (22B).

DETAILED DESCRIPTION OF THE INVENTION

Figure 1:
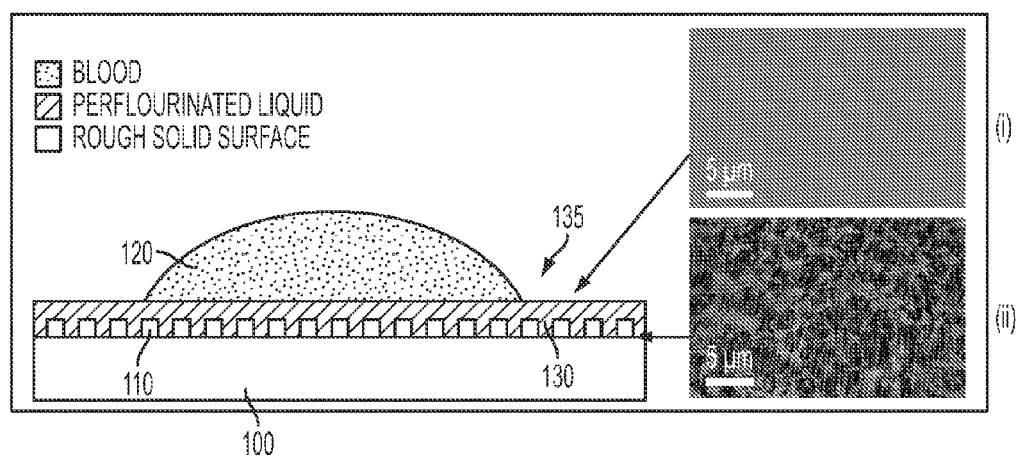
FIG. 1 is an image showing the structure of SLIPS, which is created by infiltrating a porous solid with a low surface energy, a chemically inert liquid that leads to a physically smooth and chemically homogeneous lubricating film on the surface of the substrate; the top and bottom scanning electron microscope (SEM) images FIG. 1(*i*)-(*ii*) show ultra-smoothness of the lubricating fluid and a porous structure of the rough solid surface, respectively.

Disclosed herein are synthetic slippery liquid-infused porous surfaces ("SLIPS") for repelling, preventing attachment, or reducing attachment of fluids ("Liquid A") or solids ("Object A") of biological origin. As referred to herein, Liquid A, Object A, and biological material are used interchangeably. Adhesion and absorption of material of biological origin are also reduced or prevented by SLIPS.

SLIPS are synthetic surfaces that consist of nano/micro-structured substrates infused with a lubricating fluid that is locked in place by a substrate to form a stable, defect-free, inert "slippery" interface capable of repelling complex fluids, gases, and molecules or particulates contained within liquids of varying surface tensions (together referred to as Liquid A), as well as solids. For example, liquids such as hydrocarbons, organic solvents, and the like can be repelled. The biological liquids refer to both pure liquids and complex fluids, such as blood flow (see, e.g., FIG. 11 and FIG. 12). As another example, solids like bacteria, proteins, and the like can be repelled by SLIPS. In addition, natural and synthetic solutions such as those used in medicines, intravenous solutions, pharmaceutical manufacturing, and medication delivery systems can be repelled by SLIPS.

The SLIPS consists of a porous surface layer, or a 'rough' layer of raised surface features in an array, which is infiltrated with a low surface energy liquid. The combination of lubricating fluid over a rough surface creates an ultra-smooth surface that is slippery and resists or reduces adhesion by particles and immiscible liquids. In some embodiments, the lubricating fluid is stabilized in place by the underlying substrate. In one or more aspects, the lubricating fluid is reduced to the level of the features of the substrate. These unique features of SLIPS allow the passage of biological material at high flow rates without permitting the material to form clots on, adhere to, attach, or otherwise foul SLIPS. SLIPS are also capable of restoring their exceptional liquid repellency when physically damaged. The fast self-healing times are a result of the lubricating fluid wicking fluid into damaged sites on the underlying substrate to restore SLIPS to a smooth defect-free surface. These surfaces can be used in laboratories, as a coating on medical devices and medical equipment, and for medical applications such as anticoagulation and anti-biofilm formation.

Generally, SLIPS can be manufactured by providing a liquid (e.g., chemically-inert, high-density fluid) over a roughened surface featuring micro- or nanoscale topographies, where the fluid fills the voids and spaces defined by the roughened surface and covers the topographical features. The fluid repellency and the self-healing property of SLIPS can be attributed to the ultra-smoothness of the surface of the fluid, which is capable of recovering its original shape upon external deformation. As used herein, "ultra-smooth" surface means a surface having a roughness factor that is equal or close to 1, where the roughness factor (R) is defined by the ratio of the real surface area to the projected surface area. Because fluid surfaces generally have a roughness factor of 1, and the top surface in SLIPS is a lubricating fluid that fully coats the substrate above its hills, surfaces such as that shown in FIG. 1 can be called ultra-smooth. In certain embodiments, ultra-smooth surface can have an average surface roughness is on the order of or less than about 1 nm. In certain embodiments, "ultra-smooth" may refer to a substantially molecularly or even atomically flat surface. The absence of any defects or roughness on such a surface may aid in minimizing the pinning points for a sliding fluid, thus reducing the contact angle hysteresis, rendering it nearly friction-free and slippery. A detailed discussion of the ultra-smooth surfaces is found in U.S. Patent Application No. 61/434,217, filed on Jan. 19, 2011, U.S. Patent Application No. 61/466,352, filed on Mar. 22, 2011, and co-filed International Application No. PCT/US12/21928 entitled "Slippery Surfaces With High Pressure Stability, Optical Transparency, and Self-Healing Characteristics" filed Jan. 19, 2012, which are incorporated by reference in their entirety.

Figure 6A:
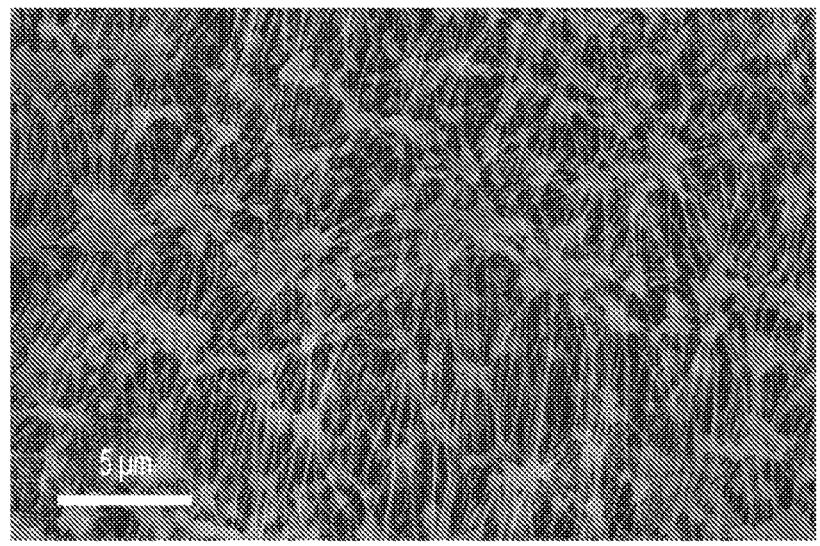
FIG. 6 shows (A) a scanning electron microscope image of the surface morphologies of a 3D porous solid; and (B) a replica of a slippery surface formed by infiltrating the 3D porous solid of 6A with lubricating fluid showing that the lubricating fluid overcoats the surface topographies, forming an ultra-smooth layer without asperity (e.g., average roughness on the order of or less than about 1 nm based on high resolution atomic force microscopy measurements, see inset (6C) as viewed at low (6B) and high (inset 6(D)) resolution in accordance with certain embodiments.
Figure 6B:
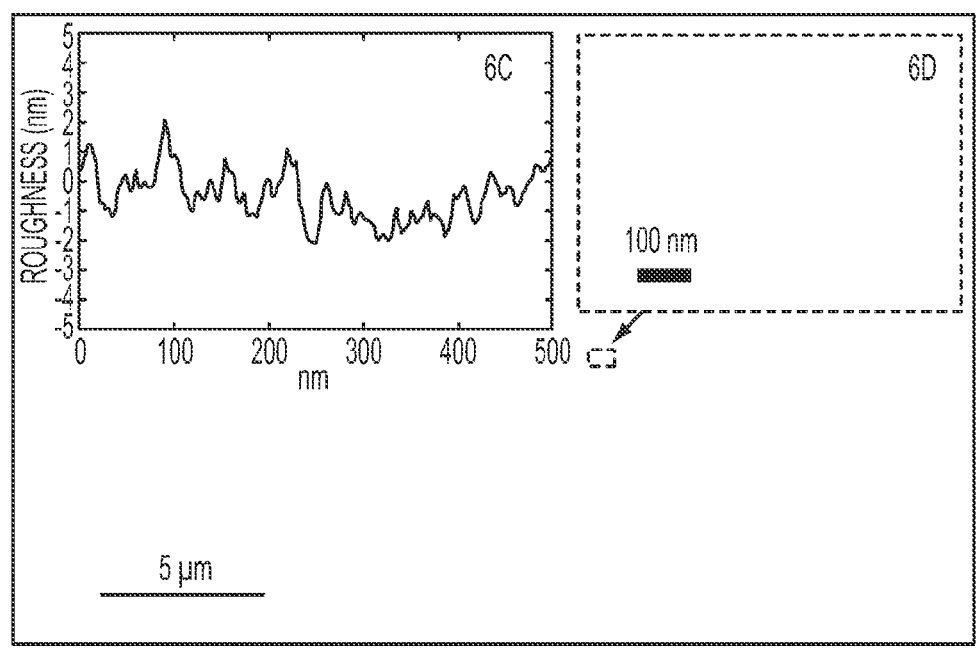

A schematic of the overall design of SLIPS is illustrated in FIG. 1. As shown, the article includes a surface 100 having raised features 110 that provide a certain roughness with lubricating fluid applied thereon. Lubricating fluid 130 wets the roughened surface, filling the hills and valleys of the roughened surface 110, and forming an ultra-smooth surface 135 over the roughened surface. The top (i) and bottom (ii) scanning electron microscope (SEM) images in the inset of FIG. 1 ultra-smoothness of the SLIPS surface and the porous structure of the underlying rough solid surface, respectively. The surface smoothing effect of the SLIPS device is further illustrated in FIG. 6A and FIG. 6B). FIG. 6 (A) shows a scanning electron microscope image of the surface morphologies of a 3D porous solid. FIG. 6(B) shows a photograph at the same magnification of a slippery surface formed by infiltrating the 3D porous solid shown in FIG. 6(A) with lubricating fluid. The lubricating fluid overcoats the surface topographies of the porous solid to form an ultra-smooth layer without asperity (e.g., average roughness on the order of or less than about 1 nm based on high resolution atomic force microscopy measurements). In certain embodiments, the average surface roughness of SLIPS is on the order of or less than about 1 nm based on high resolution atomic force microscopy measurements. The presence of the micro/nanostructures can significantly enhance the wetting of lubricating fluid, thereby creating a uniformly-coated slippery functional layer over the topographies.

Any arbitrary liquid (e.g., a biological fluid), gas, molecule, or particulate contained within liquids may be strongly repelled from the ultra-smooth lubricating fluid surface. Moreover, the ultra-low adhesion characteristics of SLIPS, which also prevents adsorption, adhesion, and attachment of objects on SLIPS, prevents contamination of these surfaces by material of biological origin. The adhesion, adsorption, or attachment of biological materials can be completely prevented by SLIPS. In some embodiments, SLIPS reduces the adhesion, adsorption, or attachment of biological materials on surfaces. In one aspect, SLIPS significantly reduces adhesion, adsorption, or attachment of biological materials on surfaces. In one or more aspects, SLIPS reduces adhesion, adsorption, or attachment of materials of biological origin on surfaces by 50%, 60%, 70%, 80%, 90%, 95%, 98%, or 99%.

A wide range of materials can be repelled by the slippery surfaces of the present disclosure. More specifically, polar and non-polar liquids, as well as polar and non-polar liquids in their solidified forms can be repelled by SLIPS. For example, hydrocarbons and their mixtures (e.g., from pentane up to hexadecane and mineral oil, ketones (e.g., acetone, etc.), alcohols (e.g., methanol, ethanol, isopropanol, dipropylene glycol, ethylene glycol, and glycerol, etc.), water (with a broad range of salinity, e.g., sodium chloride from 0 to 6.1 M; potassium chloride from 0 to 4.6 M, etc.), physiological buffers, acids (e.g., concentrated hydrofluoric acid, hydrochloric acid, nitric acid, etc), bases (e.g., potassium hydroxide, sodium hydroxide, etc), ice, and the like can be repelled by SLIPS. Moreover, biological objects, such as small animals, protozoa, bacteria, viruses, and the like can be repelled by surfaces made in accordance with the present disclosure. Similarly, solid particles suspended in liquid can be repelled by SLIPS. Non-limiting examples of such solid particles in liquid include bodily fluids, fecal matter, and the like.

The list is intended to be exemplary and the slippery surfaces of the present disclosure are envisioned to successfully repel numerous other types of biological materials.

Substrates

In one embodiment, the substrate is a low-surface energy porous solid. In the disclosed embodiments, the substrate is preferentially wetted by the lubricating fluid rather than by the fluid to be repelled. It can have a roughened or smooth surface. As used herein, the term "roughened surface" is a substrate that includes both the surface of a three-dimensionally porous material as well as solid surface having certain topographies, whether they have regular, quasi-regular, or random patterns. In some embodiments, the substrate is roughened by incorporation of microtextures. In other embodiments, the substrate is roughened by incorporation of nanotextures. Physically, the large surface area provided by micro/nanoscale roughness not only facilitates complete wetting by the lubricating fluid but also strengthens the adhesion of lubricating fluid (Liquid B) within the porous solid.

Figure 7A:
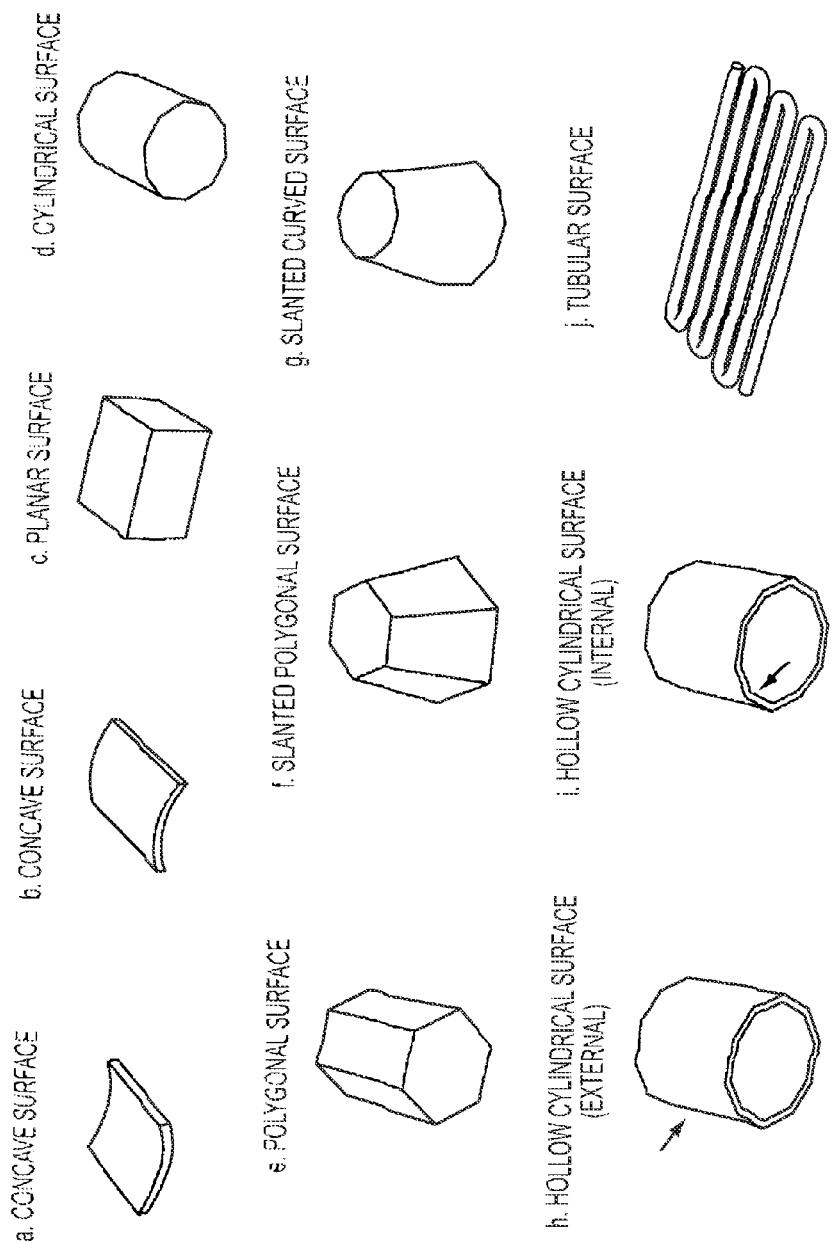
FIG. 7A shows several planar and non-planar surfaces over which the slippery surface can be formed in accordance with certain embodiments.
Figure 7B:
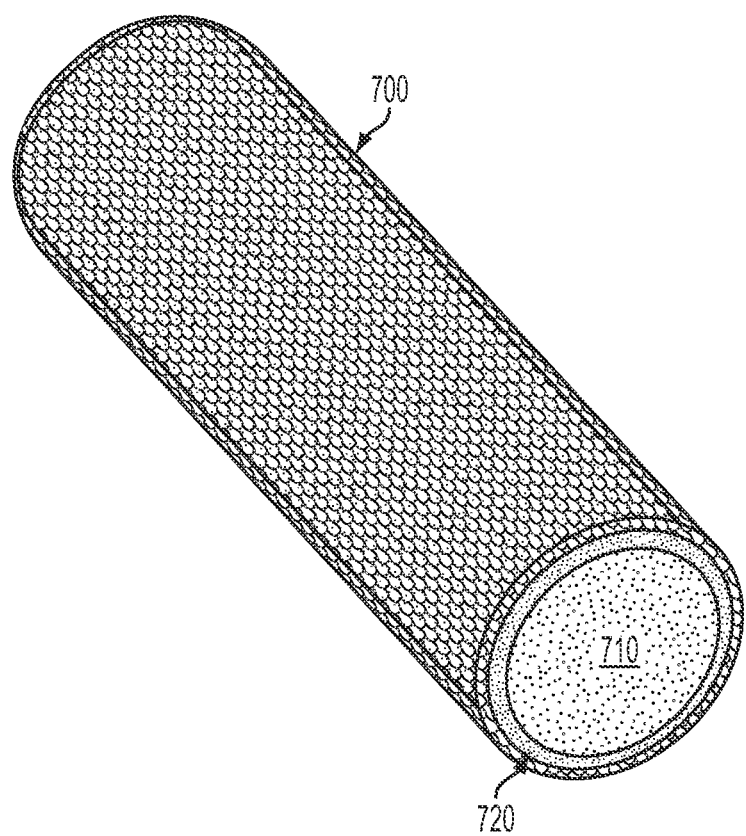
FIG. 7B shows SLIPS formed over a cylindrical solid core in accordance with certain embodiments.
Figure 7C:
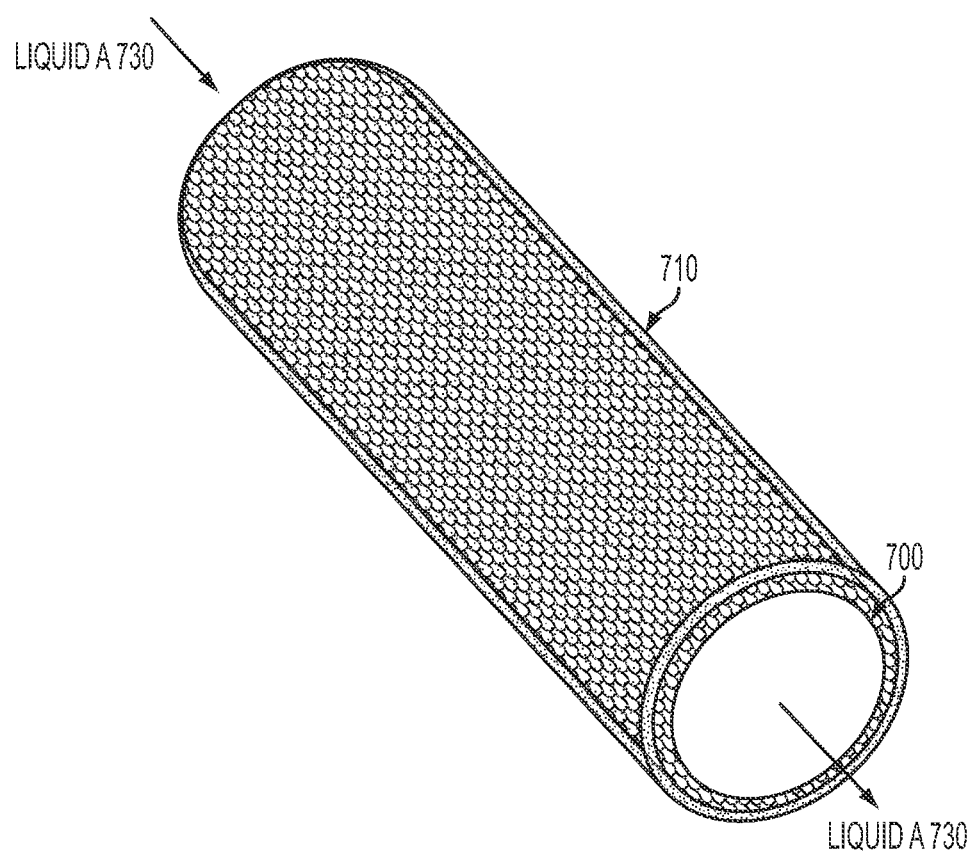
FIG. 7C shows SLIPS formed on the sidewall of the interior of a tubing/pipe and the like in accordance with certain embodiments.
Figure 7D:
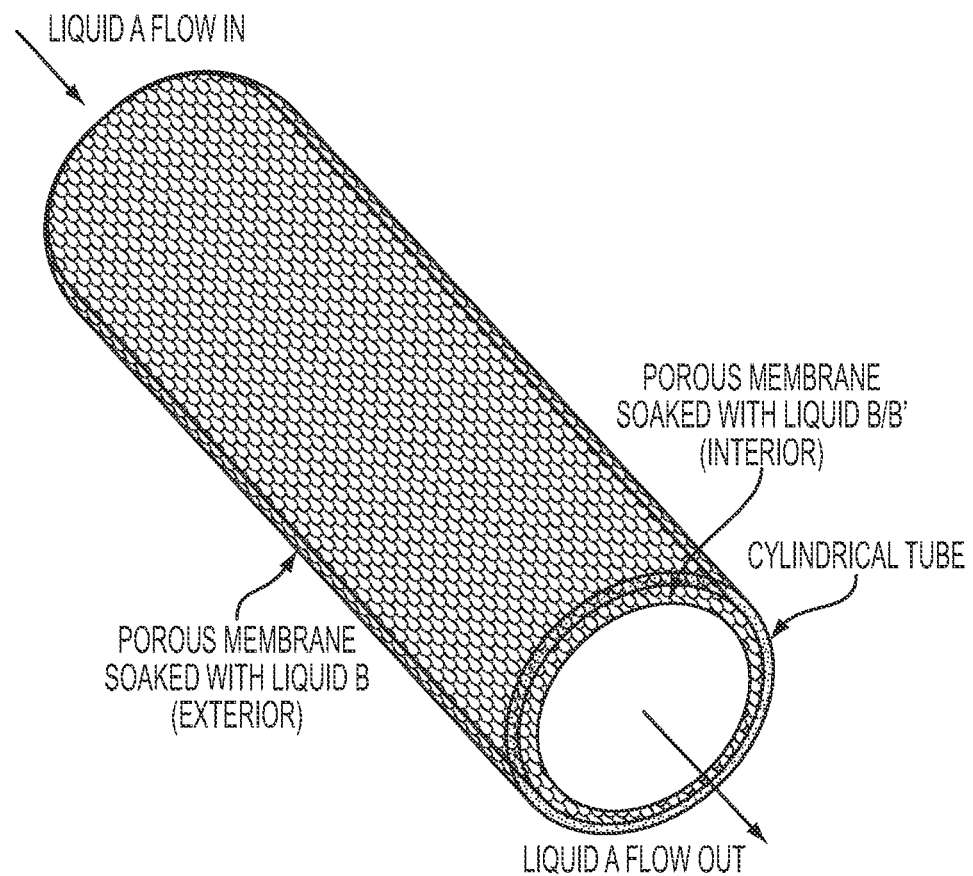
FIG. 7D shows SLIPS formed on the sidewall of both of the interior and exterior of a tubing/pipe and the like in accordance with certain embodiments.
Figure 7E:
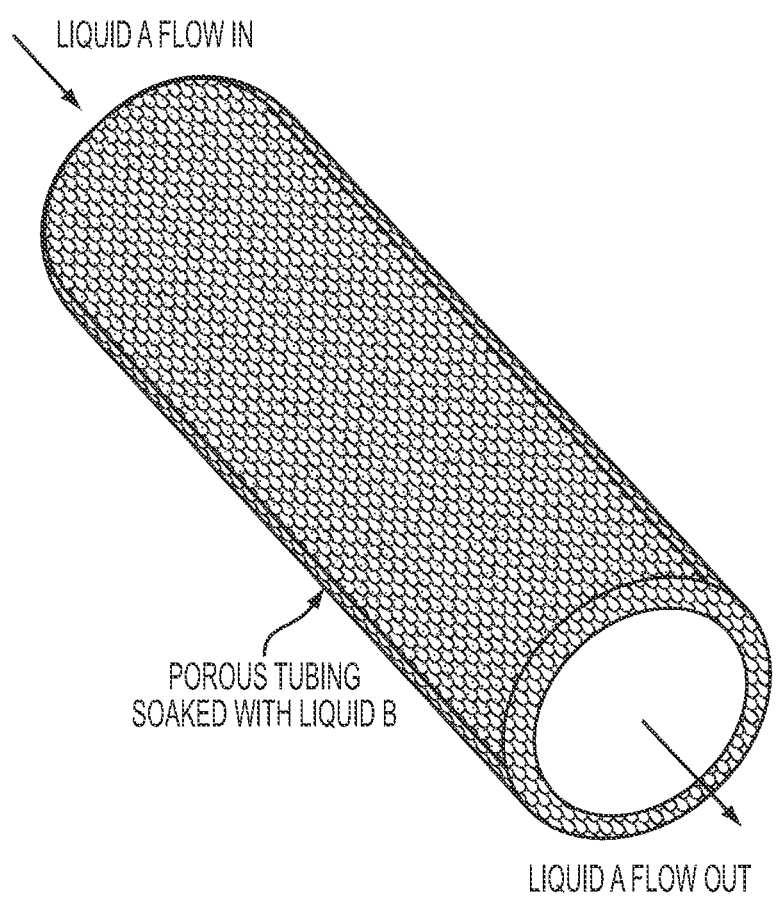
FIG. 7E shows SLIPS formed on the Liquid-B-soaked porous tubing and the like in accordance with certain embodiments.

SLIPS have properties that are insensitive to the precise geometry of the underlying substrate. Therefore, the geometry of the substrate can be any shape, form, or configuration to suit various-shaped materials and devices. In certain embodiments, the porous surface can be manufactured over any suitable materials and geometries, such as medical devices, inside of pipes (e.g., metallic or metallized pipes), optical windows, biological sensor windows, medical tubing, hollow metallic structures, patterned electrodes, meshes, wires, porous conductive surfaces, and the like that come into contact with biological materials. Some exemplary shapes over which the porous surface can be formed are shown in FIGS. 7A-E. Non-limiting examples of shapes, forms, and configurations SLIPS can take include generally spherical (e.g., bead, magnetic particles, and the like), tubular (e.g., for a cannula, connector, catheter, needle, capillary tube, tubing, or syringe) (see FIG. 7A(j)), planar (e.g., for application to a microscope slide, plate, film, or laboratory work surface) (see FIG. 7A(c)), or arbitrarily shaped (e.g., well, well plate, Petri dish, tile, jar, flask, beaker, vial, test tube, column, container, cuvette, bottle, drum, vat, or tank) (see FIG. 7A(a)-(b), (d)-(i)). For example, SLIPS can be applied to spherical surfaces, such as magnetic particles that can be actuated inside the body for drug delivery. FIG. 7B-E are perspective illustrations that show how SLIPS can be incorporated into a catheter tube. For example, FIG. 7B shows a SLIPS 700 attached to the outer surface of a cylindrical solid core 710 with a reservoir 720 for Liquid B. Alternatively, SLIPS can also be attached to the inner surfaces of the tubes, pipes, and other irregularly shaped substrates. For example, as shown in FIG. 7C, SLIPS 700 can be can be applied to the inner surface of a cylindrical tube 710 for low drag flow of Liquid A 730. In addition, as shown in FIG. 7D, SLIPS can be applied onto both the inner and outer surfaces of a tube/needle for low drag flow of Liquid A and remain slippery/non-sticking to the outside environments where the tube/needle is exposed to. Also, as shown in FIG. 7E, SLIPS can be applied onto a Liquid-B-soaked porous tubing for low drag flow of Liquid A and remain slippery/non-sticking to the outside environments where the porous tube/needle is exposed to.

Figure 5A:
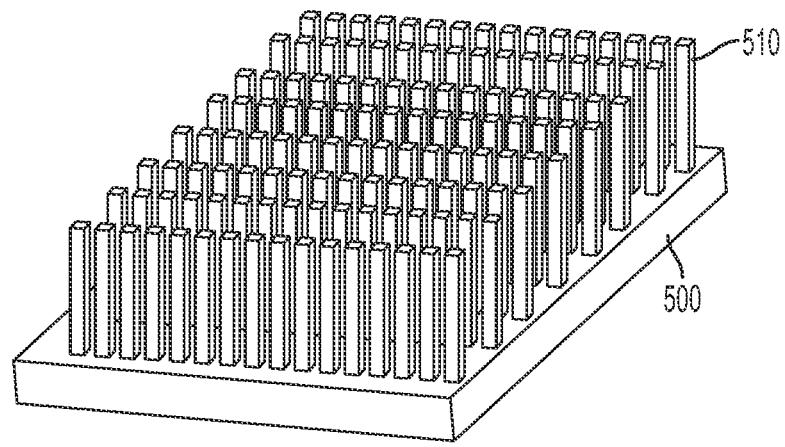
FIG. 5A is a schematic of a structured surface with raised features over which the slippery surface is formed in accordance with certain embodiments.
Figure 5B:
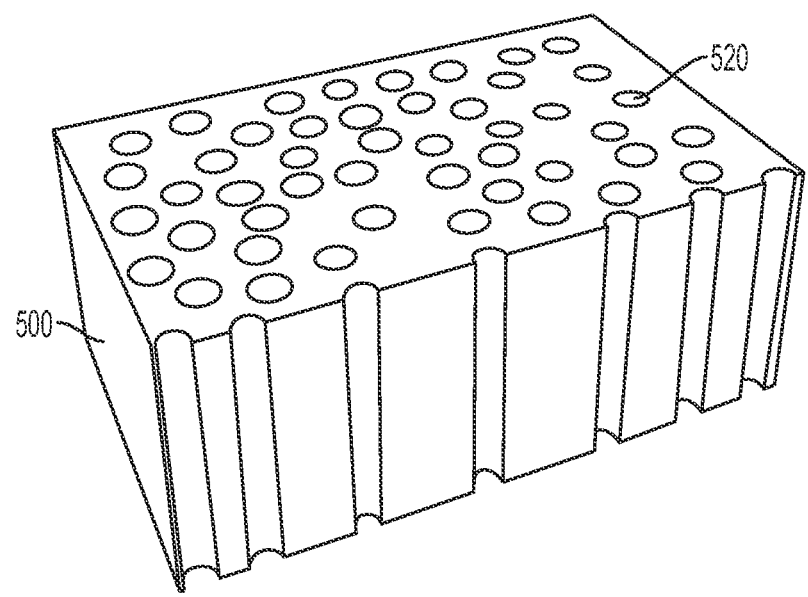
FIG. 5B is a schematic of a columnar porous material over which the slippery surface is formed in accordance with certain embodiments.
Figure 10:
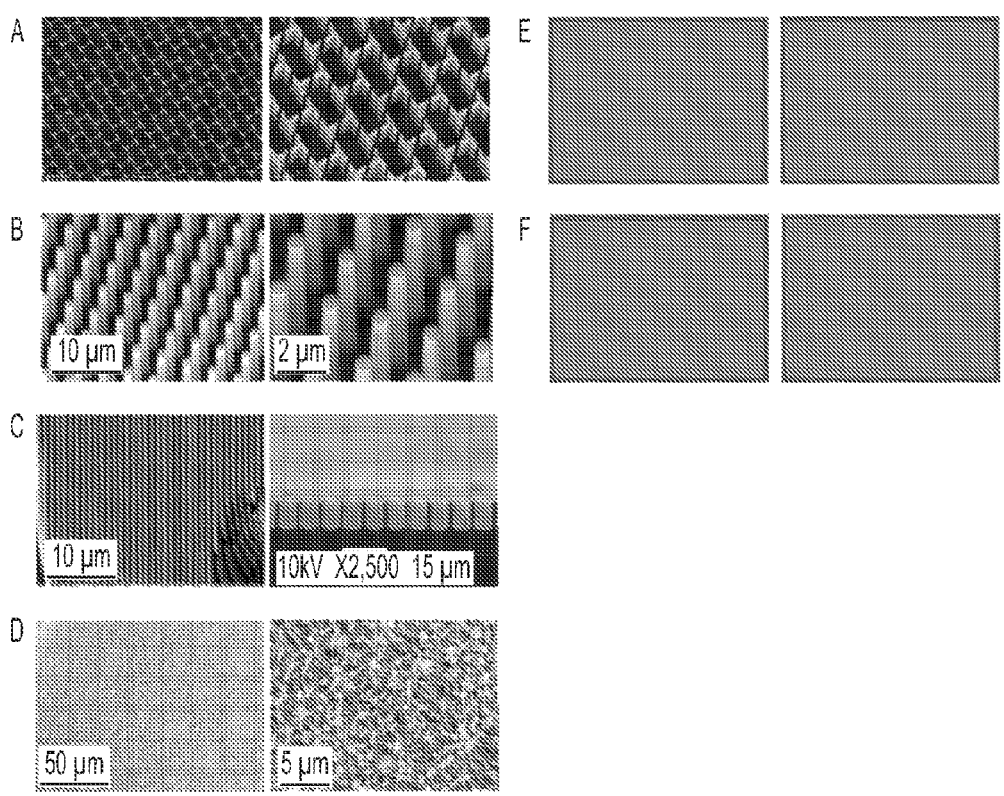
FIG. 10 shows images of substrate structures and topologies that can be used to generate SLIPS surfaces; (A) open-cell bricks, (B) post arrays, (C) parallel grooves, (D) open porosity PTFE (ePTFE), (E) plasma-etched PTFE, and (F) sand-blasted polypropylene (PP).

FIG. 5A to FIG. 5D show some exemplary roughened surfaces. In one embodiment, the roughened surface is formed over a two-dimensionally flat surface 500 by providing certain raised structures 510 or protrusions (see FIG. 5A). In another embodiment, the roughened surface is formed by forming pores 520 over a two-dimensionally flat surface 500 to yield a porous material (see FIG. 5B). Pores can take any geometry and can have pathways, columns (as illustrated in FIG. 5B or more random pathways. In yet another embodiment, a three-dimensionally interconnected network of regular or random pores is used (see FIG. 5C and FIG. 5D). FIG. 10 shows images of substrate structures and topologies that can be used to generate SLIPS surfaces; (A) open-cell bricks, (B) post arrays, (C) parallel grooves, (D) open porosity PTFE (ePTFE), (E) plasma-etched PTFE, and (F) sand-blasted polypropylene (PP).

A range of surface structures with different feature sizes and porosities can be used. Feature sizes can be in the range of hundreds of nanometers to microns (e.g., 100 to 1000 nm), and have aspect ratios from about 1:1 to 10:1. Porous nano-fibrous structures can be generated in situ on the inner surfaces of metallic microfluidic devices using electrochemical deposition using techniques known in the art (Aizenberg, J., Kim, P. Hierarchical Structured Surfaces Resistant to Wetting by Liquids. United States Provisional Patent, Application No. 61/353,505, filed on Jul. 19, 2010; Kim, P., Epstein, A. K., Khan, M., Zarzar, L. D., Lipomi, D. J., Whitesides, G. M., Aizenberg, J. Structural Transformation by Electrodeposition on Patterned Substrates (STEPS): A New Versatile Nanofabrication Method", *Nano Letters*, in press (2011)).

In certain embodiments, the surface has a large surface area that is readily wetted by the lubricating fluid and which entrains lubricating fluid and retains it on the substrate surface. In certain embodiments, the substrate surface is a hierarchical surface containing surface features on multiple dimension scales. By way of example, the surface can have a first topological feature having dimensions on the microscale and a second topological feature on the nanoscale. The first topological feature supports the second smaller topological feature. The second topological features are referred to as "primary structures" as they are meant to denote the smallest feature sizes of the hierarchical structure. The primary structures can include structures, such as nanofibers, nanodots, and the like. Such nanoscale "primary structures" can have at least one kind of feature sizes that are a few to tens or hundreds of nanometers in size, such as less than 5 nm to 200 nm. For example, nanofibers having diameters of approximate 5, 10, 25, 50, or even 100 nm. In such cases, when "primary structures" having feature sizes of about 100 nm diameter is utilized, "secondary structures" having feature sizes that are larger than 100 nm, such as 150 nm, 300 nm, 500 nm, or 1000 nm, and larger. Additional higher order structures, such as "tertiary structures" and the like, which each has larger feature sizes than the lower order structures are contemplated.

Particularly, hierarchical structures having nanofibers as the primary structures may provide a high degree of three-dimensional porosity that may be well-suited for use as porous surfaces described herein. A detailed discussion of hierarchical surfaces suitable for use with a liquid to be repelled is found in International Application No. PCT/US11/44553 entitled "Hierarchically structures surfaces to control wetting by liquids," filed on Jul. 19, 2011, which is incorporated in their entirety by reference.

In certain embodiments, the roughened surface may have a periodic array of surface protrusions (e.g., posts, peaks, etc.) or any random patterns or roughness (see, e.g., FIG. 5A). In some embodiments, the size of the features producing a roughened surface range from 10 nm to 100 µm with geometries ranging from regular posts/open-grid structures to randomly oriented spiky structures. In some embodiments, the widths of the raised structures are constant along their heights. In some embodiments, the widths of the raised structures increase as they approach the basal surface from the distal ends. The raised structures can be raised posts of a variety of cross-sections, including, but not limited to, circles, ellipses, or polygons (such as triangles, squares, pentagons, hexagons, octagons, and the like), forming cylindrical, pyramidal, conical or prismatic columns. Although the exemplary substrates described above illustrate raised posts having uniform shape and size, the shape, orientation and/or size of raised posts on a given substrate can vary.

Figure 33:
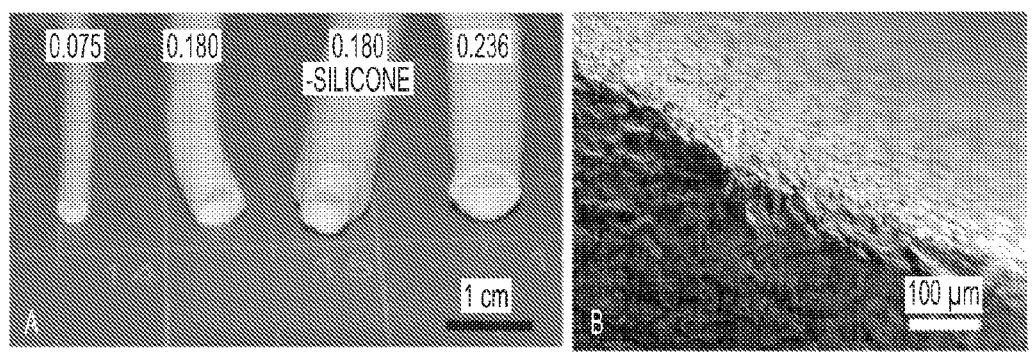
FIG. 33 shows images of ePTFE tubing (Zeus Inc) of increasing inner diameter (ID), from 0.075" to 0.236" (wall thickness is ~0.040" for all) fit with an elastic, external, silicone tube casing (VWR) in low (A) and high magnification SEM of the porous ePTFE surface within the tubing (B).
Figure 34:
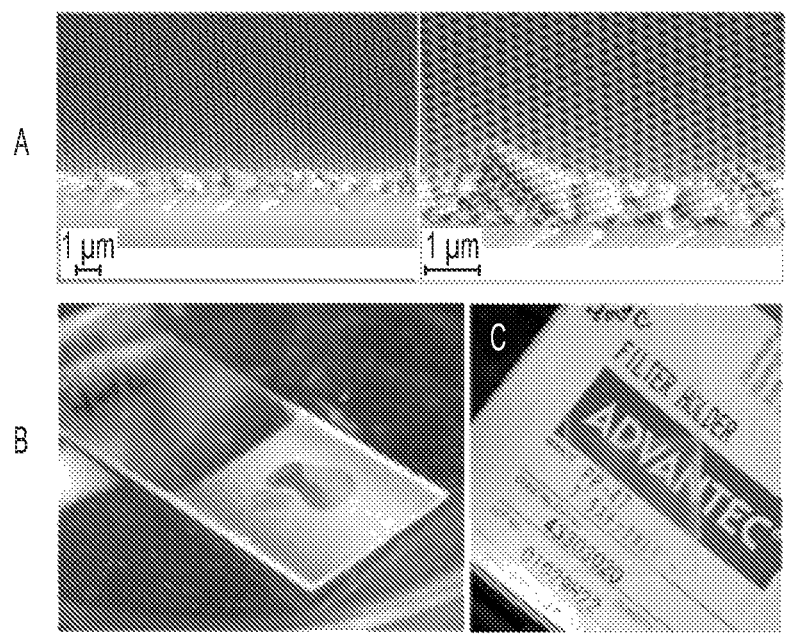
FIG. 34 shows images of a transparent SLIPS surface, based on the infiltration of a highly-ordered nanoporous $SiO_2$ glass layer (A) with perfluorocarbon (FC-70) (B). When fully infiltrated the layer is highly transparent (C) and well suited for applications as a bio-sensor window.

Open porosity PTFE (ePTFE) membranes can be pressed or molded to take on a variety of shapes, as is illustrated in FIGS. 35A-C and FIG. 33). FIG. 35 shows images of a process for fabricating a SLIPS tubing from ePTFE membranes in which (A) A tubular structure (center) is formed from two flat ePTFE membranes (1.0 µm pore size) by being pressed between two U-shaped channel molds (left and right). (B) One ePTFE membrane is pressed between the negative and positive molds, producing an indented channel structure for fluidic flow. This structure was then covered and bound to a flat ePTFE membrane to construct the SLIPS U-shape tube shown in (A). Low (left) and high (right) magnification views of scanning electron microscope (SEM) images (C) of a cross-section of the pressed ePTFE membrane; porous fibrous structure is visible at the right. FIG. 33 shows images of ePTFE tubing (Zeus Inc) of increasing inner diameter (ID), from 0.075" to 0.236" (wall thickness is ~0.040" for all) (A). The commercially available tubing is made by expanding PTFE tubing during the manufacturing process to create microscopic pores in the structure of the material. The 0.180" ePTFE tubing (which provides a porous microtexture to the substrate) can be fit with an elastic, external, silicone tube casing (VWR), for example, to provide a fluid flow barrier and/or to facilitate peristaltic pumping. High magnification SEM of the porous ePTFE surface within the tubing is also shown (B).

In certain embodiments, the roughened surface has a roughness factor, R, greater than 1, where the roughness factor is defined as the ratio between the real surface area and the projected surface area. For complete wetting of lubricating fluid to occur, it is desirable to have the roughness factor of the roughened surface to be greater or equal to that defined by the Wenzel relationship (i.e., $R \geq 1/\cos \theta$, where $\theta$ is the contact angle of lubricating fluid on a flat solid surface). For example, if lubricating fluid has a contact angle of 50° on a flat surface of a specific material, it is desirable for the corresponding roughened surface to have a roughness factor greater than ~1.5.

The roughened surface material can be selected to be chemically inert to the lubricating fluid and to have good wetting properties with respect to lubricating fluid. In addition, the roughened surface topographies can be varied over a range of geometries and size scale to provide the desired interaction, e.g., wettability, with lubricating fluid.

In certain embodiments, the micro/nanoscale topographies beneath the lubricating fluid enhance the liquid-wicking property and the adherence of lubricating fluid to the roughened surface. As a result, the lubricating fluid can uniformly coat the roughened surface and get entrapped inside at any tilting angles.

Non-limiting examples of porous materials include solid substrates having holes (e.g., high aspect ratio holes, cylinders, columns, etc.), three-dimensionally interconnected network of holes and one or more materials (e.g., 3-D ordered colloidal assemblies, block copolymers, etc.), and random array of fibrous materials (e.g., filter paper, fabrics, electrospun films).

Non-limiting examples of porous or rough surface structures that can be used include polymers (e.g., polysulfone, PDMS, and polypyrrole) and hydrophobic porous (e.g., Teflon) materials. For example, the roughened surface can be manufactured from polymers (e.g., epoxy, polycarbonate, polyester, nylon, etc.), metals, sapphire, glass, carbon in different forms (such as diamond, graphite, black carbon, etc.), ceramics (e.g., alumina), and the like. For example, fluoropolymers such as polytetrafluoroethylene (PTFE), polyvinylfluoride, polyvinylidene fluoride, fluorinated ethylene propylene, and the like can be used as substrates. Many porous materials are commercially available, or can be made by a number of well-established manufacturing techniques. For example, polytetrafluoroethylene (also known by the trade name "Teflon" and abbreviation "PTFE") filter materials are commercially available. In some embodiments, the roughened surface is manufactured from a hemocompatible material, non-limiting examples of which include silicon rubber and polysulfones. In certain embodiments, the roughened surface is manufactured from any suitable materials. In certain embodiments, if the desired material and shape is not electrically conducting, the surfaces of such material and shapes can be rendered electrically conductive by applying a thin layer of conductive material, such as through vapor deposition techniques, sputtering, metallization techniques, and the like. Moreover, the porous surface can be readily formed on large surface area materials that are commercially important. When necessary, surface functionalization can be carried out to modify the solid surfaces so that the lubricating layer preferentially wets the roughened surface as compared to Liquid A.

The raised structures can be produced by any known method for fabricating raised structures onto substrates. Non-limiting examples include molding into the device structure, conventional photolithography, projection lithography, e-beam writing or lithography, depositing nanowire arrays, growing nanostructures on the surface of a substrate, soft lithography, replica molding, solution deposition, solution polymerization, electropolymerization, electrospinning, electroplating, vapor deposition, contact printing, etching, bead blasting, sand blasting, transfer patterning, microimprinting, self-assembly, and the like.

In certain embodiments, the roughened surface can be made, for example, by replica molding procedure described in B. Pokroy, A. K. Epstein, M. C. M. Persson-Gulda, J. Aizenberg, *Adv. Mater.* 21, 463 (2009), the contents of which is incorporated by reference herein in its entirety. Patterned surfaces can also be obtained as replicas (e.g., epoxy replicas) by a soft lithographic method (see, e.g., J. Aizenberg and B. Pokroy, PCT/US2009/048880, the contents of which is incorporated by reference herein in its entirety). Polymer films with patterned surfaces can be fabricated by means known in the art (e.g., roll-to-roll imprinting or embossing). By way of non-limiting example, negative replicas of pre-generated patterns can be made from polydimethylsiloxane, PDMS (e.g., Dow-Sylgard 184) by pouring mixture of prepolymer and curing agent (e.g., 10:1 ratio) on the patterns followed by thermal curing in an oven. After cooling, the negative PDMS mold can be peeled off and used for fabricating the final replica by pouring the desired material (e.g. UV-curable epoxy resin) into the negative mold. After solidifying the material, the negative mold can be peeled off, leaving the replica of the original pattern. Then, the surface of the replica can be chemically functionalized with low surface energy coating such as (tridecafluoro-1,1,2,2-tetrahydrooctyl)-trichlorosilane.

For example, a silicon substrate having a post array such as is illustrated in FIG. 5A can be fabricated by photolithography using the Bosch reactive ion etching method (as described in Plasma Etching: Fundamentals and Applications, M. Sugawara, et al., Oxford University Press, (1998), ISBN-10: 019856287X, the contents of which is incorporated by reference herein in its entirety).

Arrays of hydrophobic raised surface structures can be made at the micrometer scale using micromolding techniques. For example, rough surface structures can be arrays of hydrophobic raised surface structures at the micrometer scale, such as posts and intersecting walls patterned in polymers such as epoxy (FIG. 10A-C).

Figure 5C:
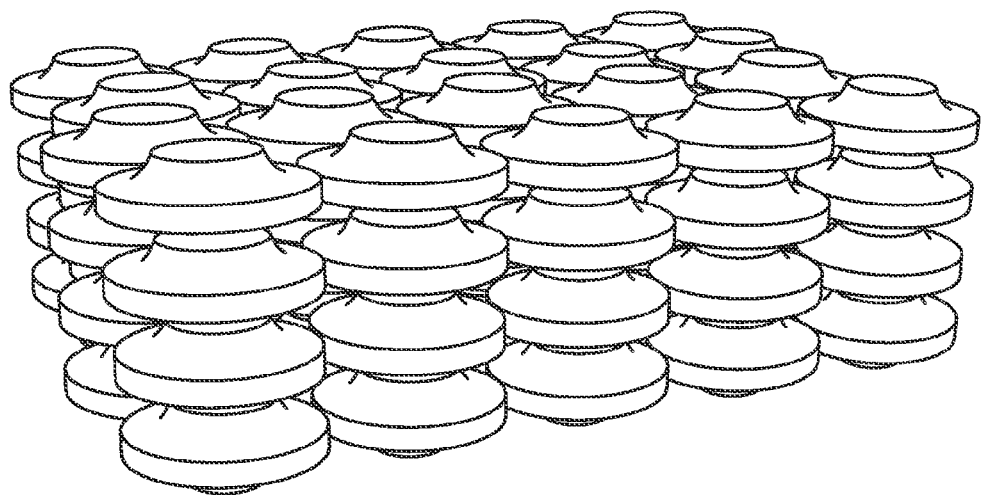
FIG. 5C is a schematic of an inverse opal porous material over which the slippery surface is formed in accordance with certain embodiments.
Figure 5D:
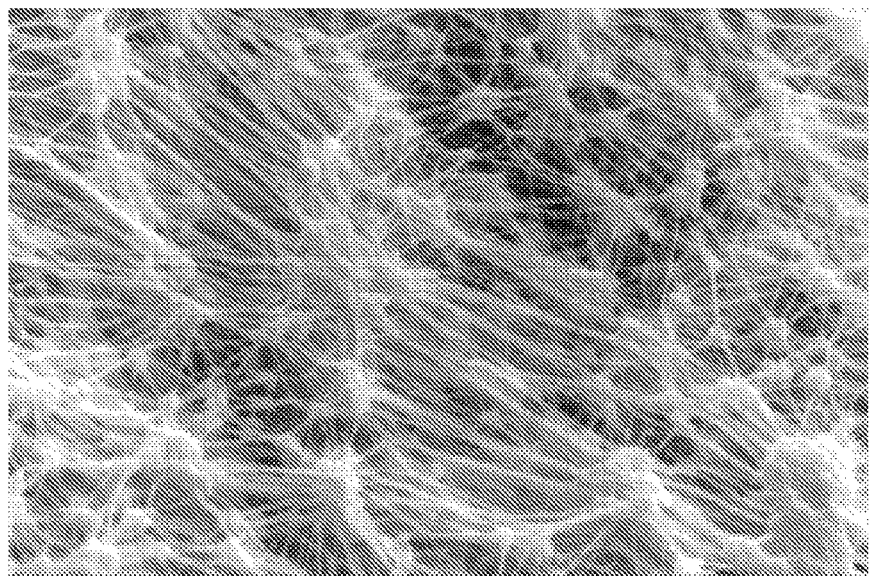
FIG. 5D is an image of a random network porous material over which the slippery surface is formed in accordance with certain embodiments.

In certain embodiments, the roughened surface may be the surface of a three-dimensionally porous material (see, e.g., FIG. 5B to FIG. 5D). The porous material can be any suitable porous network having a sufficient thickness to stabilize lubricating fluid, such as a thickness from about 5 µm to about 1 mm. Moreover, the porous material can have any suitable pore sizes to stabilize the lubricating fluid, such as from about 10 nm to about 100 µm.

In another embodiment, porous alumina is manufactured by the process of anodization as shown in FIG. 5B, where an aluminum substrate is electrochemically oxidized under constant electrical potential. The pore size, inter-pore spacing, and aspect ratio of the pores can be tuned by adjusting the operating parameters of the electrochemical oxidation process. Such a process generates porous through-holes into the substrate, where the size of the porous holes are on the order of 50 nm with aspect ratio larger than 10000 (see, Lee et al., *Nature Mater.* 5, 741-47, 2006, the contents of which is incorporated by reference herein in its entirety.).

In some embodiments, mechanical or (electro)chemical methods can be used to roughen metal surfaces. Roughening and non-wetting materials can be spray coated directly onto metal surfaces. Boehmite (γ-AlO(OH)) formation on aluminum surface by boiling in water can also be used to roughen metallic surfaces such as aluminum. Rotary jet spinning of hydrophobic polymer nanofibers and layered deposition of an appropriate primer can also be used to roughen substrates for use in SLIPS.

In yet another embodiment, long range ordered porous structures of silica, as shown in FIG. 5C, can be produced by evaporative co-assembly method of sacrificial polymeric colloidal particles together with a hydrolyzed silicate sol-gel precursor solution. Such a method generates a crack-free porous surface on the order of centimeters or larger, with pore sizes of about 100 nm to about 1000 nm and porosity of about 75%. (See, Hatton, et al., *Proc. Natl. Acad. Sci.* 107, 10354-10359, 2010 and U.S. patent application Ser. No. 13/058,611, filed on Feb. 11, 2011, the contents of which is incorporated by reference herein in its entirety.).

Referring to FIG. 5D, polymer-based porous membrane (such as medical grade PTFE) can be made by mixing PTFE powders with lubricating fluid to form a paste. Then, the paste can be molded into the desired shape by methods such an extrusion molding. The molded PTFE membrane can then be heated up to less than its melting point to drive off the lubricants. Thereafter, a porous PTFE membrane can be formed (see U.S. Pat. No. 5,476,589, the content of which is incorporated by reference herein in its entirety).

In yet another embodiment, the porous material can be generated in-situ on a metal surface by an electrodeposition method, such as the STEP method (STEP=structural transformation by electrodeposition on patterned substrates, see, PCT Application No. PCT/US11/44553, filed on Jul. 19, 2011, and Kim, et al., *Nano Lett.*, in press, (2011), the contents of which are incorporated by reference herein in their entirety. The electrodeposition condition can be controlled so that nanofibers of electrically conductive polymer can be formed over an electrically conductive surface. The electrodeposition conditions can further be controlled to provide a desired nanofiber diameter and spacing. In certain embodiments, the electrodeposition condition can be controlled to provide any other desirable morphology that can provide additional means to stabilize the lubricating layer.

Figure 24A:
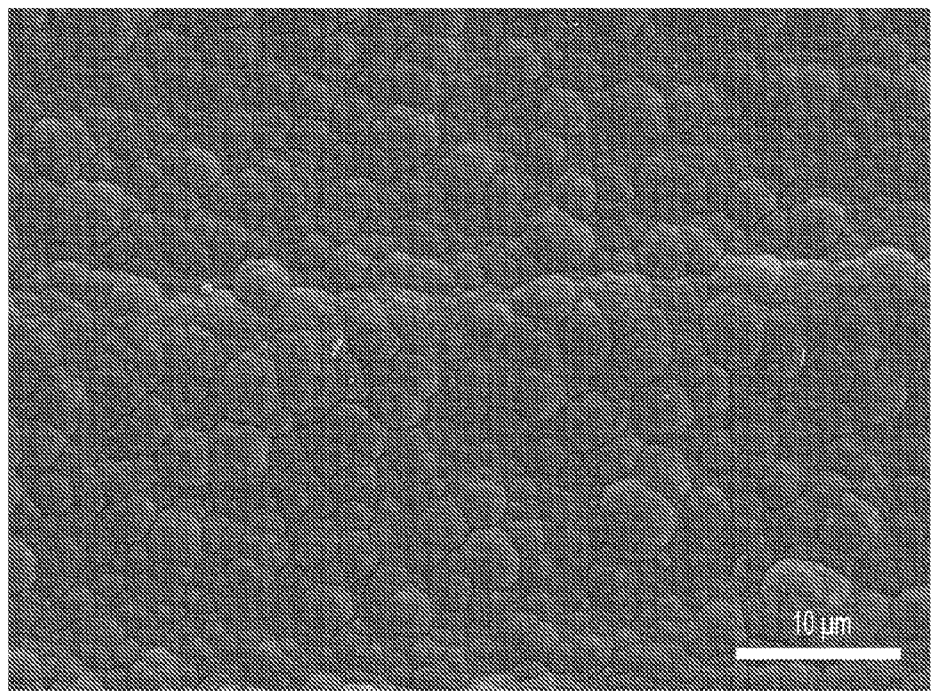
FIGS. 24A to 24E show the different morphologies that can arise by changing the electrodeposition parameters in accordance with certain embodiments.
Figure 24B:
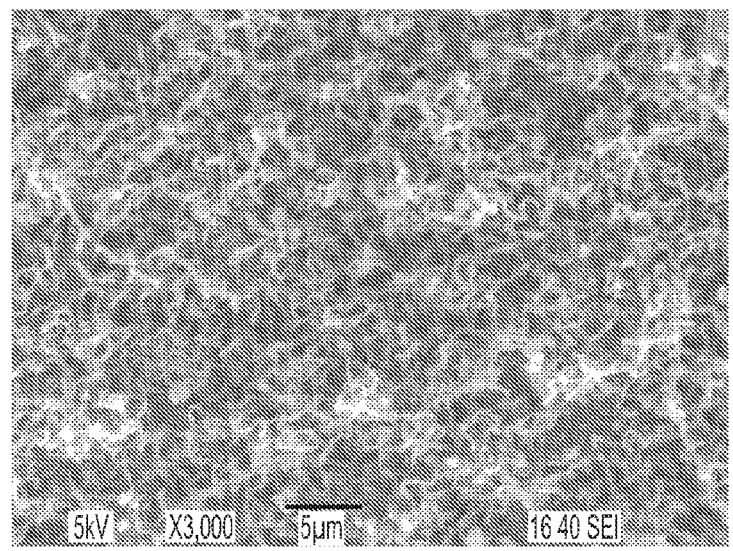
Figure 24C:
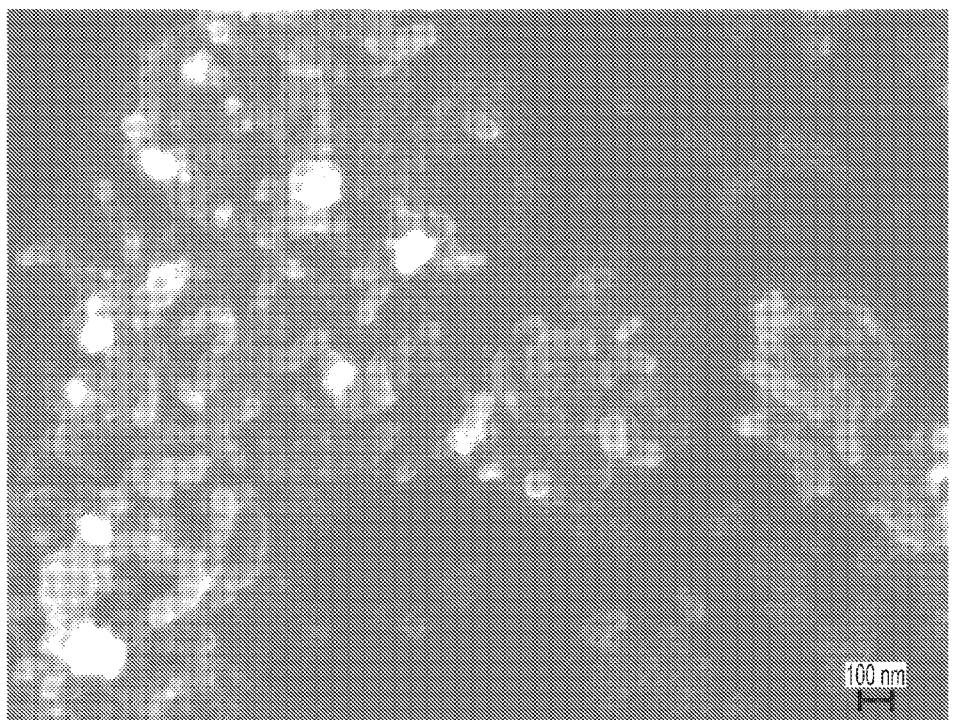
Figure 24D:
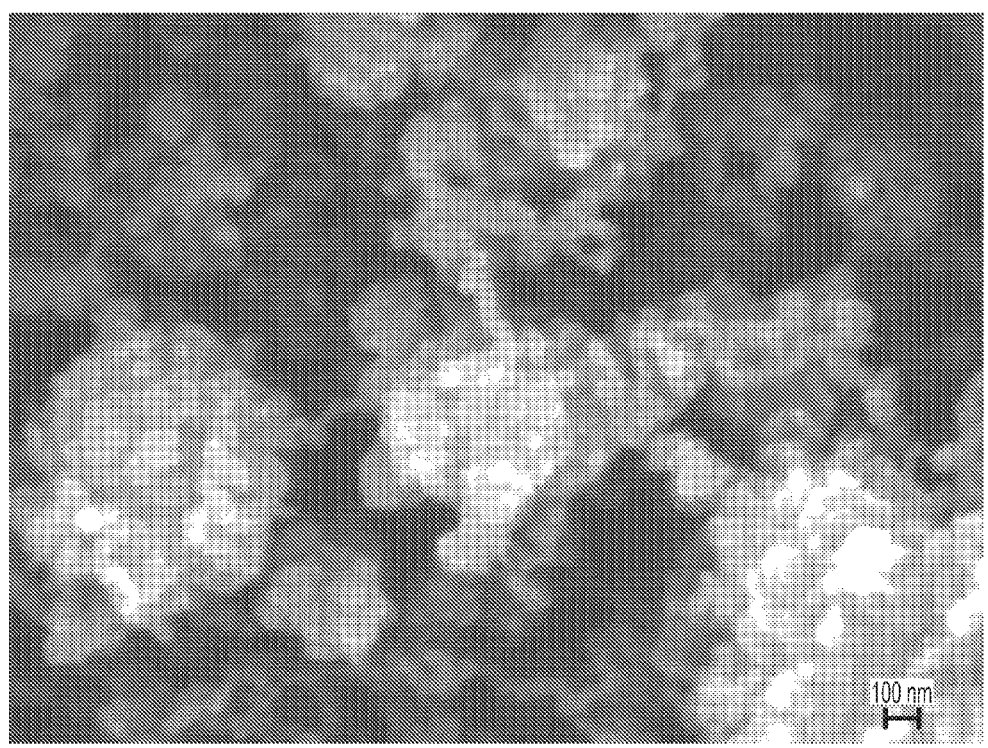
Figure 24E:
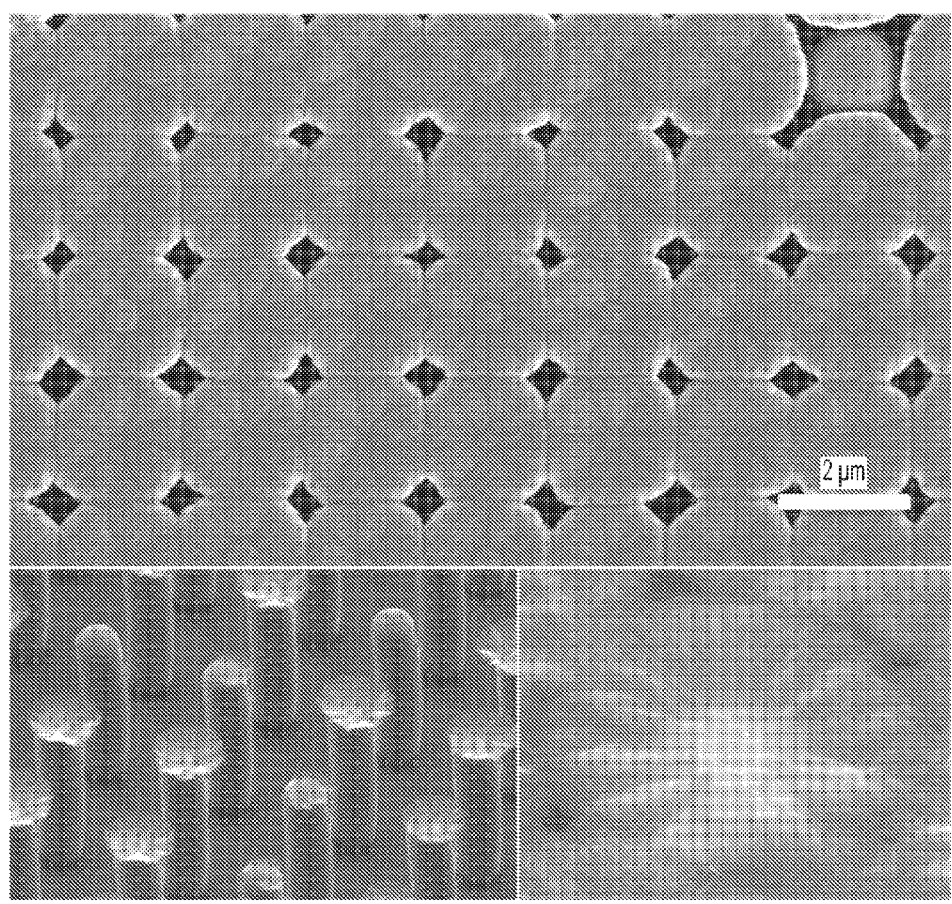
Figure 25:
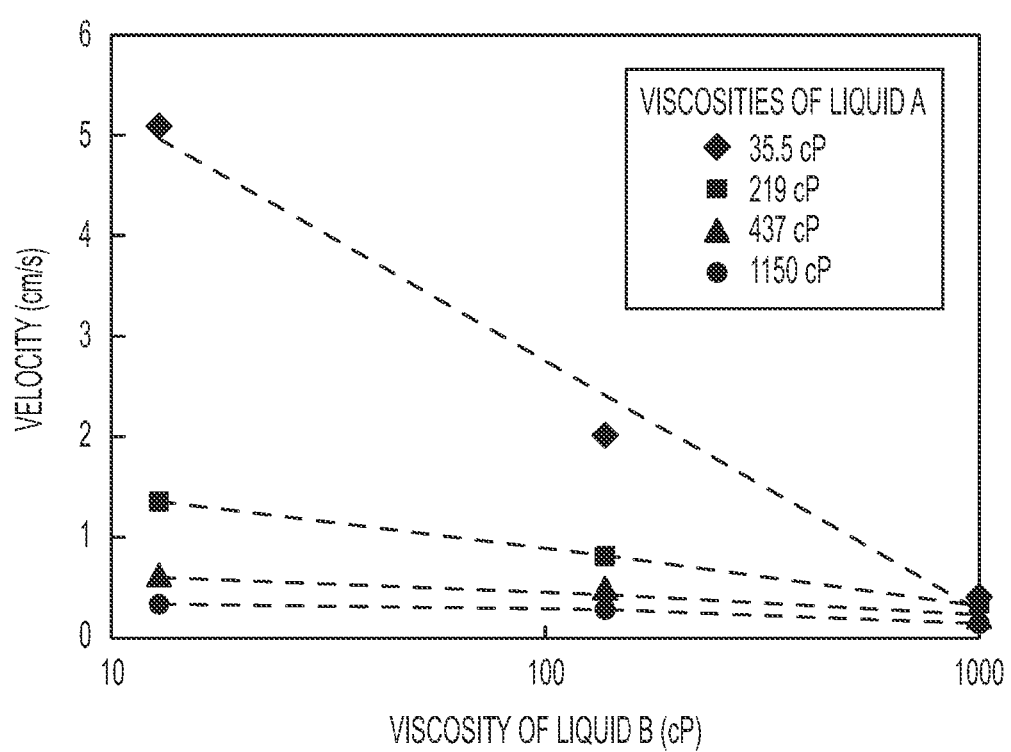
FIG. 25 is a graph showing the dependence of liquid repellency of SLIPS on the viscosity of Liquid B (here, Krytox 100, 103, and 105 (DuPont)). For constant viscosity of Liquid A (here, 25 μL of glycerol), Liquid A's mobility increases as the viscosity of Liquid B decreases. Likewise, for constant viscosity of Liquid A, the mobility of Liquid A increases with reducing viscosity. Thus viscous dissipation plays a major role in the liquid mobility on SLIPS.

The morphology of the conducting organic polymers can be controlled by varying the deposition conditions such as the concentration of monomer, the types of electrolytes and buffers, the deposition temperature and time, and the electrochemical conditions such as applied potential. For example, increasing the concentration of monomer in the electrochemical solution, the applied potential, and/or the temperature generally leads to a faster polymerization rate and many parasitic nucleation sites during growth resulting in a morphology that is similar to a cauliflower (see FIG. 24A). In contrast, lower concentrations of monomer, lower applied potential, and lower temperatures can lead to nanofibrile growth with substantially uniform diameters (see FIG. 24B). Further decrease in concentration of monomer or applied potential can lead to short rods of polymer nanofibers with low surface coverage (see FIG. 24C). In another example, increasing the type of electrolytes and buffers to obtain a more acidic solution can lead to the formation of a cauliflower shape (see FIG. 24A) or overgrowth of polymers (see FIG. 24D). In another example, the applied voltage can be cycled leading to different oxidation states of the deposited polymer layer which is often manifested as a color change (e.g., from dark blue to a green then to a pale yellow color with increasing applied voltage). In yet another example, the applied voltage can be pulsed at a constant voltage to form polymers only on the tip of the underlying micropost structures, leading to a mushroom-like morphology (see FIG. 24E). Accordingly, the morphology of conducting organic polymers can be finely controlled from nanometers to over micrometer scales, and surface coatings with precisely controlled morphology can be produced by simple modifications, which promise the customization of various surface properties by design and control of the morphology.

In other embodiments, a roughened surface is further functionalized to improve wetting by lubricating fluid. Surface coating can be achieved by methods well known in the art, including plasma assisted chemical vapor deposition, chemical functionalization, solution deposition, and vapor deposition. For example, surfaces containing hydroxyl groups (i.e., —OH) can be functionalized with various commercially available fluorosilanes (e.g., tridecafluoro-1, 1,2,2-tetrahydrooctyl-trichlorosilane, heptadecafluoro-1,1, 2,2-tetra-hydrodecyl trichlorosilane, etc.) to improve wetting by low surface tension fluids. In certain embodiments, many materials having native oxides, such as silicon, glass, and alumina, can be activated to contain —OH functional groups using techniques such as plasma treatment. After activation, either vapor or solution deposition techniques can be used to attach silanes so that surfaces with low surface energy can be produced. For vapor deposition, the deposition can be carried out by exposing the surface to silane vapors. For solution deposition, the deposition can be carried out by immersing the surface in a silane solution, followed by rinsing and blow-drying after deposition. For layered deposition, layered deposition of a primer is followed by application of a mixture of sacrificial beads and Liquid B, which is dried and cured. The beads are removed to produce a contiguous porous Teflon-like surface.

In some other embodiments, where hydroxyl groups is absent on the surface, the surface can be functionalized by first coating it with thin films of metals, such as gold or platinum, and the thin metal films can be functionalized with various commercially available thiols of low surface energy (e.g., heptane thiol, perfluorodecanethiol, etc.). Similarly, vapor or solution deposition techniques can be carried out similar to that describe for silane deposition using, for example, alkane thiol solutions.

Figure 2:
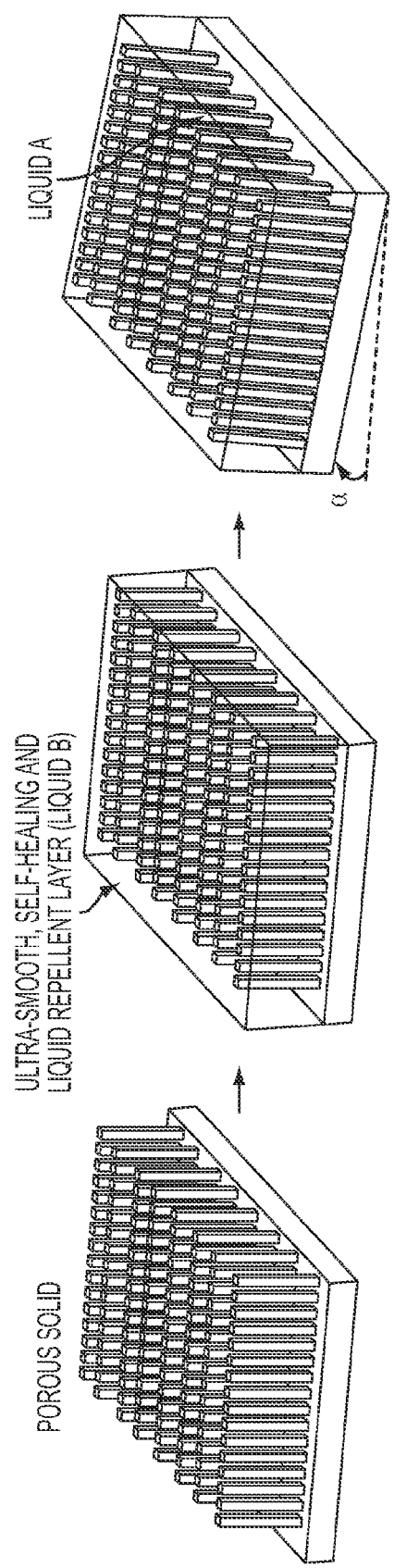
FIG. 2 is a schematic of a self-healing slippery surface in accordance with certain embodiments.
Figure 14:
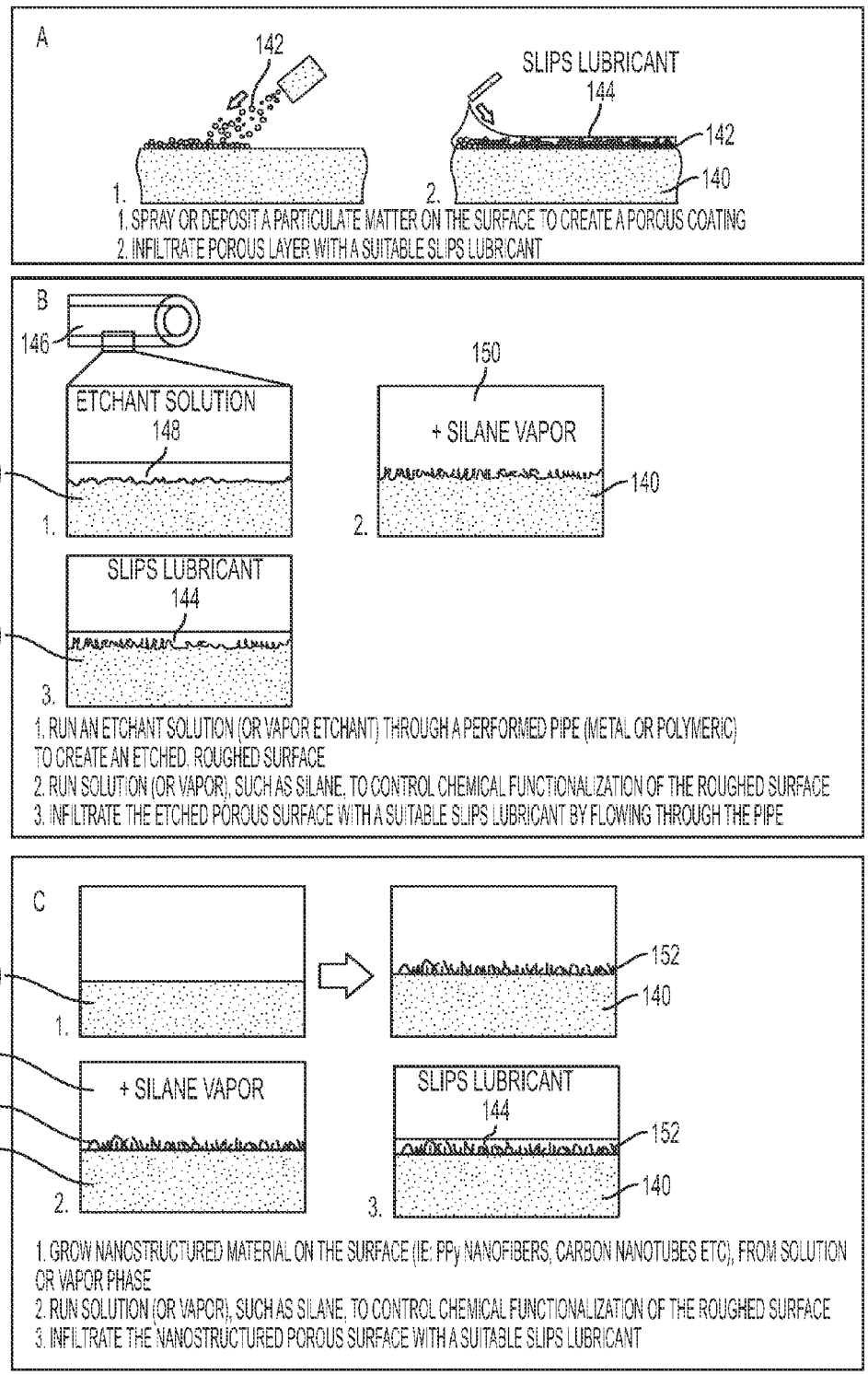
FIG. 14 is a series of diagrams that show exemplary methods by which SLIPS surfaces can be roughened: by spraying or depositing a particulate matter on the substrate (14A); etching (14B); and by growing a nanostructured material on the surface of the substrate (14C).

In another embodiment, the roughened, porous substrate can be generated by a spraying method, where emulsions consisting of micro/nanoparticles are sprayed onto a flat solid surface (FIG. 14A1). These particles assemble into roughened solid layer upon solvent drying. Such a solid layer can then be infiltrated by lubricating fluid (FIG. 14A2) (which can also be applied by additional spraying). FIG. 14A shows a surface roughened by a spray method. Here, the substrate 140 is roughened by spraying or depositing a particulate matter 142 on the substrate 140 to create a porous coating (A1) and the roughened surface is infiltrated with lubricating liquid 144. Non-limiting examples of micro/nanoparticles that can be sprayed onto a flat solid surface to form roughened, porous material include titanium dioxide, silicon dioxide, nanodiamonds, metals such as silver, gold, platinum, copper, gold, palladium, zinc, and titanium, hydroxyapatite (HAp) nanoparticles.

In one or more embodiments, the roughened, porous substrate is generated by chemical or physical etching, which includes mechanical roughening such as bead blasting and sand blasting. Referring to FIG. 14B, the substrate 140 is roughened by etching (B1). The etchant 148 is carried by a preformed pipe 146 and deposited onto the substrate 140 to create a roughened surface. Once the surface is roughened, it is functionalized (B2) with a liquid (not shown) or vapor silane 150, and infiltrated with a lubricating liquid 144 (B3).

Figure 3:
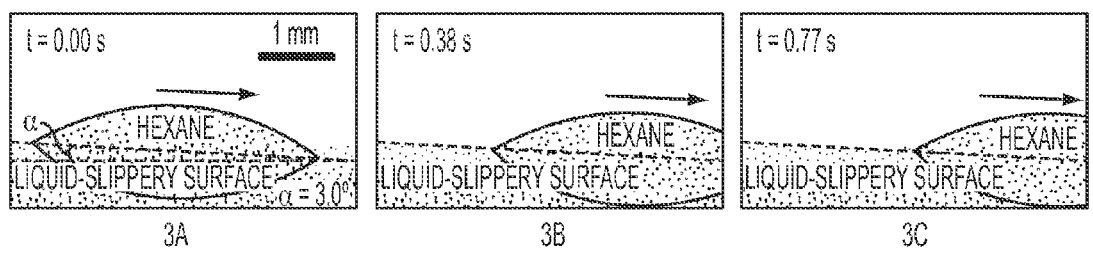
FIG. 3A-C shows time sequence images on the sliding motion of a droplet of hexane ($\gamma_{liquid}$=18.6±0.5 mN/m, volume ~3.6 µL) along a SLIPS at low sliding angle (α=3.0°) in accordance with certain embodiments.

In other embodiments, the roughened, porous substrate is made by growing a nanostructured material on the surface. In FIG. 14C, a nanostructured material 152 is grown on the surface of the substrate 140 to create a roughened surface (C1) that is functionalized (C2)) with a liquid (not shown) or vapor silane 150 and infused with a lubricating liquid 144 (C3). Non-limiting examples of these nanostructures include PPy nanofibers, carbon nanotubes, and the like. One the nanostructures are in place, the surface can be chemically functionalized by silanization (FIG. 14C2) and infiltrated with a lubricating liquid (FIG. 14C3).

In certain embodiments, the roughened surface can be formed over or applied to a variety of planar or non-planar surface (see FIG. 7 and FIG. 8A-B). For example, FIG. 8B shows a porous membrane attached to the outer surface of a cylindrical solid core. It can also be attached to the inner surfaces, outer surfaces, or inner and outer surfaces of tubes and other irregularly shaped substrates.

In certain embodiments, the solid surface may be substantially flat. This situation may be applicable when the critical surface energy of the flat surface is higher than the surface tension of the functional lubricating fluid.

In certain embodiments, the roughened surface can have pores that are comparable or smaller than the material to be repelled. For example, pore sizes that are smaller than the size of protozoa (e.g., 10 μm), bacteria (e.g., 1 μm), viruses (e.g., 0.1 μm), and the like can be utilized.

In one or more of the above embodiments, non-limiting examples of surface to which SLIPS is applied include a cannula, connector, catheter (e.g., central line, peripherally inserted central catheter (PICC) line, urinary, vascular, peritoneal dialysis, and central venous catheters), catheter connector (e.g., Leur-Lok and needleless connectors), clamp, skin hook, cuff, retractor, shunt, needle, capillary tube, endotracheal tube, ventilator, associated ventilator tubing, drug delivery vehicle, syringe, microscope slide, plate, film, laboratory work surface, well, well plate, Petri dish, tile, jar, flask, beaker, vial, test tube, tubing connector, column, container, cuvette, bottle, drum, vat, tank, organ, organ implant, or organ component (e.g., intrauterine device, defibrillator, corneal, breast, knee replacement, and hip replacement implants), artificial organ or a component thereof (e.g., heart valve, ventricular assist devices, total artificial hearts, cochlear implant, visual prosthetic, and components thereof), dental tool, dental implant (e.g., root form, plate form, and subperiosteal implants), biosensor (e.g., glucose and insulin monitor, blood oxygen sensor, hemoglobin sensor, biological microelectromechanical devices (bioMEMs), sepsis diagnostic sensor, and other protein and enzyme sensors), bioelectrode, endoscope (hysteroscope, cystoscope, amnioscope, laparoscope, gastroscope, mediastinoscope, bronchoscope, esophagoscope, rhinoscope, arthroscope, proctoscope, colonoscope, nephroscope, angioscope, thoracoseope, esophagoseope, laryngoscope, and encephaloscope) wound dressing (e.g., bandages, sutures, staples), and combinations thereof.

Lubricating Fluids (Liquid B)

Lubricating fluids are selected to create a fluid surface that is intrinsically smooth, stable, and defect free. The lubricating fluid should infiltrate, wet, and stably adhere to the substrate. Moreover, it should be chemically inert with respect to the solid substrate and the fluid to be repelled. In certain embodiments, a lubricating fluid possesses the ability to form a substantially molecularly flat surface when provided over a roughened surface. In certain other embodiments, a lubricating fluid possesses the ability to form a substantially atomically flat surface when provided over a roughened surface. In one or more embodiments, the lubricant is substantially incompressible.

Further, the lubricating fluid is capable of repelling immiscible fluids, and in particular biological fluids of any surface tension. For example, the enthalpy of mixing between the fluid to be repelled and lubricating fluids be may be sufficiently high (e.g., water and oil) that they phase separate from each other when mixed together. In certain embodiments, the lubricating fluid can be selected such that the fluid to be repelled has a small or substantially no contact angle hysteresis. For example, contact angle hysteresis less than about 5°, 2.5°, 2°, or even less than 1° can be obtained. Low contact angle hysteresis encourages sliding at low tilt angles (e.g., <5°), further enhancing fluid repellant properties of the surface.

The effectiveness of a given lubricating fluid's ability to repel fluids can be confirmed by visualization techniques known in the art including fluorescence microscopy and scanning electron microscopy (SEM).

Figure 4:
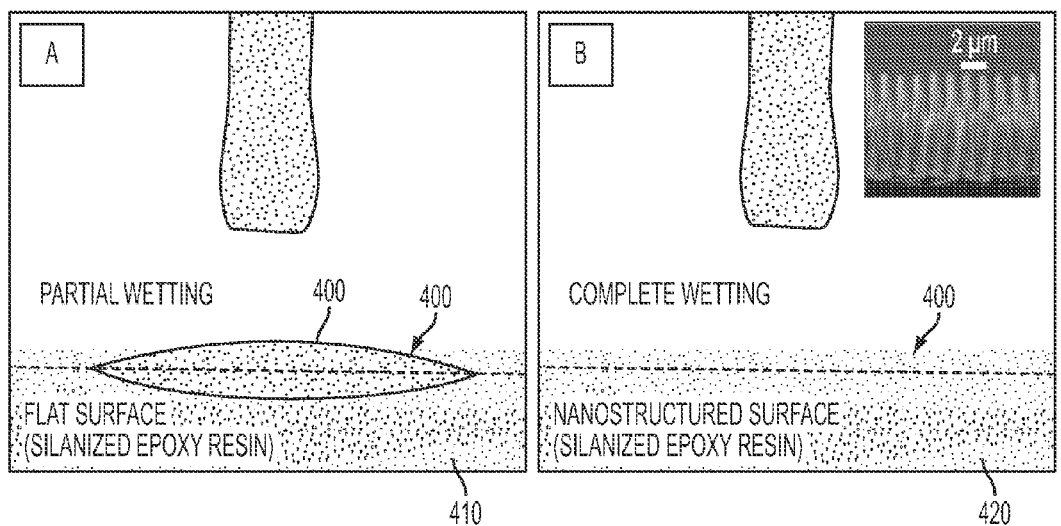
FIG. 4 is a schematic comparing the partial wetting of a flat surface (FIG. 4A) and the complete wetting of a nanostructured surface in accordance with certain embodiments (FIG. 4B).

In one or more embodiments, lubricating fluid is inert with respect to the solid surface and biological fluid. Lubricating fluid flows readily into the recesses of the roughened surface and generally possesses the ability to form an ultra-smooth surface when provided over the roughened surface. FIG. 4A shows a droplet 400 of perfluoro-tripentylamine (herein referred to by the trade name "FC-70") lubricating fluid on an unstructured surface 410 of a flat surface prepared from a slanted epoxy resin. The dashed line represents the location of the upper surface of the substrate. The droplet spreads out on the flat surface, but retains a droplet form. FIG. 4B shows the same lubricating fluid on an exemplary roughened surface of the same composition 420 having nanostructures, the features of which are shown in the inset. As shown, the nanostructures greatly enhance the wetting of the lubricating fluid on the surface, creating a uniformly-coated slippery functional layer over the topographies. The resulting ultra-smooth surface is capable of repelling fluids including, but not limited to biological fluids and particles in solution or suspension.

Lubricating fluid can be selected from a number of different fluids. These fluids can be selected based on their biocompatibility, low (or high) toxicity, anti-clotting performance, chemical stability under physiological conditions, and levels of leaching from the surfaces of the devices. For example, compounds that are approved for use in biomedical applications (e.g., blood substitutes, MRI contrast agents), such as perfluorinated hydrocarbons and organosilicone compounds (e.g. silicone elastomer) can be used as lubricating fluids. In one or more aspects, the lubricating fluid is a chemically-inert, high-density biocompatible fluid, non-limiting examples of which include tertiary perfluoroalkylamines (such as perfluorotri-n-pentylamine, FC-70, perfluorotri-n-butylamine FC-40, etc), perfluoroalkylsulfides and perfluoroalkylsulfoxides, perfluoroalkylethers, perfluorocycloethers (like FC-77) and perfluoropolyethers (such as KRYTOX family of lubricants by DuPont), perfluoroalkylphosphines and perfluoroalkylphosphineoxides, and combinations thereof are used. In addition, long-chain perfluorinated carboxylic acids (e.g., perfluorooctadecanoic acid and other homologues), fluorinated phosphonic acids, fluorinated silanes, and combinations thereof can be used as Liquid B. Perfluoroalkyls can be linear or branched.

In certain embodiments, the lubricating fluid has a high density. For example, the lubricating fluid has a density that is more than 1.0 g/cm³, 1.6 g/cm³, or even 1.9 g/cm³. In certain embodiments, the density of the lubricating fluid is greater than that of the biological fluid to enhance fluid repellency. High density fluids reduce the tendency of an impacting fluid to 'sink' below the surface of lubricating fluid and to become entrained therein. In certain embodiments, the density of Liquid A may be lower than that of the lubricating liquid. For example, density of Liquid A may be at least ~1.5 times lower than that of the lubricating liquid.

In certain embodiments, the lubricating fluid has a low evaporation rate, such as less than 100 nm/s, less than 10 nm/s, or even less than 1-2 nm/s. The lubricating fluid should be applied in a thickness sufficient to cover the rough surface of the substrate and provide an ultra-smooth surface. Taking a typical thickness of the lubricating fluid to be about 10 μm and an evaporation rate of about 1-2 nm/s, SLIPS can remain highly fluid-repellant for a long period of time without any refilling mechanisms.

In certain embodiments, lubricating fluid has a low freezing temperature, such as less than −5° C., −25° C., or even less than −50° C. Having a low freezing temperature allows lubricating fluid to maintain its slippery behavior to repel a variety of liquids or solidified fluids, such as ice and the like and over a range of temperatures.

Experimentally, it is observed that Object A can become highly mobile on the surface of the lubricating liquid when the kinematic viscosity of the lubricating liquid is less than 1 cm²/s. Since liquid viscosity is a function of temperature (i.e., liquid viscosity reduces with increasing temperature), choosing the appropriate lubricant that operates at the aforementioned viscosity (i.e., <1 cm²/s) at specific temperature range is desirable. Particularly, various different commercially available lubricating liquid can be found at the specified viscosity, such as perfluorinated oils (e.g., 3M™ Fluorinert™ and DuPont™ Krytox® oils), at temperatures ranging from less than −80° C. to greater than 260° C. For example, the temperature dependence of liquid viscosity of DuPont Krytox oils is shown in the Table 1 as a specific example (note: data is provided by the manufacturer of DuPont Krytox oils).

viscosities of 13 cP, 140 cP, and 990 cP are ~17 cm/s, ~5.8 cm/s, and ~0.98 cm/s, respectively. Therefore, to enhance the velocity of Liquid A on SLIPS, it is desirable to use a Liquid B having a lower viscosity. This general trend is consistent for Liquid A of viscosities ranging from 1 cP to 1000 cP.

Lubricating fluid can be deposited in any desired thickness, provided the top surface of lubricating fluid forms an ultra-smooth surface and is retained and interacts with the underlying surface. If the liquid layer is too thick, the upper surface is 'unbound' from the underlying surface and will flow with Liquid A from the SLIPS surface. The liquid layer that interacts with and is retained by the underlying surface is referred to as the 'characteristic thickness' of the liquid layer. The characteristic thickness will vary depending on the underlying surface and the ambient conditions, e.g., temperature, pressure, etc. Film thicknesses substantially on the order of the surface roughness peak-to-valley distance provide good fluid-solid interaction between the substrate and lubricating fluid. When the solid substrate is tilted at a position normal to the horizontal plane, lubricating fluids with thicknesses below a characteristic length scale remain substantially adhered to the roughened surface, whereas fluid layers above the characteristic length can flow, creating flow lines (surface defects) and disrupting the flatness of the fluid surface. For example, non-limiting thicknesses for the lubrication fluid (as measured from the valleys of the roughened surface are on the order of 5-20 μm when the peak to valley height is ~5 μm.

In certain embodiments, lubricating fluid can be applied by pupating drops of the fluid onto the roughened surface, or by dipping the roughened surface into a reservoir carrying lubricating fluid. In some embodiments, lubricating fluid can be sprayed, cast, or drawn onto the roughened surface. The lubricating liquid can infiltrate the roughened surface by capillary action, which can wet the roughened surface and form a film on top of it. Lubricating fluid and the roughened surface can be both generated by a double-spraying process, where emulsions consisting of nano/microparticles are first sprayed onto a flat solid surface to form a substantially roughened solid layer, and then lubricating fluid can be sprayed onto this freshly formed layer for further infiltration.

TABLE 1

Temperature dependence of liquid viscosity of DuPont Krytox Oils.

| Temperature (° C.) | Viscosity (cm²/s) | | | | | | | |
|---|---|---|---|---|---|---|---|---|
| | Krytox 100 | Krytox 101 | Krytox 102 | Krytox 103 | Krytox 104 | Krytox 105 | Krytox 106 | Krytox 107 |
| 20 | 0.124 | 0.174 | 0.38 | 0.82 | 1.77 | 5.22 | 8.22 | 15.35 |
| 40 | 0.055 | 0.078 | 0.15 | 0.30 | 0.60 | 1.60 | 2.43 | 4.50 |
| 100 | — | 0.02 | 0.03 | 0.05 | 0.084 | 0.18 | 0.25 | 0.42 |
| 204 | — | — | — | — | — | 0.031 | 0.041 | 0.06 |
| 260 | — | — | — | — | — | — | 0.024 | 0.033 |

The viscosities of both Object A and Liquid B affect the performance of SLIPS. Because the liquid repellency of SLIPS is conferred by the presence of the Liquid B, the viscosity of Liquid B can affect the physical characteristics of liquid repellency of SLIPS, such as the velocity of Object A. The more viscous the Liquid B, the less mobile the given Liquid A will be.

Figure 36:
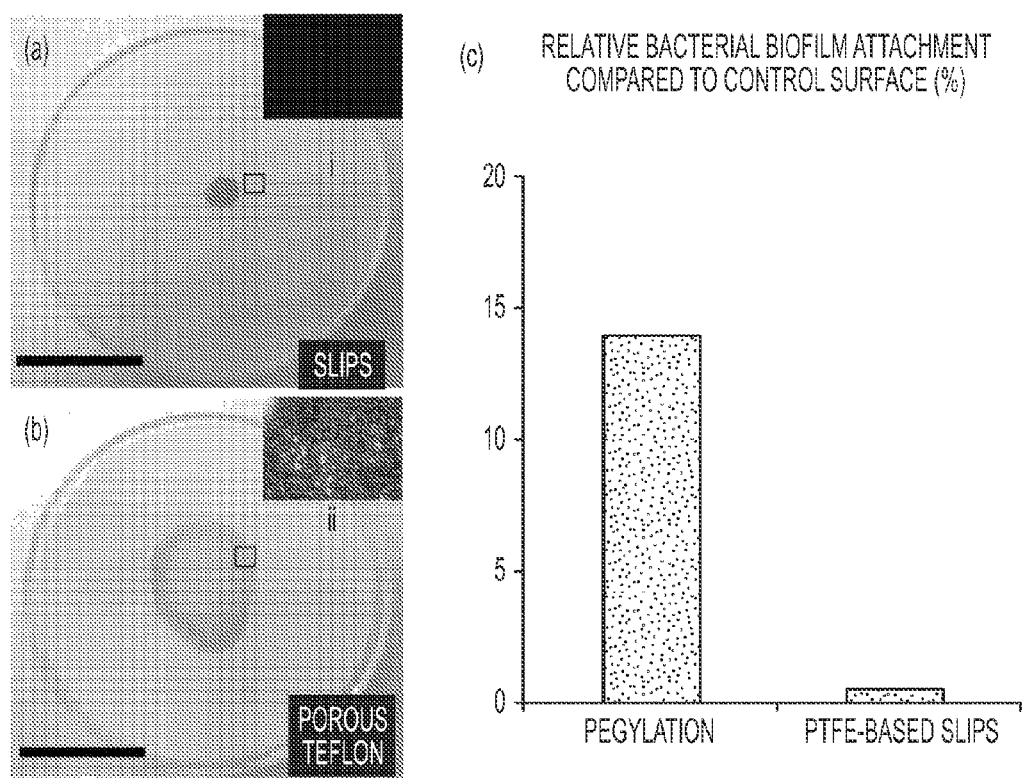
FIG. 36 shows images (A-B) of surface typologies investigated with respect to biofilm attachment properties. The remains of an evaporated drop of *Pseudomonas aeruginosa* biofilm-forming culture is shown on each surface, a superhydrophobic nanoporous PTFE surface (A) and a slippery liquid infused porous surface (SLIPS) (B). Biofilm grown on the PTFE and nanostructured superhydrophobic silicon substrates showed complete wetting of the surface and a slimy coffee ring. In contrast, biofilm on the SLIPS substrate cleanly retracted from the surface as it evaporated. The insets (i) and (ii) show fluorescence micrographs of remaining bacteria on these surfaces following 48 hour incubation of *P. aeruginosa* biofilm. The relative bacterial biofilm attachment was significantly less on PTFE-based SLIPS compared to the PEGylation surface (C).

For a Liquid A of constant viscosity, its velocity on SLIPS reduces with increasing viscosity of Liquid B. For example, referring to FIG. 36, for a 50 μL of Liquid A of absolute viscosity of 1 cP, its velocities on SLIPS with Liquid B of In addition, lubricating fluid may infiltrate into the pores of the roughened surface by capillary action and form an ultra-smooth film on top of the roughened surface. In certain embodiments, when sufficient quantity of the lubricating fluid is provided, the lubricating fluid may wet the entire roughened surface structure and form an ultra-smooth film over the underlying roughened surface.

Facile Replenishment of Liquid B

Another advantageous feature of using porous materials may be the presence of the capillary network within the bulk materials, which can further enhance transport of Liquid B through the pores. The porous structure can provide a replenishing fluid at the surface and may be useful to address evaporation or other materials loss of Liquid B from the SLIPS surface. For example, in the case where a portion of Liquid B is reduced at the surface of the materials due to evaporation, sudden pressure purging, physical damage or the like, Liquid B can be replenished by the capillary action in these networks. Replenishing Liquid B is drawn through the porous body of the substrate by capillary wicking to refresh the upper surface of SLIPS. In certain embodiments, the porous material itself can be utilized as a fluid reservoir to store Liquid B for subsequent capillary refilling purpose.

Figure 9A:
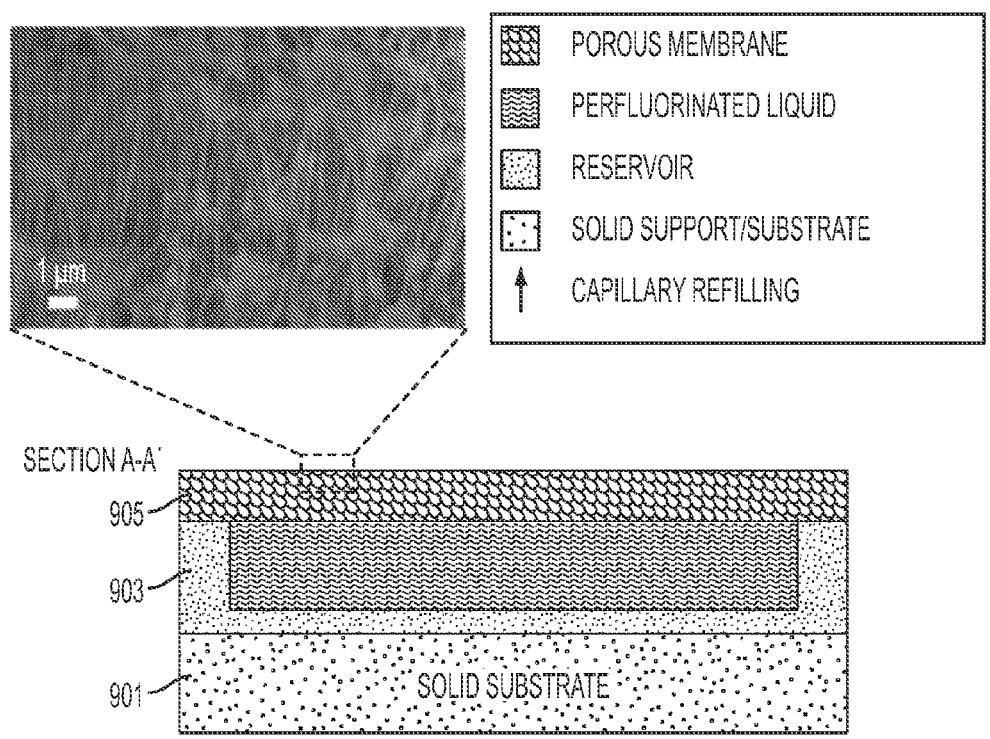
FIG. 9A shows SLIPS coupled to a Liquid B reservoir that can replenish evaporating or removed Liquid B in accordance with certain embodiments.

In certain embodiments, as shown in FIG. 9A, to further prolong the life time of the slippery surface of the present disclosure, the porous material 905 can be connected to an external fluid reservoir 903 sitting on a solid substrate 901, where the capillary networks within the porous material 905 can help transfer (e.g., via wicking) the Liquid B from the fluid reservoir 903 to the porous material 905.

Figure 9B:
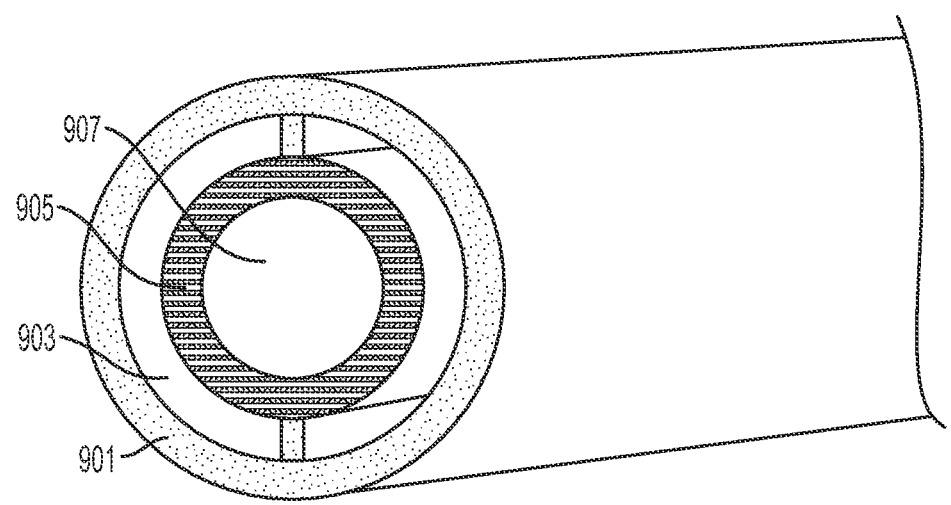
FIG. 9B shows SLIPS formed inside a cylindrical tube with a Liquid B reservoir that can replenish evaporating or removed Liquid B in accordance with certain embodiments.

FIG. 9B shows an alternate embodiment where SLIPS having a porous material 905 as the roughened surface is formed in an inner surface of a cylindrical tube. As shown, the cylindrical tube 901 has a first annular region 903 serving as a fluid reservoir for Liquid B, followed by an inner annular region of SLIPS having a porous material 905, which surrounds a hollow region 907 for the flow of Liquid A. In operation, Liquid B in annular region 903 transfers into the (e.g., via wicking) the porous material 905 to form a SLIPS and Liquid A can flow through the hollow region with little to no drag at the interface between 905 and 907.

Figure 9C:
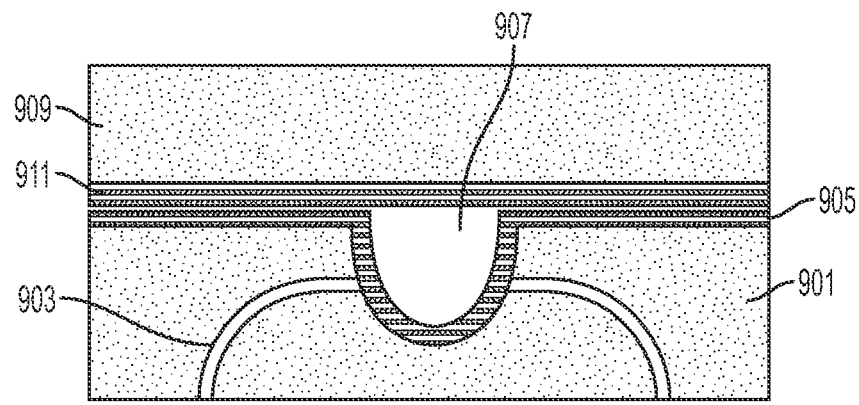
FIG. 9C shows SLIPS formed along the surface of an arbitrary shaped flow path coupled to a channel for replenishing evaporating or removed Liquid B in accordance with certain embodiments.

FIG. 9C shows yet another embodiment where SLIPS is formed in an inner surface of an arbitrarily shaped flow path. As shown, the bottom substrate 901 has a channel 903 serving as a fluid replenishment source for Liquid B that is coupled to the porous material 905 of SLIPS. Porous material 905 is formed by combining a bottom substrate 901 having a depressed region mated with a top substrate 909 having a substantially flat porous material 911 formed thereon. The combination of the top and bottom substrate portions forms a hollow region 907 for the flow of Liquid A.

Figure 9D:
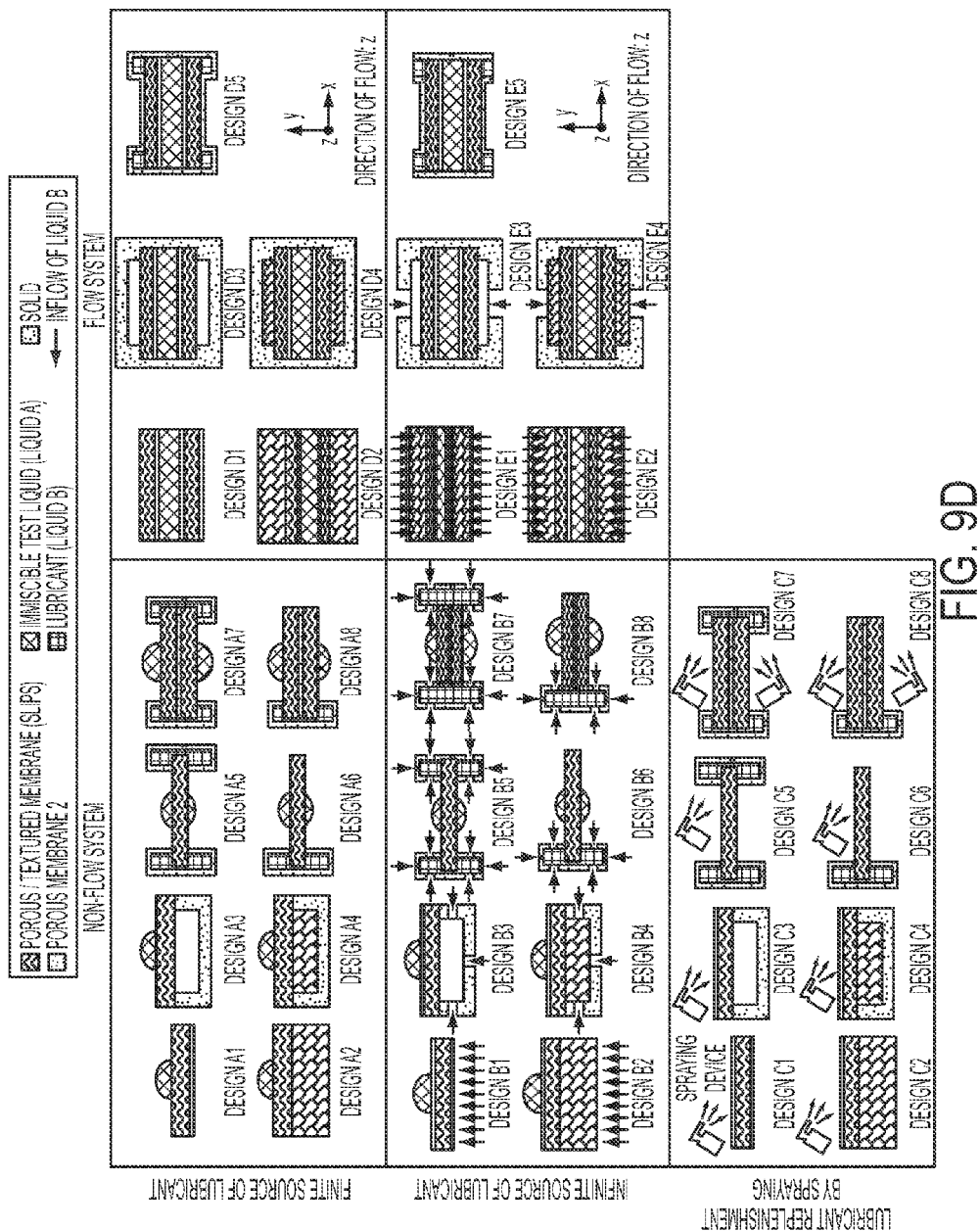
FIG. 9D shows images of showing the formation of the bottom substrate portion of FIG. 9C in accordance with certain embodiments.

FIG. 9D shows some optical micrographs on how the bottom substrate 901 and SLIPS 905 of FIG. 9C can be formed. As shown, a TEFLON filter paper 930 having a three-dimensionally random network of pores can be placed between a male mold 940 and female mold 950 defining an arbitrary flow path and the male mold 940 and female mold 950 can be pressed together to replicate the flow path pattern on the TEFLON filter paper 930. The template TEFLON filter paper 930 can be placed inside the female mold 950, which now serves as bottom substrate 901 of FIG. 9C, and a substantially flat substrate 909 having another substantially flat TEFLON filter paper, serving as SLIPS 911, can be applied thereon (not shown) to form the flow path 907 shown in FIG. 9C. The female mold 950 may further contain channel 903 (not shown) that serves to replenish Liquid B as needed.

Figure 35:
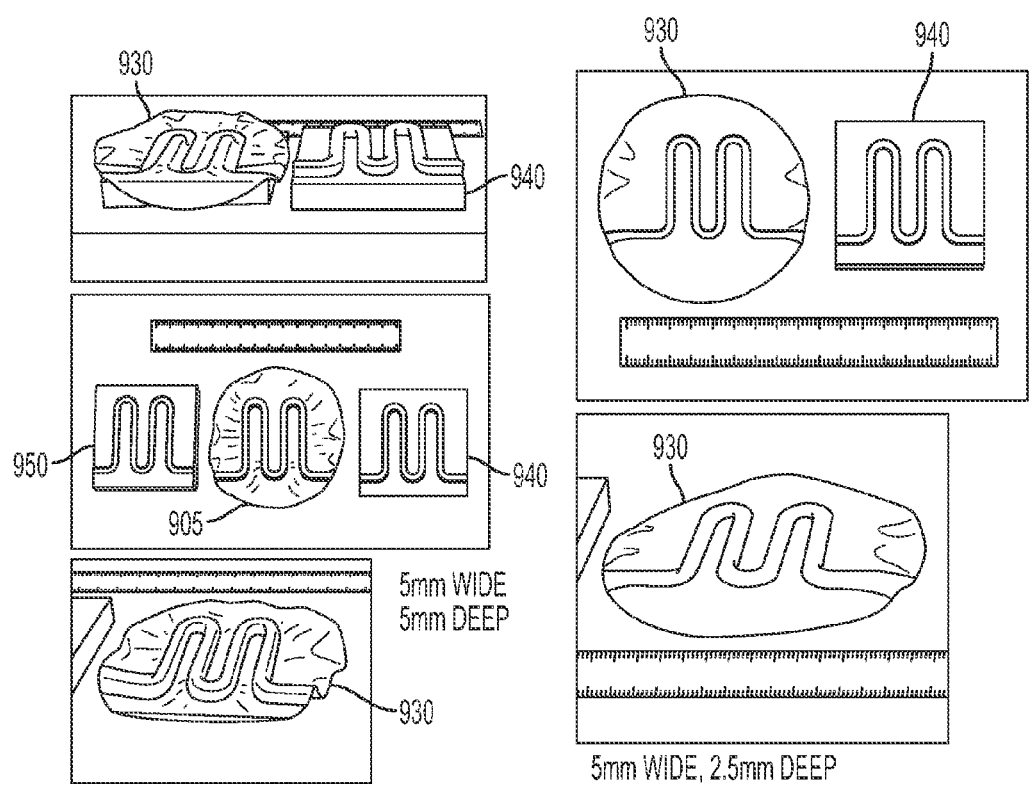
FIG. 35 shows images of a process for fabricating a SLIPS tubing from ePTFE membranes.

FIG. 35 shows several other non-limiting embodiments of SLIPS and how Liquid B can be replenished to the SLIPS in each of those embodiments. The left column corresponds to systems where SLIPS is exposed to both Medium X and Liquid A (shown as a droplet). The right column corresponds to systems where SLIPS is exposed to substantially only Liquid A (shown as a plug between two SLIPS). In either system, Liquid B can be replenished to SLIPS as needed. The top row shows scenarios where there is a finite amount of Liquid B. The middle row shows scenarios where there is a large source (e.g., practically infinite source from the viewpoint of the amount of Liquid B needed to replenish the SLIPS) of Liquid B. The bottom row shows scenarios where Liquid B can be replenished by spraying Liquid B as needed, either manually or automatically. As shown, many different configurations and their derivatives are possible.

It should be noted that while the embodiments described herein refers to a porous material, any other suitable roughened surface described herein can be utilized.

Substrate-Lubricating Fluid Combinations

SLIPS can sustain fluid impact pressures on the order of $10^3$-$10^7$ Pa (e.g., at least from an order of magnitude to five orders of magnitude higher than the current state-of-the-art surface) and are capable of restoring themselves to exceptional liquid repellency upon critical physical damages with a fast self-healing time on the orders of 100 ms to 1 s (i.e., 4 orders of magnitude faster than the current state-of-the-art surface).

Figure 28:
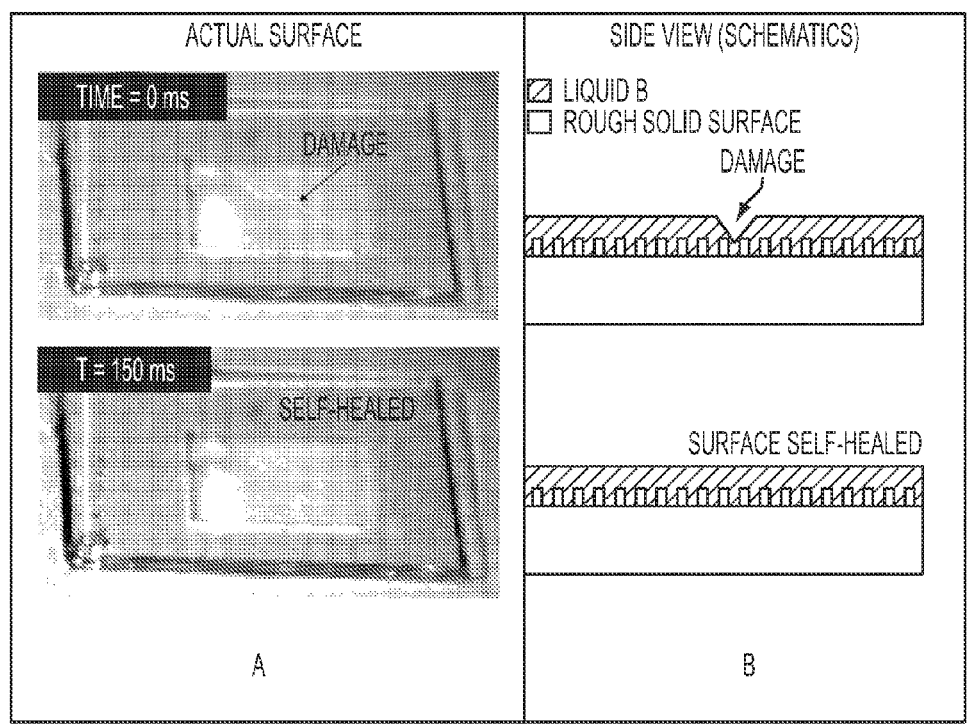
FIG. 28A-B shows images of the surface of the present disclosure demonstrating self-healing properties, where the self-healing time scale is on the order of 100 ms in accordance with certain embodiments.
Figure 29:
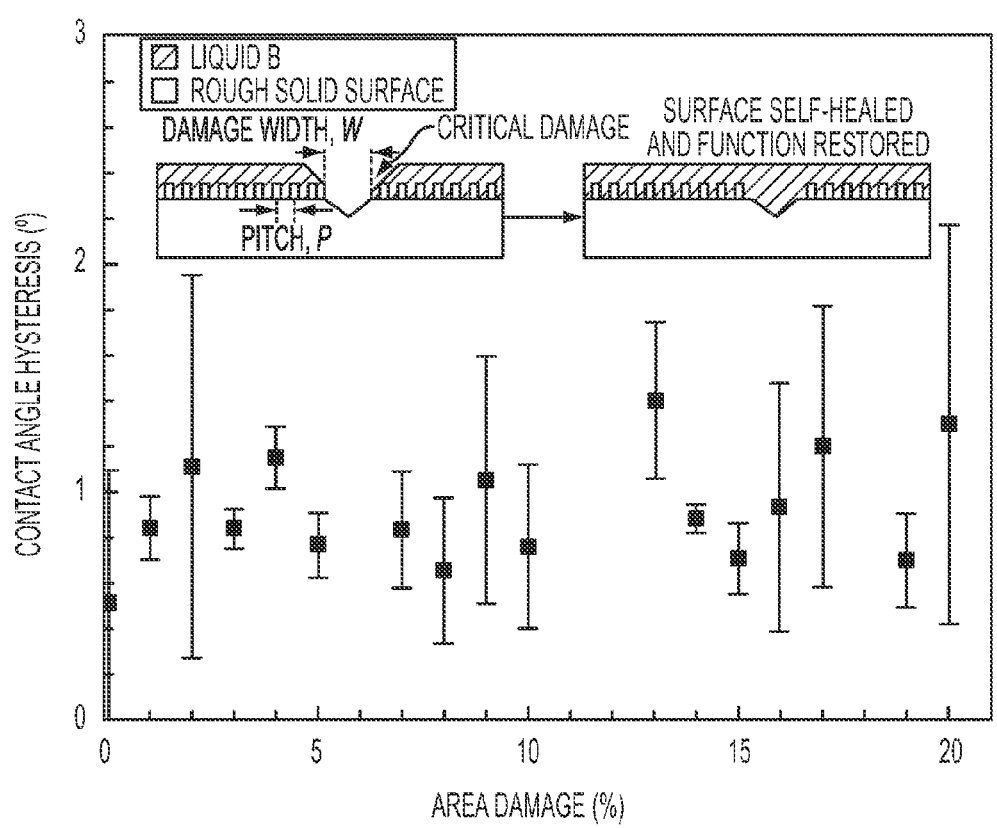
FIG. 29 is a chart showing restoration of liquid repellency function after critical physical damage (test liquid=decane, $\gamma_{LV}$=23.6±0.1 mN/m) in accordance with certain embodiments.

In certain embodiments, the lubricating liquid and the roughened surface can be selected so that they have fast self-healing properties. As used herein, "self-healing" refers to re-formation of an ultra-smooth (and even substantially molecularly flat) surface after physical impact (e.g., damage). The lubricating fluid is a self-healing coating that rapidly restores the fluid-repellant function following damage to the porous material by abrasion or impact. Self healing occurs when the lubricating fluid flows toward the damaged area of the substrate by surface energy-driven capillary action to spontaneously fill the physical void. The recovery time is a function of lubricant viscosity. For example, for Krytox 100, the self-healing time is on the order of 150 ms to 1 s. For Krytox 103, which is more viscous than Krytox 100 the self-healing time is on the order of O(10s) or more. In one or more embodiments, the recovery time for a fluid displacement is less than one second. In other embodiments, the recovery time is a fraction of a second. In still other embodiments, the recovery time is 50 ms, 60 ms, 70 ms, 80 ms, 90 ms, 100 ms, 110 ms, 120 ms, 130 ms, 140 ms, 150 ms, 160 ms, 170 ms, 180 ms, 190 ms, 200 ms, 210 ms, 220 ms, 230 ms, 240 ms, 250 ms, 1 second, 5 seconds 10 seconds, 30 seconds, 60 seconds, 90 seconds, 120 seconds, or more depending on the amount of damage sustained, and the characteristics of the lubricating fluid and substrate used. The self-healing behavior of the liquid repellant surfaces can be a function of the interaction between the lubricating liquid and the roughened surface, as well as the viscosity of the lubricating liquid. Typical kinematic viscosities of the lubricating liquid are in the range of 0.10 $cm^2$/s to 10 $cm^2$/s. Referring to FIGS. 28 and 29, particle impact or scratching can damage the surface by, for example, breaking or removing the topographical features of the surface in a small area. In one embodiment, the measured self-recovery time for a ~50 μm fluid displacement of FC-70 lubrication fluid on epoxy-resin-based SLIPS was only ~150 ms (FIG. 28A). Typically the impact can also displace the lubricating liquid, resulting in a scratch or pit and exposing the substrate surface. Due to the wicking capability and good wetting properties of the lubricating liquid, however, the liquid layer can flow back to refill the pit or scratch and to regenerate the smooth fluid surface. FIG. 28A shows time-lapse images showing self-healing capability of SLIPS from a ~50 μm-wide physical damage on a time scale on the order of 100 ms. FIG. 28B is a schematic illustration of the type of damage that may occur and the healing process that restores the smooth liquid surface. A reservoir with extra fluid can be available to 'top off' the fluid layer thickness to maintain the desired thickness. Even more surprising, SLIPS can repeatedly restore their fluid-repellent function to surfaces sustaining large areas of physical damage. FIG. 29 is a chart showing restoration of liquid repellency function after critical physical damage (test liquid=decane, $\gamma_{LV}$=23.6±0.1 mN/m) in accordance with certain embodiments.

In certain embodiments, the roughened surface may be functionalized so that the critical surface energy of the roughened surface is higher than the surface energy of lubricating liquid; under these conditions, complete wetting of the lubricating liquid can spontaneously occur throughout the roughened surface.

In certain embodiments, when the critical surface energy of the roughened surface is lower than the surface energy of the lubricating liquid, the roughened surface may be provided with a high degree of roughness to promote wetting of the lubricating liquid within the pores of the roughened surface.

In certain embodiments, the lubricating liquid has a surface energy that is less than the surface energy of the roughened surface. In general, when the surface energy of the liquid B is lower than the surface energy of the underlying roughened surface, it tends to wet the solid well. More precisely, the spreading of a liquid depends on the spreading parameter (S), where $S=[E_{substrate}]_{dry}-[E_{substrate}]_{wet}=\gamma_{SO}-(\gamma_{SL}+\gamma)$, with $\gamma_{SO}$, $\gamma_{SL}$, and $\gamma$ as the surface energy of at the solid/air, solid/liquid, and liquid/air interfaces, respectively. The liquid wets a surface completely if S>0 while the drop partially wet a surface if S<0. (See, e.g., P.-G. de Gennes, F. Brochard-Wyart, D. Quere, Capillarity and Wetting Phenomena: drops, bubbles, pearls, waves, Springer (New York, N.Y.), 2004, the contents of which is incorporated by reference herein in its entirety). Thus, in certain embodiments, the surface energy of the liquid B is such that the spreading parameter S is positive.

In certain embodiments, the critical surface tension of the roughened surface (i.e., $\gamma_{c-S}$) may be comparable or lower than the surface tension of the lubricating liquid (i.e., $\gamma_{LV-B}$). For example, the critical surface tension of the roughened surface may be at least 1.25 times lower than the surface tension of the lubricating liquid.

In certain embodiments, the lubricating liquid (and similarly Liquid A) may be non-reactive with the roughened surface. For example, the roughened surface and the lubricating liquid (or liquid to be repelled) can be chosen so that the roughened surface does not dissolve upon contact with the lubricating liquid (or liquid to be repelled). In particular, perfluorinated liquids (the lubricating liquid) work exceptionally well to repel a broad range of polar and non-polar Liquids A and their solidified forms.

Any suitable combination of the roughened surface and the lubricating liquid described above can be employed. For example, a perfluorinated liquid as the lubricating liquid and a nanostructured surface made out of polymer (for example, epoxy resin, silicone, and Teflon) that are chemically functionalized with end-functional group of —CF₃ or other similar fluorocarbon groups can be utilized as the roughened surface. Other materials including sapphire, diamonds, silicon, glass, and metals (e.g., aluminum) can be also used with suitable chemical functionalization schemes.

It is contemplated that SLIPS may be incorporated in an environment (1) where the lubricating fluid is exposed substantially only to Object A or (2) where the lubricating fluid is exposed to both Object A and another fluid environment, such as medium X (e.g., atmosphere, underwater, etc.).

When SLIPS is incorporated in the first environment (e.g., inside the interior of medical tubing, outside the exterior of the medical tubing, and the like) (see FIG. 9B), the working combinations of the solid/lubricant/immiscible test liquid may be chosen by satisfying the condition shown in Equation (e1).

$$\Delta E_0 = \gamma_{BX} \cos \theta_{BX} - \gamma_{AX} \cos \theta_{AX} > 0 \quad (e1)$$

where $\gamma_{AX}$, and $\gamma_{BX}$ represent the surface energies of the Object A-medium X interface, and the lubricating liquid-medium X interface, respectively. Also, $\theta_{AX}$, and $\theta_{BX}$ are the equilibrium contact angles of Object A and the lubricating fluid on a flat solid surface immersed under medium X environment, respectively.

On the other hand, when SLIPS is incorporated in the second environment (e.g., exposed to atmosphere/underwater/other immiscible fluid environments), satisfying the following two conditions can provide a suitable SLIPS.

$$\Delta E_1 = R(\gamma_{BX} \cos \theta_{BX} - \gamma_{AX} \cos \theta_{AX}) - \gamma_{AB} > 0 \quad (e2)$$

$$\Delta E_2 = R(\gamma_{BX} \cos \theta_{BX} - \gamma_{AX} \cos \theta_{AX}) + \gamma_{AX} - \gamma_{BX} > 0 \quad (e3)$$

where $\gamma_{AB}$ represent the surface energies of the Object A—the lubricating fluid interface.

In addition, when SLIPS is operated in a fully immersed environment (i.e., air/water/other immiscible fluids), the density difference between the Object A and Medium X can also play a role for the fluid repellency. For example, in order for Object A to slide off from SLIPS by gravity, the density of Object A, $\rho_A$, may desirably be greater than that of the Medium X, $\rho_X$ (i.e., $\rho_A > \rho_X$). Moreover, the size of Object A may be on the order of, or greater than, its capillary length. Specifically, capillary length is a characteristic length scale that quantifies the dominance of body force over surface force on an object, which can be quantitatively expressed as $(\gamma/\rho g)^{1/2}$, where $\gamma$, $\rho$, and g are surface tension and density of the liquid, and gravity, respectively.

The different parameters noted in (e1), (e2) and (e3) (i.e. $\theta_{AX}$, $\theta_{BX}$, $\gamma_{AX}$, $\gamma_{BX}$, $\gamma_{AB}$, R) can be obtained or estimated utilizing the following standard techniques. While the following standard techniques are described, other techniques can be utilized.

Table 2A shows examples of working combinations of the solid, Liquids A and B of the slippery surface based on the predictions from the proposed relationship, $R(\gamma_{BX} \cos \theta_{BX} - \gamma_{AX} \cos \theta_{AX}) + \gamma_{AX} - \gamma_{BX} > 0$. When the relationship holds, the lubricating liquid will stay in intimate contact with the porous solid without being displaced by Liquid A. Note that the equilibrium contact angles were estimated from the average values of the advancing and receding contact angles of Liquid A and the lubricating liquid on the flat solid surface. Satisfying the relationship can help promote the operation stability of the slippery surface where the liquid layer is substantially completely covered by the test liquid (i.e., two-phase environments that involve a single fluid interface between the test liquid and the liquid layer) and where the liquid layer contacts a droplet of the test fluid as well as air (i.e., three-phase environments that involve three fluid interfaces of (i) test liquid-liquid layer, (ii) test liquid-air, and (iii) liquid layer-air).

In Table 2A, "Y" indicates that Liquid B forms a stable lubricating film, and is not displaced by Object A, and "N" indicates that Liquid B is displaced by Object A. R represents the roughness factor of the substrate, $\gamma_A$ represents the surface tension of Object A, and $\gamma_B$ represents the surface tension of Object B. $\theta_A$ and $\theta_B$ were estimated from the measured static contact angles on flat substrates from at least three individual measurements (see Table 2B).

TABLE 2A

Comparison of the Governing Relationships with Experimental Observations for Various Solid-Liquid-A-Liquid-B Combinations.

| Solid | Liquid A | Liquid B | R | $\gamma_A$ | $\gamma_B$ | $\gamma_{AB}$ | $\theta_A$ | $\theta_B$ | $\Delta E_0$ | $\Delta E_1$ | $\Delta E_2$ | Stable Film? Theory | Exp. |
|---|---|---|---|---|---|---|---|---|---|---|---|---|---|
| S. Epoxy | H₂O | FC-70 | 2 | 72.4 | 17.1 | 56.0 | 113.1 | 14.1 | 45.0 | 34.0 | 145.3 | Y | Y |
| S. Epoxy | C₁₆H₃₄ | FC-70 | 2 | 27.2 | 17.1 | 8.2 | 70.5 | 14.1 | 7.5 | 6.8 | 25.1 | Y | Y |
| S. Epoxy | C₁₃H₂₈ | FC-70 | 2 | 25.9 | 17.1 | 7.7 | 63.5 | 14.1 | 5.0 | 2.4 | 18.9 | Y | Y |
| S. Epoxy | C₁₀H₂₂ | FC-70 | 2 | 23.6 | 17.1 | 6.7 | 60.0 | 14.1 | 4.8 | 2.9 | 16.1 | Y | Y |
| S. Epoxy | C₈H₁₈ | FC-70 | 2 | 21.4 | 17.1 | 4.4 | 50.7 | 14.1 | 3.0 | 1.7 | 10.4 | Y | Y |
| S. Epoxy | C₆H₁₄ | FC-70 | 2 | 18.6 | 17.1 | 2.6 | 40.1 | 14.1 | 2.4 | 2.1 | 6.2 | Y | Y |
| S. Epoxy | C₅H₁₂ | FC-70 | 2 | 17.2 | 17.1 | 2.5 | 30.8 | 14.1 | 1.8 | 1.1 | 3.7 | Y | Y |
| Epoxy | H₂O | FC-70 | 2 | 72.4 | 17.1 | 56.0 | 92.6 | 33.5 | 17.5 | −20.9 | 90.4 | Y/N | Y |
| Epoxy | C₁₆H₃₄ | FC-70 | 2 | 27.2 | 17.1 | 8.2 | 30.6 | 33.5 | −9.2 | −26.5 | −8.2 | N | N |
| Epoxy | C₁₃H₂₈ | FC-70 | 2 | 25.9 | 17.1 | 7.7 | 26.9 | 33.5 | −8.8 | −25.4 | −8.9 | N | N |
| Epoxy | C₁₀H₂₂ | FC-70 | 2 | 23.6 | 17.1 | 6.7 | 14.2 | 33.5 | −8.6 | −23.9 | −10.7 | N | N |
| Epoxy | C₈H₁₈ | FC-70 | 2 | 21.4 | 17.1 | 4.4 | 7.9 | 33.5 | −6.9 | −18.3 | −9.6 | N | N |
| Epoxy | C₆H₁₄ | FC-70 | 2 | 18.6 | 17.1 | 2.6 | 0 | 33.5 | −4.3 | −11.3 | −7.2 | N | N |
| Epoxy | C₅H₁₂ | FC-70 | 2 | 17.2 | 17.1 | 2.5 | 0 | 33.5 | −2.9 | −8.4 | −5.8 | N | N |
| Epoxy | H₂O | FC-70 | 1 | 72.4 | 17.1 | 56.0 | 92.6 | 33.5 | 17.5 | −38.5 | 72.8 | Y/N | N |
| Epoxy | C₁₆H₃₄ | FC-70 | 1 | 27.2 | 17.1 | 8.2 | 30.6 | 33.5 | −9.2 | −17.4 | 0.9 | Y/N | N |
| Epoxy | C₁₃H₂₈ | FC-70 | 1 | 25.9 | 17.1 | 7.7 | 26.9 | 33.5 | −8.8 | −16.5 | 0.0 | Y/N | N |
| Epoxy | C₁₀H₂₂ | FC-70 | 1 | 23.6 | 17.1 | 6.7 | 14.2 | 33.5 | −8.6 | −15.3 | −2.1 | N | N |
| Silicon | C₁₆H₃₄ | H₂O | 1 | 27.2 | 72.4 | 51.1 | 5.6 | 13.1 | 43.4 | −7.7 | −1.8 | N | N |
| Silicon | C₁₀H₂₂ | H₂O | 1 | 23.6 | 72.4 | 50.8 | 5.0 | 13.1 | 47.0 | −3.8 | −1.8 | N | N |
| Silicon | C₈H₁₈ | H₂O | 1 | 21.4 | 72.4 | 50.8 | 5.0 | 13.1 | 49.2 | −1.6 | −1.8 | N | N |
| Silicon | C₆H₁₄ | H₂O | 1 | 18.6 | 72.4 | 50.9 | 5.0 | 13.1 | 52.0 | 1.1 | −1.8 | Y/N | N |
| Silicon | C₅H₁₂ | H₂O | 1 | 17.2 | 72.4 | 51.0 | 5.0 | 13.1 | 53.4 | 2.4 | −1.8 | Y/N | N |
| PDMS | Water | PDMS | 1 | 72.4 | 21.3 | 43 | 110 | 5.0 | 46.0 | 3.0 | 97.1 | Y | Y |
| PP | Water | PDMS | 1 | 72.4 | 21.3 | 43 | 108 | 5.0 | 46.0 | 0.6 | 94.7 | Y | Y |
| PP | Water | PDMS | 2 | 72.4 | 21.3 | 43 | 108 | 5.0 | 43.6 | 44.2 | 138.3 | Y | Y |
| PTFE | Water | PDMS | 2 | 72.4 | 21.3 | 43 | 115 | 5.0 | 51.8 | 60.6 | 154.7 | Y | Y |

TABLE 2B

Measured Contact Angles of Various Liquids on Different Flat Solids.

| Solids | | H₂O | C₁₆H₃₄ | C₁₃H₂₂ | C₁₀H₂₂ | C₈H₁₈ | C₆H₁₄ | C₅H₁₂ | FC-70 |
|---|---|---|---|---|---|---|---|---|---|
| S. Epoxy | $\theta_{adv}$ | 118.9 ± 1.7 | 76.3 ± 1.4 | 72.8 ± 0.2 | 66.0 ± 4.1 | 57.7 ± 2.5 | 52.5 ± 0.3 | 36.4 ± 2.5 | 23.7 ± 4.1 |
| | $\theta_{static}$ | 113.1 ± 2.8 | 70.5 ± 2.0 | 63.5 ± 2.8 | 60.0 ± 2.8 | 50.7 ± 3.0 | 40.1 ± 4.2 | 30.8 ± 3.1 | 14.1 ± 0.8 |
| | $\theta_{rec}$ | 90.8 ± 0.9 | 50.0 ± 3.9 | 48.1 ± 3.1 | 38.5 ± 0.7 | 23.8 ± 4.0 | 22.8 ± 1.7 | 17.0 ± 1.8 | 0.0 ± 0.0 |
| Epoxy | $\theta_{adv}$ | 100.3 ± 3.1 | 32.8 ± 1.4 | 28.3 ± 1.1 | 15.0 ± 1.6 | 9.7 ± 1.2 | ~0.0 | ~0.0 | 35.1 ± 0.6 |
| | $\theta_{static}$ | 92.6 ± 1.8 | 30.6 ± 0.4 | 26.9 ± 1.7 | 14.2 ± 0.7 | 7.9 ± 0.7 | ~0.0 | ~0.0 | 33.5 ± 1.1 |
| | $\theta_{rec}$ | 67.0 ± 4.5 | 25.7 ± 0.9 | 25.4 ± 0.7 | 13.7 ± 0.9 | 6.1 ± 0.2 | ~0.0 | ~0.0 | 26.7 ± 1.4 |
| Silicon | $\theta_{adv}$ | 14.4 ± 2.7 | 17.3 ± 1.6 | — | 7.9 ± 1.0 | <5.0 | <5.0 | <5.0 | — |
| | $\theta_{static}$ | 13.1 ± 1.7 | 5.6 ± 1.1 | — | <5.0 | <5.0 | <5.0 | <5.0 | — |
| | $\theta_{rec}$ | ~0.0 | ~0.0 | — | ~0.0 | ~0.0 | ~0.0 | ~0.0 | — |

TABLE 2C

Measured Surface Tension for Various Polar and Non-Polar Liquids.

| Liquid | Surface Tension (mN/m) | n |
|---|---|---|
| Water | 72.4 ± 0.1 | 116 |
| Glycerol | 60.3 ± 1.1 | 35 |
| Ethylene Glycol | 48.1 ± 0.3 | 32 |
| Dipropylene Glycol | 32.3 ± 0.3 | 35 |
| Extra-light Crude Oil* | 27.0 ± 0.8 | 15 |
| Light Crude Oil** | 25.6 ± 0.9 | 15 |
| Hexadecane | 27.2 ± 0.2 | 31 |
| Tridecane | 25.9 ± 0.1 | 30 |
| Dodecane | 25.3 ± 0.1 | 32 |
| Undecane | 24.6 ± 0.2 | 32 |
| Decane | 23.6 ± 0.1 | 32 |
| Nonane | 22.6 ± 0.2 | 31 |
| Octane | 21.4 ± 0.2 | 30 |
| Heptane | 19.9 ± 0.3 | 32 |
| Hexane | 18.6 ± 0.5 | 30 |
| Pentane | 17.2 ± 0.5 | 57 |
| 3M Fluorinert™ FC-70 | 17.1 ± 0.3 | 43 |

Notice that $\gamma_A$ and $\gamma_B$ are equivalent to $\gamma_{AX}$ and $\gamma_{BX}$ defined in the text, and medium X is air specifically in this context. Variable $\gamma_{AB}$ represents the interfacial tension for Object A-Liquid B interface. Specifically, $\gamma_{AB}$ for water-perfluorocarbon and hydrocarbon-perfluorocarbon interfaces were measured by the pendant droplet method (see Table 2D) except the water-hydrocarbon interfaces, which are estimated from the formulation: $\gamma_{AB} = \gamma_A + \gamma_B - 2(\gamma_A^d \gamma_B^d)^{1/2}$, where $\gamma_A^d$ and $\gamma_B^d$ are the dispersion force contributions of the liquid surface tensions (Fowkes, F. M., *Ind. Eng. Chem.* 56, 40-42, 1964; Israelachvili, J. N. *Intermolecular and Surface Forces*, Academic Press, 2011). The dispersion force contribution of water surface tension is 21.8 mN/m (Fowkes, F. M., *Ind. Eng. Chem.* 56, 40-42, 1964). S. Epoxy represents silanized epoxy resin substrate. Alkanes are represented in $C_nH_{2n+2}$ where n=5, 6, 8, 10, 13, and 16.

TABLE 2D

Measured Interfacial Tension between a Perfluorocarbon and Various Liquids.

| Liquid/Liquid | Interfacial Tension (mN/m) | n |
|---|---|---|
| FC-70/Water | 56.0 ± 0.9 | 12 |
| FC-70/Hexadecane | 8.2 ± 0.2 | 25 |
| FC-70/Tridecane | 7.7 ± 0.3 | 26 |
| FC-70/Decane | 6.7 ± 0.2 | 26 |
| FC-70/Octane | 4.4 ± 0.2 | 25 |
| FC-70/Hexane | 2.6 ± 0.1 | 40 |
| FC-70/Pentane | <2.5 | 10 |

Generally, it may be important to have the chemical nature between the roughened solid and the Liquid B be similar. For example, non-polar Liquid B with fluorocarbon functional groups may adhere well with roughened solid surface that is functionalized with fluorocarbon groups (e.g., —$CF_3$, —$CF_2$). In another example, polar Liquid B may adhere well with roughened solid surface that is functionalized with hydroxyl groups (i.e., —OH).

In most of the cases, it may be desirable to have the surface energies of the roughened solid and Liquid B to be lower than the surface energy of Liquid A so that Liquid A will not displace Liquid B from the roughened solid.

In certain embodiments, when Liquid A is a low surface tension non-polar liquid (e.g., less than 30 mN/m), the roughened surface may be functionalized with low surface energy coatings (e.g., less than 30 mJ/m$^2$), such as —$CF_3$, —$CF_2H$, —$CF_3$ and —$CF_2$—, —$CF_2$—$CF_3$, —$CF_2$—CFH—, —$CF_2$—$CH_2$—, —CFH—$CH_2$—, and the like. Moreover, Liquid B may be selected to also exhibit low surface energy (e.g., less than 20 mJ/m$^2$), such as perfluorotributylamine, perfluorotri-n-pentylamine, perfluorohexane, perfluoro(2-butyl-tetrahydrofuran), perfluorocycloether, perfluoro n-alkyl morpholines, perfluoroalkylethers, perfluorotripropylamine, and the like.

Figure 26A:
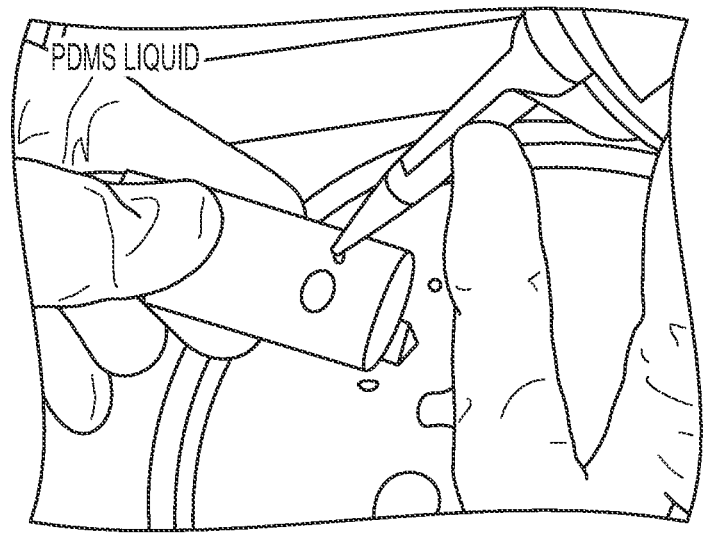
FIG. 26 shows images of whole human blood in nonwetting contact with SLIPS surfaces made with non perfluorocarbon lubricant liquids. Image (26A) shows a SLIPS surface generated using an infiltration of polydimethylsiloxane (PDMS) liquid (500 MW, X viscosity, OH-terminated, Sigma Aldrich) into an ePTFE membrane (1 μm, Sterlitech). Image (26B) shows a SLIPS surface generated using an infiltration of olive oil into an ePTFE membrane (1 μm, Sterlitech). In both cases the blood was found to not wet the surface, and rolled off without adhering to the surfaces.
Figure 26B:
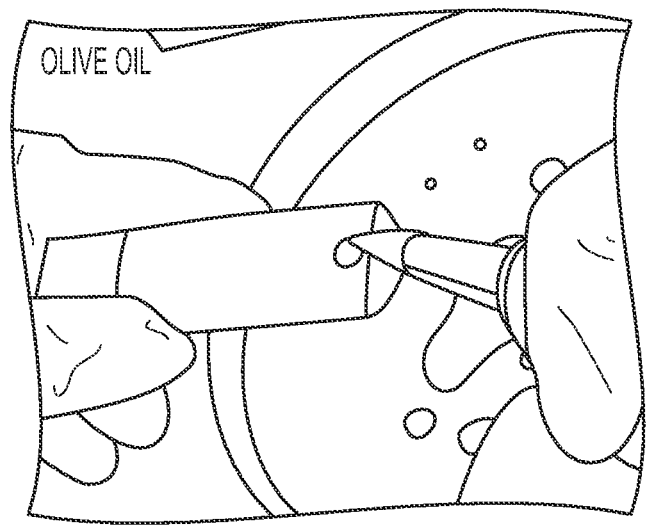

In certain embodiments, when Liquid A is a high surface tension liquid (e.g., water, condensation) or a solidified fluid, Liquid B can be selected from other higher surface energy fluids (i.e., ~20 mJ/m$^2$ or higher), such as polydimethylsiloxane, other liquid silicone elastomers or commercial food grade lubricants (e.g., KRYTOX™ FG lubricants), oils (e.g., vegetable or mineral oil (see FIG. 26B)), and the like. Image (A) in FIG. 26 shows a SLIPS surface generated using an infiltration of polydimethylsiloxane (PDMS) liquid (500 MW, X viscosity, OH-terminated, Sigma Aldrich) into an ePTFE membrane (1 μm, Sterlitech). Image (B) in FIG. 26 shows a SLIPS surface generated using an infiltration of olive oil into an ePTFE membrane (1 μm, Sterlitech). In both cases the blood was found to not wet the surface, and rolled off without adhering to the surfaces. In certain embodiments, as with low surface tension liquids, the roughened surface may be functionalized with low surface energy coatings (e.g., less than 30 mJ/m$^2$), such as —$CF_3$, —$CF_2H$, —$CF_3$ and —$CF_2$—, —$CF_2$—$CF_3$, —$CF_2$—CFH—, —$CF_2$—$CH_2$—, —CFH—$CH_2$—, and the like.

Table 3 shows some non-limiting examples of combinations of substrates, lubricating liquid (Liquid B), and liquid to be repelled (Liquid A). For example, in one embodiment, the solid substrate can be selected from the group consisting of polydimethylsiloxane, polypropylene, polytetrafluoroethylene, and the like. In this embodiment, lubricating liquids such as liquid silicone elastomers (e.g., polydimethylsiloxane), vegetable or mineral oil, liquid hydrocarbons, and combinations thereof can be applied to the solid substrate to create a SLIPS surface to repel materials such as simple aqueous fluids (e.g., water), complex aqueous fluids (e.g., blood), solidified fluids, and combinations thereof (Table 3, row 1).

In another embodiment, the solid substrate can be selected from the group consisting of fluoro-silanized metals (e.g., fluoro-silanized aluminum, silver, gold, platinum, copper, gold, palladium, zinc, titanium, and the like), fluoro-silanized natural polymers (e.g., fluoro-silanized synthetic polymers (e.g., fluoro-silanized epoxy resin, silicone, silicone rubber, latex, polytetrafluoroethylene, polyvinylfluoride, polyvinylidene fluoride, fluorinated ethylene propylene, thermoplastic elastomers, Teflon, and the like), and combinations thereof. Lubricating liquids such as perfluorinated fluids can be applied these solid substrates to repel any non-perfluorinated liquid (Table 3, row 2).

TABLE 3

Examples of Combinations of Materials for Making SLIPS Surfaces

| Row# | Solid | Liquid B | Liquid A |
|---|---|---|---|
| 1 | polydimethylsiloxane; polypropylene; polytetrafluoroethylene | polydimethylsiloxane; vegetable or mineral oil; liquid hydrocarbons | simple aqueous fluids; complex aqueous fluids; solidified fluids, |
| 2 | polytetrafluoroethylene; fluoro-silanized metals; fluoro-silanized natural polymers; fluoro-silanized synthetic polymers | all perfluorinated fluids | all non-perfluorinated fluids |

Figure 16:
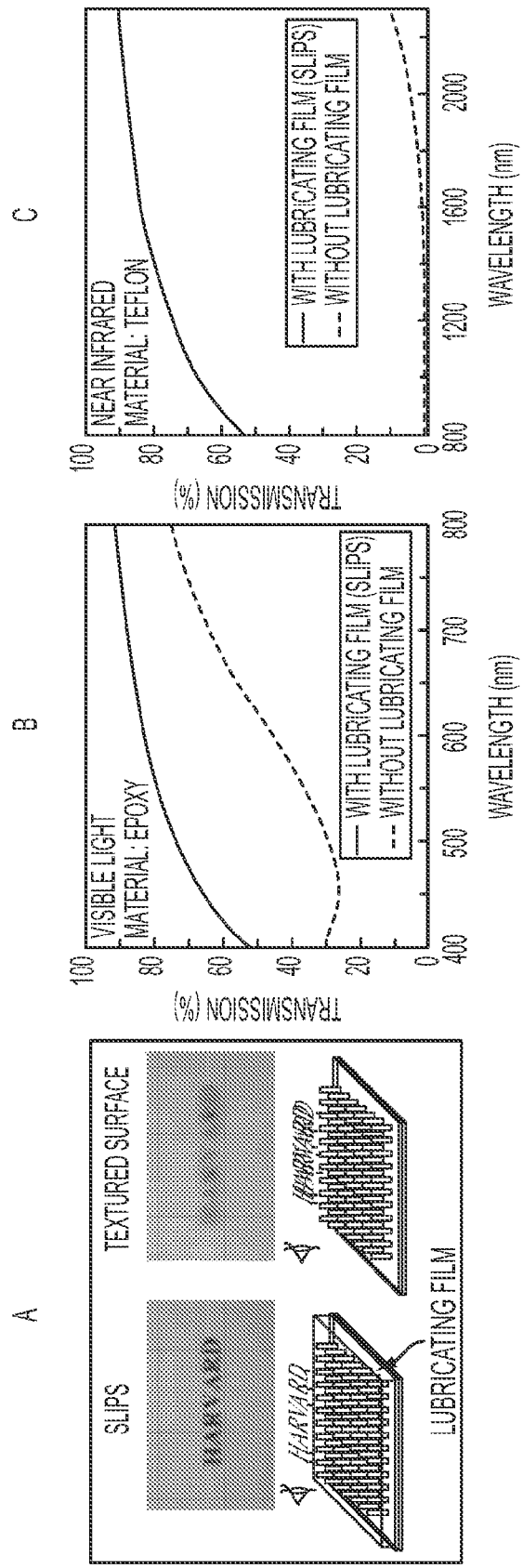
FIG. 16A Optical images showing enhanced optical transparency of an epoxy-resin-based SLIPS (left) as compared to significant scattering in the non-infused super hydrophobic nanostructured surface (right) in the visible light range. 16B. Optical transmission measurements for epoxy-resin-based SLIPS in the visible light range (400-750 nm). 16C. Optical transmission measurements for Teflon-based SLIPS in the near-infrared range (800-2300 nm).

In some embodiments, it may be desirable to have SLIPS that are optically transparent. By choosing a substrate and lubricating fluid with matching refractive indices, SLIPS can be made optically transparent in visible and/or near-infrared wavelengths (FIG. 16A-C). FIG. 16A shows optical images showing enhanced optical transparency of an epoxy-resin-based SLIPS (left) as compared to significant scattering in the non-infused super hydrophobic nanostructured surface (right) in the visible light range. FIG. 16B. shows optical transmission measurements for epoxy-resin-based SLIPS in the visible light range (400-750 nm). FIG. 16C shows optical transmission measurements for Teflon-based SLIPS in the near-infrared range (800-2300 nm). For example, FIG. 64 shows images of a transparent SLIPS surface made by the infiltration of a highly-ordered nanoporous SiO2 glass layer (A) with perfluorocarbon (FC-70) (B). When fully infiltrated, the layer is highly transparent (C).

Measurement of $\Theta_{ax}$, $\Theta_{bx}$: Advancing and Receding Angles, Static Angles The behavior of liquids on surfaces is described by an equilibrium contact angle. An equilibrium contact angle, θ, is the angle at which a liquid/vapor interface meets a solid surface, which is determined by the interactions across the three interfaces, e.g., solid/liquid/vapor. Experimentally, the most stable equilibrium contact angle of a liquid droplet on a real surface can be difficult to attain. Liquid droplets sitting on the surface exhibit a variety of contact angles bound by two extreme values. The upper limit is known as the apparent advancing contact angle ($\theta_A$), whereas the lower limit is referred as the apparent receding contact angle ($\theta_R$). The difference between these values is known as contact angle hysteresis (i.e., $\Delta\theta = \theta_A - \theta_R$, where $\theta_A \geq \theta \geq \theta_R$), which characterizes the liquid repellency of a surface. Conventionally, equilibrium contact angle can be roughly estimated by the average of the advancing and receding angles (i.e., $\theta = (\theta_A + \theta_R)/2$), or by a static contact angle, $\theta_{static}$ (i.e., $\theta = \theta_{static}$).

In practice, contact angle measurement can be performed by a number of different well-established techniques, such as the sessile drop method and the Wilhelmy method. In particular, the sessile drop method is among the most popular technique for contact angle measurement. In this technique, a liquid droplet is deposited on a targeted solid surface, where the liquid profile is captured by an optical system of a goniometer and geometrically fitted to obtain the contact angle. The contact angle measured from a static liquid droplet deposited on the surface is known as the static contact angle, $\theta_{static}$. Using the same system, advancing contact angle, $\theta_A$, can be measured while the volume of the drop is increasing until the wetting line starts to advance. Receding contact angle, $\theta_R$, can be measured by decreasing the volume of the drop and determining the contact angle just before the wetting line recedes. Alternatively, the advancing and the receding angles of the liquid drop can also be determined by gradually tilting the solid surface until the liquid drop starts to move.

Measurement of Fluid-Fluid Interfacial Tension: $\gamma_{AX}$, $\gamma_{BX}$, $\gamma_{AB}$ Fluid-fluid interfacial tension can be measured by many well-established techniques, such as the Wilhelmy plate method, the Du Noüy ring method, and the pendant drop method (e.g., see Drelich et al., in *Encyclopedia of Surface and Colloid Science*, pp. 3152-3166, Marcel Dekker Inc, 2002, the contents of which is incorporated by reference herein in its entirety). Among all of the techniques, the pendant drop method is among the most popular and versatile technique, which can be easily extended to a two-liquid system. The pendant drop method measures the shape of a fluid-fluid interface and quantifies the shape distortion due to the competition between the fluid-fluid interfacial tension and gravity. In practice, a drop of denser fluid (e.g., Object A) is suspended by a syringe needle in medium X (i.e., air/water/the lubricating fluid). Owing to the influence of gravity, the denser liquid droplet will be deformed as the liquid volume increases. The shape profile of the liquid droplet is captured by an optical system and subsequently analyzed by a computer software when the liquid volume is increased to the maximum possible size (i.e., before the liquid drop is detached from the syringe needle). The interfacial tension of the fluid-fluid interface, γ, can then be deduced from the formula, $\gamma = \Delta\rho g D^2/H$, where $\Delta\rho$ is the density difference between the two immiscible fluids, g is gravity, D is equatorial diameter of the liquid droplet, and H is drop shape dependent parameters which is a function of the shape profile of the droplet.

Measurement of Surface Roughness: R

Roughness of a surface can be quantitatively estimated by a number of indirect and direct approaches. For example, one of the simplest indirect methods to quantify surface roughness is the use of Wenzel's relationship to estimate the roughness by measuring the apparent contact angle of a surface. Specifically, the Wenzel's relationship can be described by the formula, $\cos\theta^* = R\cos\theta$, where $\theta^*$ and θ are the measured apparent contact angle of the roughened surface, and the equilibrium contact angle of a substantially flat surface (of same material), respectively.

For direct measurements, the surface roughness can be quantitatively measured by using an atomic force microscope or by a scanning electron microscopy. Specifically, the use of atomic force microscope (AFM) allows for simple, and direct 3-dimensional mapping of the surface morphology. In practice, a suitable AFM probe is selected for the measurements depending on the aspect ratio of the surface features (note: aspect ratio is defined as the ratio between the height and the width of the surface features). As a rule of thumb, sharp AFM probes (i.e., radius of tip curvature<10 nm) of very high aspect ratio (i.e. >10) would allow for relatively precise measurements of surfaces with general morphologies. Alternatively or in addition, the use of scanning electron microscope can also be used for the measurement of the top view and cross sectional view of the surface morphologies for the estimation of the surface roughness.

In certain embodiments, the roughness of a 3-D porous material can be estimated by measuring the surface morphology of the top-most layer of the porous material. Particularly, the estimation may be particularly well-suited when complete wetting of a surface is predominately induced by the roughness at the surface layer of the material that is in intimate contact with the fluid.

In some embodiments in which SLIPS is used to repel complex biological fluids without permitting adhesion, clot formation, or fouling, the lubricating fluid is an organofluorine oil, (i.e., perfluorinated oils including, without limitation, tertiary perfluoroalkylamines (such as perfluorotri-n-pentylamine, FC-70; perfluorotri-n-butylamine FC-40, etc), perfluoroalkylsulfides, perfluoroalkylsulfoxides, perfluoroalkylethers, perfluorocycloethers (like FC-77), perfluoropolyethers (such as KRYTOX family of lubricants by DuPont), perfluoroalkylphosphines, and perfluoroalkylphosphineoxides).

In certain embodiments, the slippery surface of the present disclosure has a coefficient of friction that is lower than polytetrafluoroethylene (PTFE or TEFLON). In certain embodiments, the coefficient of friction is less than 0.1, less than 0.05, or even less than 0.04. In certain embodiments, the coefficient of friction can be measured against polished steel, Teflon, or the slippery surface of the present disclosure itself (e.g., slippery surface/slippery surface).

Figure 27A:
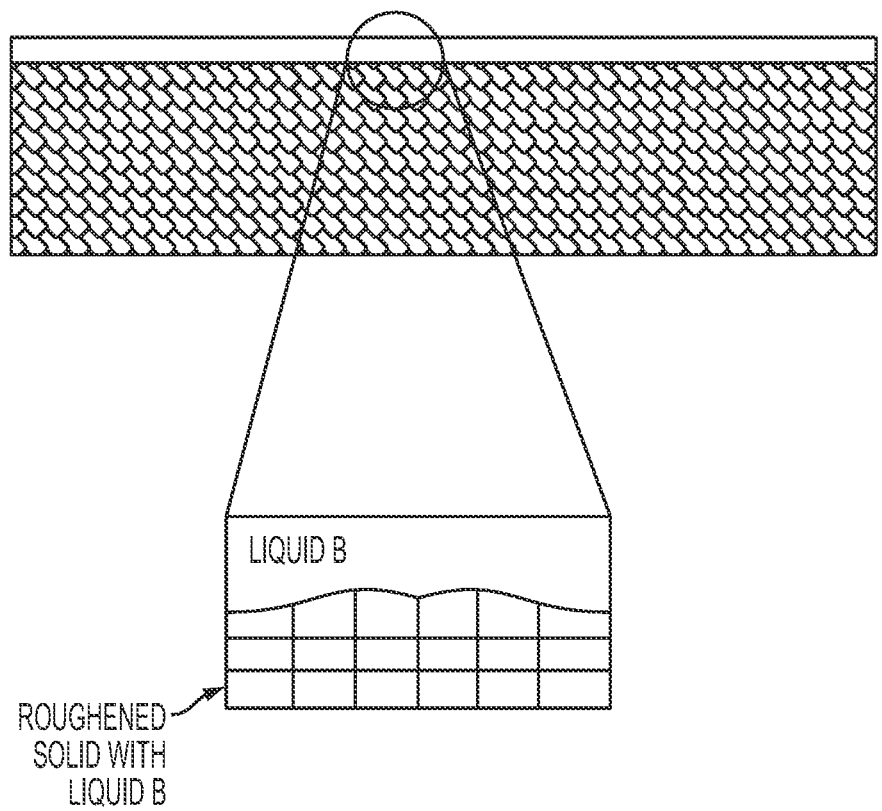
FIG. 27A shows a schematic of a slippery surface having an over-coated Liquid B formed over a roughened surface in accordance with certain embodiments.
Figure 27B:
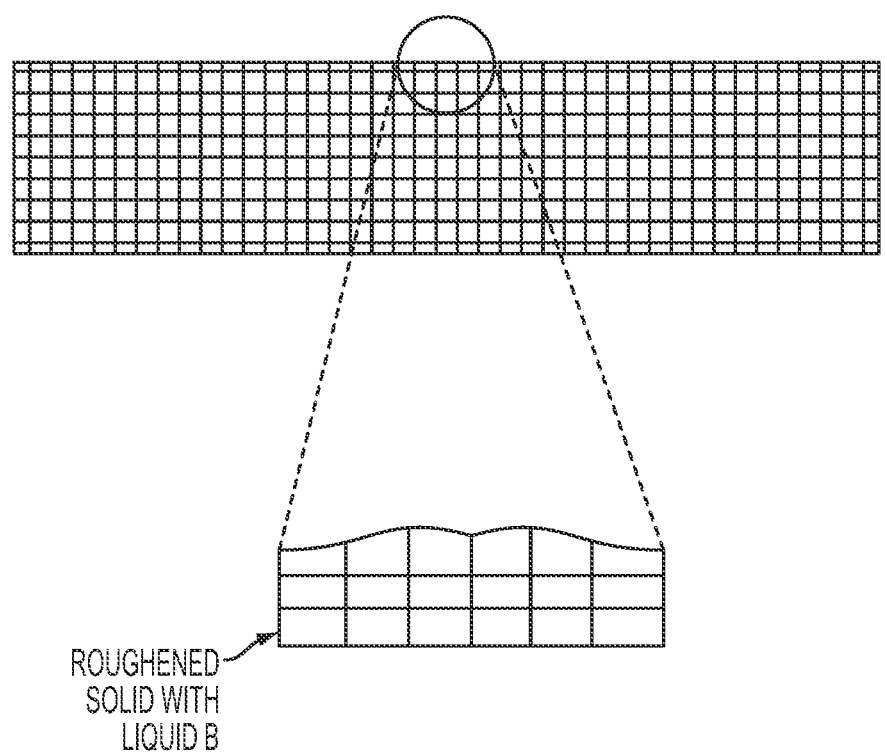
FIG. 27B shows a schematic of a slippery surface with Liquid B infiltrated into the roughened surface in accordance with certain embodiments.

As shown in FIGS. 27A and 27B, there are two working configurations for the invention. In the first configuration, as shown in FIG. 27A, the lubricating liquid (Liquid B) overcoats the roughened solid surface, and forms an ultra-smooth surface. Liquid B can wet the roughened surface, filling the hills and valleys of the roughened surface, and forming an ultra-smooth surface over the roughened surface. Particularly, Liquid B can form a liquid layer over the roughened surface so that the liquid layer covers the roughened surface to form an ultra-smooth surface of Liquid B (FIGS. 6A and 6B). In certain embodiments, the average surface roughness of the surface is on the order of or less than about 1 nm based on high resolution atomic force microscopy measurements. The presence of the micro/nanostructures can significantly enhance the wetting of Liquid B, thereby creating a uniformly-coated slippery functional layer over the topographies. The first configuration may be useful for repelling a liquid, gas, or molecules or particulates contained within liquids.

In the second configuration shown in FIG. 27B, the lubricating fluid (Liquid B) infiltrates within the solid textures, forming a composite solid-liquid interface. Rather than forming the ultra-smooth surface of FIG. 27A the lubricating fluid (Liquid B) can infiltrate the roughened solid surface and form a thin coating thereon that follows the topography of the underlying roughened solid surface. In certain embodiments, the thin coating may be conformally coating the top surface of the roughened surface. As used herein, "conformal coating" can encompass forming a molecular monolayer or multiple molecular layers that surround the materials of the roughened surface. However, the "conformal coating" is not thick enough to form an overcoat layer to form an ultra-smooth surface, such as described in FIG. 27A. In certain embodiments, the second configuration may be particularly useful for repelling materials in their solid forms.

In order for the lubricating fluid (Liquid B) to remain attached with the roughened surface, at least the following three properties are desirable: (1) the lubricating fluid (Liquid B) readily imbibes into, wets, and stably adheres within the substrate, (2) the roughened surface is preferentially wetted by the lubricating fluid (Liquid B) rather than by the material to be repelled, and (3) the lubricating fluid (Liquid B) and the material to be repelled are immiscible.

Object A and Lubricating Liquid Combinations

In certain embodiments, the solidification temperature of the lubricating liquid may be lower than that of Liquid A. In certain embodiments, the lubricating liquid can maintain its liquid state below the solidification temperature of Liquid A, thereby retaining its slippery property. Without wishing to be bound by theory, there may be at least two reasons to maintain the lubricating liquid in a liquid state even while Liquid A solidifies.

First, having the lubricating liquid maintained in the liquid state may result in reduced adhesion at the interface between Object A and the lubricating liquid in the directions normal and tangential to the substrate surface, as compared to that of the interface between the solidified form of the material to be repelled and other solid surfaces (i.e., roughened surfaces). Adhesion between surfaces may be proportional to the contact surface area, where the smoothness of the lubricating liquid surface can minimize contact area between Object A and the lubricating liquid, due to the smaller surface area at the interface compared to a roughened surface. The reduced adhesion may facilitate removal of Object A from the lubricating liquid surface at much reduced force per unit area.

Second, the ultra-smooth surface of the lubricating liquid may also reduce the condensation of Liquid A from the air (i.e., assuming the vaporized form of Liquid A is present in air) when the surface of the lubricating liquid is cooled to the temperature below the solidification temperature of Liquid A. This may be due to the fact that there are few or even no nucleation sites on the lubricating liquid surface, which greatly reduce the nucleation probability of the repelled liquid. As a result, the formation of fog and frost (i.e., solidified form of the repelled liquid at the micro- and nanoscale) on the surface can require more stringent conditions (e.g., lower temperature or a higher vapor pressure of Liquid A in the air) as compared to the other solid surfaces. To maintain the lubricating liquid in the liquid state, the solidification temperature of the lubricating liquid may be 25° C. lower than that of Liquid A at atmospheric pressure.

In certain embodiments, the boiling temperature of the lubricating liquid may be higher than the solidification temperature of Liquid A. In certain embodiments, the lubricating liquid may be able to maintain its liquid state above the solidification temperature of Liquid A. Additionally, maintaining the liquid state may facilitate the removal of Liquid A from the lubricating liquid surface due to the aforementioned liquid-slippery function, while the surface is held at a temperature above the solidification temperature of Liquid A. This may be particularly important for applications in surface defrosting, where the lubricating liquid may be defrosted using minimal energy input (e.g., at a lower temperature) as compared to other solid surfaces. To maintain the lubricating liquid in the liquid state, the boiling temperature of the lubricating liquid may be 215° C. higher than the solidification temperature of Liquid A at atmospheric pressure.

In certain embodiments, the solid to be repelled (or Object A) may slide off from the surface of the lubricating liquid by gravity when the surface is tilted at an angle with respect to the horizontal, given that Object A is larger than a characteristic size. Specifically, the effect of gravity on Object A may be more dominant when its size is much larger than the capillary length of Liquid A. Specifically, capillary length is a characteristic length scale that quantifies the dominance of body force over surface force on an object, which can be quantitatively expressed as $(\gamma/\rho g)^{1/2}$, where $\gamma$, $\rho$, and g are surface tension and density of the liquid, and gravity, respectively. For example, Object A may be at least 3 times larger than the capillary length of Liquid A.

In certain embodiments, the lubricating liquid may be selected to satisfy additional criteria needed for Solid A or Object A. For example, when Object A is a biological object, the lubricating liquid can be selected so that the lubricating liquid is not toxic to Object A so that facile transport of Object A to desired locations without reducing the biological activity of Object A. In another example, the lubricating liquid can be selected so that the lubricating liquid is toxic to Object A so that removal of Object A can be further coupled with reducing the biological activity of Object A.

Certain Advantages for Porous Material

In certain embodiments, use of a porous material having a high degree of physical roughness for the roughened surface may be particularly advantageous. The presence of such physical roughness may induce not only the complete wetting of the lubricating fluid, but also provide additional capillary adhesion for the lubricating fluid within the porous solid to further enhance the mechanical stability, wicking characteristics and the ability to "hold" Liquid B "in place" even at high tilt angles.

Moreover, another important feature for the use of porous material may be that further structuring of the surface may not be needed, since the physical structures are already embedded within the bulk material. In such cases, the porous material can be a self-supporting, free-standing membrane which can be attached/glued/adhered to the external or internal surfaces of materials with any kind of geometry (see FIGS. 7 and 8).

In addition, one of the unique features of using porous materials may be the presence of the capillaries network within the bulk materials, which can further enhance transport of Liquid B through the pores. For example, in the case where a portion of Liquid B is consumed locally at the surface of the material due to evaporation, sudden pressure purging, physical damage or the like, Liquid B can be replenished effectively by the capillary action in these networks. In certain embodiments, the porous material itself can be utilized as a fluid reservoir to store the fluorinated liquid for subsequent capillary refilling (see FIG. 8).

Figure 8:
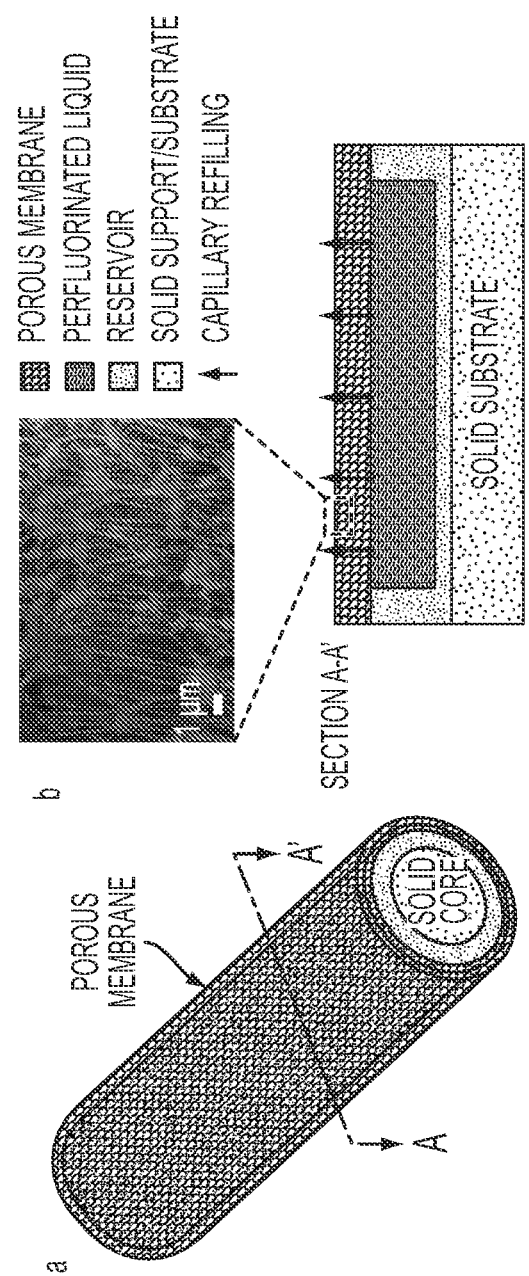
FIG. 8*a-b* shows a schematic of capillary refilling in accordance with certain embodiments.

In certain embodiments, to further prolong the life time of the slippery surface of the present disclosure, the porous material can also be connected to an external fluid reservoir or larger storage capacity, where the capillary networks can help autonomously transfer the liquids from the fluid reservoir to the bulk material itself (see FIG. 8).

In certain embodiments, the pore size of the porous material can roughly be on the order of the capillary length of Liquid B or smaller. Such size may allow stabilizing Liquid B in the porous material. Capillary length, $\lambda_c$, can be defined as $\lambda_c = \sqrt{\gamma/\rho g}$, where $\gamma$ is the surface tension of Liquid B, $\rho$ is the density of Liquid B, and $g$ is gravity.

Taking the exemplary case of utilizing fluorinated liquids as Liquid B, the surface tension of fluorinated liquids is in the range of about 10-20 mN/m at a typical density of about 1800 kg/m$^3$. Typical pore sizes can range from about 50 nm to about 100 μm or up to about 1 mm, such as about 750 μm-1 mm.

In certain embodiments, use of a porous material for the roughened surface may provide even higher resistance to pressure change than the high pressure changes that can be obtained using solid surfaces having certain topographies. For example, while a 2.5D (vertically extruded) nanostructured structure shown in FIG. 5A may be able to sustain a maximum rate of pressure change on the order of $10^5$ Pa per second, use of a porous material (e.g., Teflon membrane) may be able to tolerate pressure change up to about $6 \times 10^6$ Pa per second without displacing Liquid B. Without wishing to be bound by theory, the improved pressure tolerance of the 3D porous material can be attributed to the enhanced capillary interactions between the intricate 3D porous network and Liquid B.

In certain embodiments, use of a porous material for the roughened surface may provide even higher pressure stabilities than the high pressure stability that can be obtained using solid surfaces having certain topographies (e.g., "2.5D" nanostructured surface). For example, use of a porous material (e.g., Teflon membrane) may be able to tolerate absolute pressure up to about $6.9 \times 10^7$ Pa while maintaining its liquid slippery function. Without wishing to be bound by theory, the improved pressure tolerance of the 3D porous material can be attributed to the incompressibility of the lubricating layer, as well as the resistance of liquid penetration into the porous structure.

Prevention or Reduction of Microbial Attachment and Biofilm Formation

Materials (Object As) that can be repelled by SLIPS include microbes such as bacteria. Bacteria primarily exist in robust, surface-associated communities known as biofilms, which are ubiquitous in both natural and anthropogenic environments. Contamination of surfaces by microbial attachment occurs easily, and is the first step towards the development of bacterial biofilms as multicellular communal super-organisms (De Beer, D. & Stoodley, P. Microbial Biofilms. *Prokaryotes* 1:904-937 (2006); O'Toole, G., Kaplan, H. B. & Kolter, R. Biofilm Formation as Microbial Development. *Annu. Rev. Microbiol.* 54:49-79 (2000)). Mature biofilms resist a wide range of antimicrobial treatments and pose persistent pathogenic threats.

Bacteria can physically attach to a vast variety of surfaces—from hydrophilic to hydrophobic, by a variety of mechanisms (O'Toole et al., 2000; De Beer et al., 2006; O'Toole 2003; Christensen et al., 1985; Costerton et al., 1987; Gristina, 1987; Jacques et al., 1987). The typical mechanisms include an initial deposition of proteins, known as conditioning layer, by physical or chemical adsorption, which precedes the attachment of the bacteria itself. Conditioning films, which may contain fibronectin, fibrinogen, collagen, and other proteins, coat a biomaterial surface almost immediately and provide receptor sites for bacterial or tissue adhesion (Gristina, 1987).

Biofilm formation is of concern to industry and healthcare because it causes contamination of plumbing, oil wells, heat exchangers, building ventilation, food storage, medical implants, and other systems. Biofilms threaten human health by triggering an immune response, releasing harmful endotoxins and exotoxins, and clogging indwelling catheters; in fact, biofilms are responsible for nearly 100,000 nosocomial deaths annually in the United States and 80% or more of all microbial infections in humans.

Treatment or removal of adherent biofilm is difficult, costly, and in medical systems is frequently impossible. It is imperative to prevent rather than treat biofilm formation, and accordingly a wide range of bacteria-resistant surfaces have been proposed. At the same time, strategies for biofilm prevention based on surface chemistry treatments have been found to only transiently affect initial attachment. Most current strategies for preventing biofilm formation rely either on a release of biocidal compounds or on inhibiting adhesion (Banerjee, I., R. C. Pangule, and R. S. Kane, *Antifouling coatings: recent developments in the design of surfaces that prevent fouling by proteins, bacteria, and marine organisms*. Advanced Materials, 2011; Zhao, L., et al., *Antibacterial coatings on titanium implants*. Journal of Biomedical Materials Research Part B: Applied Biomaterials, 2009. 91(1): p. 470-480).

In the first case, traditional techniques involve the design of coatings that release agents such as antibiotics, quaternary ammonium salts, and silver ions into the surrounding aqueous environment. Such agents have been incorporated into a variety of engineering polymers and other materials (Banerjee (2011)).

The latter approach has focused on the use of surface chemical functional groups that inhibit protein adsorption as a means to inhibit bacterial adhesion. One of the most commonly studied such surface modifications is poly(ethylene glycol), or PEG (Park, K. D., et al., *Bacterial adhesion on PEG modified polyurethane surfaces. Biomaterials*, 1998. 19(7-9): p. 851-859; Prime, K. L. and G. M. Whitesides, *Self-assembled organic monolayers: model systems for studying adsorption of proteins at surfaces*. Science (New York, N.Y.), 1991. 252(5010): p. 1164.)).

More recently, structured superhydrophobic surfaces have been suggested for preventing biofilm attachment owing to the trapped air between their micro/nanoscale surface features and therefore, in principle, the reduced available solid attachment area for biofilm (see, e.g., U.S. Patent Application No. 61/434,217, filed on Jan. 19, 2011, which is incorporated herein in its entirety).

These strategies, however, are generally transient. Materials that persistently resist bacteria are difficult to achieve by surface chemistry alone. The surface chemistry is subject to desorption over time, a limitation that has driven much research in the area of strengthening the physisorption of, e.g., PEG coatings (Banerjee (2011). However, even if no desorption occurs and bacteria are unable to attach directly to a substrate, nonspecific adsorption of proteins and surfactants secreted by bacteria can still mask the underlying chemical functionality (Bos, R., et al., *Retention of bacteria on a substratum surface with micro patterned hydrophobicity*. Fems Microbiology Letters, 2000. 189(2): p. 311-315). Additionally, any defects or voids in the surface chemistry could serve as nucleation sites for bacterial attachment. Structured superhydrophobic surfaces in the Cassie (trapped air) state are prone to irreversible wetting (Wenzel transition), especially with the production of bacterial surfactant, which seriously limits their lifetime in submerged environments (Poetes, R., et al., *Metastable Underwater Superhydrophobicity*. Physical Review Letters, 2010. 105(16)).

Strategies involving leaching of biocides are limited over a longer timescale since their reservoir is finite and subject to depletion (Zhao, L., et al., *Antibacterial coatings on titanium implants*. Journal of Biomedical Materials Research Part B: Applied Biomaterials, 2009. 91(1): p. 470-480). Also, the emergence of antibiotic- and silver-resistant pathogenic strains, along with new restrictions on the use of biocide-releasing coatings in the marine environment, has necessitated the development of new strategies (Hall-Stoodley, L., J. W. Costerton, and P. Stoodley, *Bacterial biofilms: from the natural environment to infectious diseases*. Nature Reviews Microbiology, 2004. 2(2): p. 95-108; Trevors, J., *Silver resistance and accumulation in bacteria*. Enzyme and Microbial Technology, 1987. 9(6): p. 331-333; Costerton, J., P. Stewart, and E. Greenberg, *Bacterial biofilms: a common cause of persistent infections*. Science, 1999. 284(5418): p. 1318.).

Systemic and topical antimicrobial products have become extensively used to combat biofilm contamination in health care, agriculture, and industrial settings, and increasingly by the general public as well. Commercial products employ a wide variety of active chemical agents, or biocides, often delivered in liquid form and sometimes as vapor. One review of antiseptics and disinfectants identifies 12 classes of liquid agents and 5 common types of vapor-phase sterilants. Regardless of the particular chemistry or mechanism, biocides must be able to reach the target cell to cause damage. At the multicellular level, therefore, the effective biocide must penetrate into the extracellular matrix (ECM)—the slime-like "cement" of biofilm. Biofilms, however, offer their member cells protection from environmental threats. It has been reported that ECM acts as a diffusion barrier and as a charged binding filter for certain antibiotics, and that it complements enzymes and multidrug resistance pumps on cells that remove antimicrobials. The resistance to threats covers a wide range of treatments: biofilms exposed to chlorine bleach for 60 minutes are reported to still have live cells; biofilms in pipes continuously flushed over 7 days with multiple biocides recolonize the pipes, and biofilms have been reported to survive in bottled iodine solution for up to 15 months. Biofilms' resistance to antimicrobials may be related to the extreme nonwettability of their surface as well as resistance to vapor penetration.

SLIPS can repel various types of bacteria and prevent biofilm formation. SLIPS can repel, or prevent or reduce attachment of bacteria suspended in solution, airborne bacteria, and the like. In one embodiment, the type of bacteria repelled by SLIPS is gram positive bacteria. In another embodiment, the type of bacteria repelled by SLIPS is a gram negative bacteria. Non-limiting examples of bacteria repelled by SLIPS include members of the genus selected from the group consisting of *Actinobacillus* (e.g., *Actinobacillus actinomycetemcomitans*), *Acinetobacter* (e.g., *Acinetobacter baumannii*), *Aeromonas*, *Bordetella* (e.g., *Bordetella pertussis*, *Bordetella bronchiseptica*, and *Bordetella parapertussis*), *Brevibacillus*, *Brucella*, *Bacteroides* (e.g., *Bacteroides fragilis*), *Burkholderia* (e.g., *Burkholderia cepacia* and *Burkholderia pseudomallei*), *Borelia* (e.g., *Borelia burgdorfen*), *Bacillus* (e.g., *Bacillus anthracis* and *Bacillus subtilis*), *Campylobacter* (e.g., *Campylobacter jejuni*), *Capnocytophaga*, *Cardiobacterium* (e.g., *Cardiobacterium hominis*), *Citrobacter*, *Clostridium* (e.g., *Clostridium tetani* or *Clostridium difficile*), *Chlamydia* (e.g., *Chlamydia trachomatis*, *Chlamydia pneumoniae*, and *Chlamydia psiffaci*), *Eikenella* (e.g., *Eikenella corrodens*), *Enterobacter*, *Escherichia* (e.g., *Escherichia coli*), *Francisella* (e.g., *Francisella tularensis*), *Fusobacterium*, *Flavobacterium*, *Haemophilus* (e.g., *Haemophilus ducreyi* or *Haemophilus influenzae*), *Helicobacter* (e.g., *Helicobacter pylori*), *Kingella* (e.g., *Kingella kingae*), *Klebsiella* (e.g., *Klebsiella pneumoniae*), *Legionella* (e.g., *Legionella pneumophila*), *Listeria* (e.g., *Listeria monocytogenes*), *Leptospirae*, *Moraxella* (e.g., *Moraxella catarrhalis*), *Morganella*, *Mycoplasma* (e.g., *Mycoplasma hominis* and *Mycoplasma pneumoniae*), *Mycobacterium* (e.g., *Mycobacterium tuberculosis* or *Mycobacterium leprae*), *Neisseria* (e.g., *Neisseria gonorrhoeae* or *Neisseria meningitidis*), *Pasteurella* (e.g., *Pasteurella multocida*), *Proteus* (e.g., *Proteus vulgaris* and *Proteus mirablis*), *Prevotella*, *Plesiomonas* (e.g., *Plesiomonas shigelloides*), *Pseudomonas* (e.g., *Pseudomonas aeruginosa*), *Providencia*, *Rickettsia* (e.g., *Rickettsia rickettsii* and *Rickettsia typhi*), *Stenotrophomonas* (e.g., *Stenotrophomonas maltophila*), *Staphylococcus* (e.g., *Staphylococcus aureus* and *Staphylococcus epidermidis*), *Streptococcus* (e.g., *Streptococcus viridans*, *Streptococcus pyogenes* (group A), *Streptococcus agalactiae* (group B), *Streptococcus bovis*, and *Streptococcus pneumoniae*), *Streptomyces* (e.g., *Streptomyces hygroscopicus*), *Salmonella* (e.g., *Salmonella enteriditis*, *Salmonella typhi*, and *Salmonella typhimurium*), *Serratia* (e.g., *Serratia marcescens*), *Shigella*, *Spirillum* (e.g., *Spirillum minus*), *Treponema* (e.g., *Treponema pallidum*), *Veillonella*, *Vibrio* (e.g., *Vibrio cholerae*, *Vibrio parahaemolyticus*, and *Vibrio vulnificus*), *Yersinia* (e.g., *Yersinia enterocolitica*, *Yersinia pestis*, and *Yersinia pseudotuberculosis*), *Xanthomonas* (e.g., *Xanthomonas maltophilia*) and combinations thereof.

In particular, SLIPS has been shown to prevent 99.6% of common bacterial biofilm attachment under both flow and static conditions, which represents at least a 30× reduction in biofilm attachment over best-case-scenario, state-of-the-art surface treatments based on PEGylation.

Moreover, SLIPS can repel various types of fungi. Non-limiting examples of fungi repelled by SLIPS include members of the genus *Aspergillus* (e.g., *Aspergillus flavus*, *Aspergillus fumigatus*, *Aspergillus glaucus*, *Aspergillus nidulans*, *Aspergillus niger*, and *Aspergillus terreus*), *Blastomyces dermatitidis*, *Candida* (e.g., *Candida albicans*, *Candida glabrata*, *Candida tropicalis*, *Candida parapsilosis*, *Candida krusei*, and *Candida guillermondii*), *Coccidioides immitis*, *Cryptococcus* (e.g., *Cryptococcus neoformans*, *Cryptococcus albidus*, and *Cryptococcus laurentii*), *Histoplasma capsulatum* var. *capsulatum*, *Histoplasma capsulatum* var. *duboisii*, *Paracoccidioides brasiliensis*, *Sporothrix schenckii*, *Absidia corymbifera*; *Rhizomucor pusillus*, *Rhizopus arrhizous*, and combinations thereof.

SLIPS can also repel various types of viruses and virus-like particles. In one or more embodiments, the virus repelled by SLIPS is selected from the group consisting of dsDNA viruses, ssDNA viruses, dsRNA viruses, (+)ssRNA viruses, (−)ssRNA viruses, ssRNA-RT viruses, dsDNA-RT viruses, and combinations thereof. Non-limiting examples of viruses repelled by SLIPS include cytomegalovirus (CMV), dengue, Epstein-Barr, Hantavirus, human T-cell lymphotropic virus (HTLV I/II), Parvovirus, hepatitides (e.g., hepatitis A, hepatitis B, and hepatitis C), human papillomavirus (HPV), human immunodeficiency virus (HIV), acquired immunodeficiency syndrome (AIDS), respiratory syncytial virus (RSV), Varicella zoster, West Nile, herpes, polio, smallpox, yellow fever, rhinovirus, coronavirus, Orthomyxoviridae (influenza viruses) (e.g., Influenzavirus A, Influenzavirus B, Influenzavirus C, Isavirus and Thogotovirus), and combinations thereof.

In still another embodiment, SLIPS is capable of repelling particles in suspension or solution without causing surface adhesion, surface-mediated clot formation, fouling, or aggregation. The omniphobic nature of SLIPS allows it to protect surfaces from a wide range of contaminants. Non-limiting examples of a particles in suspension or solution include cells (e.g., normal cells, diseased cells, parasitized cells, cancer cells, foreign cells, stem cells, and infected cells), microorganisms (e.g., viruses, virus-like particles, bacteria, bacteriophages), proteins and cellular components (e.g., cell organelles, cell fragments, cell membranes, cell membrane fragments, viruses, virus-like particles, bacteriophage, cytosolic proteins, secreted proteins, signaling molecules, embedded proteins, nucleic acid/protein complexes, nucleic acid precipitants, chromosomes, nuclei, mitochondria, chloroplasts, flagella, biominerals, protein complexes, and minicells).

In other embodiments, SLIPS repels natural and synthetic solutions used in medicines, intravenous solutions, pharmaceutical manufacturing, and medication delivery systems.

Prevention of or Reduction Protein Adsorption

In one embodiment, SLIPS is used to prevent or reduce protein adsorption.

Biocompatibility and contamination issues associated with the contact of foreign surfaces involve nonspecific protein adsorption. Biocompatibility is the ability of a material to allow an appropriate host response in a specific environment or application. In general, foreign surfaces of medical instruments and medical devices attract a variety of biological adsorption events and biological responses, and it is very difficult to prevent, reduce, or control these processes (Ratner (Ed.), *Biomaterials Science*, Academic Press (2004)). There is a complex variety of biological responses to foreign surfaces, in vivo and ex vivo, associated with biofouling events, immune response, protein adsorption, thrombus formation, and the like (Ratner (Ed.), *Biomaterials Science*, Academic Press (2004)). Proteins have an inherent tendency to deposit on surfaces as a tightly bound adsorbate, which strongly influences subsequent cellular (or microbial) interactions with the surface (Ratner (Ed.), *Biomaterials Science*, Academic Press (2004)). Bacteria attach to surfaces by means of a conditioning layer of proteins. Implanted biomaterials or medical devices are rapidly coated by constituents of the blood serum and surrounding matrix, which include fibronectin, osteonectin, vitronectin, albumin, fibrinogen, laminin, collagen and covalently-bound short-chain oligosaccharides (Ratner (Ed.), *Biomaterials Science*, Academic Press (2004); Gristina, A. G., et al., Biomaterial-centered sepsis and the total artificial heart. Microbial adhesion vs tissue integration. *JAMA* 259:870-874 (1988)). Both bacteria and tissue cells can then attach to these various proteins.

Protein adsorption also occurs when devices trigger an immune response in the body. When the immune response is triggered, complement proteins opsonize the foreign surface for phagocytosis. Complement activation leads to deposition of complement components, which foul the foreign surface (Skattum L, et al., *Mol. Immunol.*, 48(14):1643-55 (2011)).

To date, surface modifications such as the attachment of antithrombotic agents (heparin) or the immobilization of polyethylene oxide (PEO) or polyethylene glycol (PEG) have been thoroughly tested, but their success at avoiding protein adsorption remains limited (George, P. A., et al., J. J. Self-assembling polystyrene-block-poly(ethylene oxide) copolymer surface coatings: resistance to protein and cell adhesion. Biomaterials 30: 2449-2456 (2009)). Although PEG-based surfaces resist non-specific protein adsorption and cell adhesion, they eventually oxidize in most biochemical environments (Ratner (Ed.), *Biomaterials Science*, Academic Press (2004); Chen, S., et al. Surface hydration: Principles and applications toward low-fouling/non-fouling biomaterials. *Polymer* 51:5283-5293 (2010)). The non-fouling properties of antifouling materials is generally caused by a tightly-bound water layer acts as a physical and energetic barrier to protein adsorption. Chen, S., et al. *Polymer* 51:5283-5293 (2010). However, these surfaces eventually deteriorate and allow adsorption to occur.

Thus, in one or more embodiments, SLIPS can be used to prevent or reduce adsorption of proteins that come into contact with SLIPS.

Preventing or Reducing Adhesion of Biological Fluids

Fluids such as biological fluids that are applied to, or come into contact with, SLIPS are strongly repelled by the lubricating fluid. As used herein, "fluids" includes fluids and particles in suspensions or solution, including those from living organisms and synthetic solutions used in medicines.

This surface design represents a completely new approach to controlling the adhesion of biological fluids. Non-limiting examples of biological fluids that can be repelled by SLIPS without causing surface adhesion or aggregation include whole blood, serum, plasma, water, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, synthetic fluid (e.g., synthetic blood, hormones, nutrients), and combinations thereof.

Applications for SLIPS

Anticoagulation Surface

Surfaces that prevent or reduce blood coagulation by repelling blood components, such as platelets and fibrin, involved in the clotting cascade mechanism, can be made in accordance with the present disclosure. In one embodiment, SLIPS is applied to a medial device that comes into contact with complex fluids such as blood to create an anti-coagulation surface. Blood clotting on synthetic surfaces is a long-standing and widespread problem in medicine (Thompson, A. R. & Harker, L. A. *Manual of Hemostasis and Thrombosis*, (F. A. Davis, Philadelphia, 1983); Colman, R. W., Hirsch, J., Marder, V. J. & Salzman, E. W. (eds.). *Hemostasis and Thrombosis*, (Lippincott Williams and Wilkins, 2005)). Thrombosis is initiated on surfaces first by protein absorption, which promotes platelet adhesion, activation and release of thrombin that cleaves fibrinogen and activates fibrin clot formation ((Thompson, A. R. & Harker, L. A. *Manual of Hemostasis and Thrombosis*, (F. A. Davis, Philadelphia, 1983); Colman, R. W., Hirsch, J., Marder, V. J. & Salzman, E. W. (eds.). *Hemostasis and Thrombosis*, (Lippincott Williams and Wilkins, 2005))).

Results demonstrate that SLIPS does not allow blood to wet, and adhere to, SLIPS. Anti-coagulant surfaces that prevent or reduce blood coagulation can be developed by creating an ultra-low drag clot-free surface, much like living endothelium does (see Example 2).

Anti-coagulation surfaces disclosed herein represent a novel and surprisingly effective method for controlling the adhesion of blood components, such as platelets and fibrin, involved in the clotting cascade mechanism. Anti-coagulation surfaces do not allow blood to wet, or adhere to, SLIPS by creating an ultra-low drag clot free surface, much like living endothelium does. FIG. 1 shows the porous or rough layer with the low surface energy, chemically inert, perfluorinated liquid, infiltrated around it. The perfluorinated oil may be held in place by the features of SLIPS structures. This combination leads to a physically smooth, ultra-repellant, and chemically homogeneous lubricating film on the surface of the substrate because the porous structure holds the low energy fluid in place. The presence of the physical roughness of the porous material not only induces the complete wetting of the lubricating fluid, but can also provide additional adhesion for the lubricating fluid within the porous solid. Thin lubricating film minimizes surface inhomogeneities, reduces retention forces, and enhances fluid mobility along SLIPS, not unlike the lipid bilayer in the endothelial cell membrane. As a result, the drag forces on fluid in contact with SLIPS are minimal, and the fluid remains highly mobile on SLIPS. The lubricating film is generated through a fluid infiltration process induced by the porous materials.

In one or more aspect of the disclosed embodiments, SLIPS supports blood flow at 100 mL/hr for 1, 2, 3, 4, 5, or 10 hours or more without platelet activation or clotting. In other aspects, SLIPS supports blood flow at 500 mL/hr for 8, 10, 15, or 20 hours or more without platelet activation or clotting. In still other aspects, SLIPS supports blood flow at 1000 mL/hr for 12, 15, 20, or 24 hours or more without platelet activation or clotting. In other aspects, SLIPS supports blood flow at 1250 mL/hr for 24, 36, or 48 or more hours without platelet activation or clotting. In still other aspects, SLIPS supports blood flow at 1250 mL/hr for a period of days, months, or years.

Medical Devices

In other embodiments, SLIPS is incorporated into medical devices to prevent or reduce adhesion of proteins, microbes, blood, tissue, and the like.

Foreign surfaces associated with medical devices used in biomedical environments are commonly contaminated with bacterial, viral, and fungal microorganisms. Contaminated medical-device surfaces can develop into persistent biofilm infection, and cause infection in other places of the body (Ratner (Ed.), *Biomaterials Science*, Academic Press (2004)). Currently, there are no materials that can prevent, delay, or reduce biological processes associated with protein adsorption, bacterial attachment, and inflammation response. Many materials or coatings, such as heparinized surfaces and Teflon (PTFE), prevent biochemical attachment and response by chemical or biochemical means. Because such materials and coatings rely on chemical or biochemical means to prevent biochemical attachment and response, the use of these materials is limited to certain environments. Moreover, the ability of these materials to repel fluids is limited to certain biological species.

Medical devices and biomedical implants in the body can cause injury to the tissue surrounding the device or implant. Inflammation, wound healing, plaque disposition, and foreign body response are common reactions to these injuries. Medical devices and implants can cause chronic inflammation, formation of granulation tissue, and an end-stage healing response of fibrosis or fibrous encapsulation (Ratner (Ed.), *Biomaterials Science*, Academic Press (2004)). However, no device or coating exists that prevents these injuries from occurring.

Various attempts have been made to coat catheter surfaces with nontoxic antiseptic or antimicrobial drug, or to incorporate such a substance into the catheter material itself (Crnich et al., 2002). These anti-bacterial surfaces have been based on the principle of incorporating compounds such as Ag-particle composite structures, antiseptics, and antibiotics. However, these approaches are ultimately limited in their effectiveness due to the limitations antibiotic species to diffuse from the material, as demonstrated in the large number of infections associated with medical instruments (Crnich 2002, Gristina 1987).

For example, catheters, cannulas, and shunts are commonly used inside and outside the body to allow drainage, administration of fluids or gases, or access by surgical instruments. They can be temporary or permanent (e.g., indwelling catheter). These medical devices can be made of a range of polymers, including silicone rubber, latex, and thermoplastic elastomers. Bacterial infection and colonization of catheters and cannulas and shunts often cause serious related medical conditions such as sepsis (Crnich, C. J. & G. Maki, D. G. The Promise of Novel Technology for the Prevention of Intravascular Device-Related Bloodstream Infection. II. Long-Term Devices. *Clinical Infectious Diseases* 34:1362-1368 (2002)).

Other problems include inflammation and wound response. Stents commonly fail or malfunction because of infection or clogging (Tuli, S., Drake, J., Lawless, J., Wigg, M. & Lamberti-Pasculli, M. Risk factors for repeated cerebrospinal shunt failures in pediatric patients with hydrocephalus. *J. Neurosurg.* 92:31-38 (2000); Noetzel, M. J. & Baker, R. P. Shunt fluid examination: risks and benefits in the evaluation of shunt malfunction and infection. *J. Neurosurg.* 61:328-332 (1984)).

Further, stents are also prone to bacterial contamination that can cause serious infections in the body. A stent is inserted into a natural passage or conduit in the body to prevent or counteract a disease-induced, localized flow constriction. It can also be used to temporarily hold a natural conduit open during surgery. Stents are often heparinized to reduce thrombosis and the effects of bacterial infection. However, despite this precaution, problems associated with clot formation, infection, wound response, and bacterial colonization persist (Garg, N., Garg, R., Gordon, C., Singh, R. & Singh, A. Acute Coronary Syndrome Caused by Coronary Artery Mycotic Aneurysm Due to Late Stent Infection Localized With Radiolabeled Autologous Leukocyte Imaging. *Clin. Nucl. Med.* 34:753-755 (2009); Dieter, R. S. Coronary artery stent infection. *Catheter. Cardio. Inte.* 62:281-281 (2004); Dieter, R. S. Coronary artery stent infection. *Clin. Cardiol.* 23:808-810 (2000); Hearn, A. T., et al. Endovascular stent infection with delayed bacterial challenge. *American Journal of Surgery* 174:157-159 (1997)).

Still other medical devices and implants cause problems associated with adhesion and attachment. Artificial heart valves, ventricular assist devices (VAD), and total artificial hearts (TAHs) often cause bacterial infection, endocarditis, and general inflammation (Cribier, A., et al. Percutaneous transcatheter implantation of an aortic valve prosthesis for calcific aortic stenosis—First human case description. *Circulation* 106:3006-3008 (2002), Dismukes, et al. Prosthetic valve endocarditis. Analysis of 38 cases. *Circulation* 48:365-377 (1973); Karchmer, A. W., et al. *Staphylococcus epidermidis* causing prosthetic valve endocarditis: microbiologic and clinical observations as guides to therapy. *Ann*

*Intern Med* 98:447-455 (1983); Gristina, A. G., et al. Biomaterial-centered sepsis and the total artificial heart. Microbial adhesion vs tissue integration. *JAMA* 259:870-874 (1988)).

Adhesion, attachment, and wound responses often occur when biosensors and bioelectrodes are implanted in the body. The useful life of in vivo biosensors is typically limited due to infection, fouling, and inflammatory response (Wilson, G. S. & Gifford, R. Biosensors for real-time in vivo measurements. *Biosens. Bioelectron.* 20:2388-2403 (2005); Reichert, W. M., Koschwanez, H. E., Yap, F. Y. & Klitzman, B. In vitro and in vivo characterization of porous poly-L-lactic acid coatings for subcutaneously implanted glucose sensors. *Journal of Biomedical Materials Research Part A* 87A:792-807 (2008); Munro, W. A., Thomas, C. L. P., Simpson, I., Shaw, J. & Dodgson, J. Deterioration of pH electrode response due to biofilm formation on the glass membrane. *Sensor Actuat B-Chem* 37:187-194 (1996)).

Also, pacemakers, and bioelectrodes, such as neural electrodes, also face frequent problems of infection, fouling and inflammatory response (S. Karnam, et al. *Mycobacterium phlei*, a previously unreported cause of pacemaker infection: Thinking outside the box in cardiac device infections. *Cardiology Journal* 17 (2010); Sohail, M. R., et al. Risk factor analysis of permanent pacemaker infection. *Clin Infect Dis* 45:166-173 (2007)).

Endoscopes are difficult to clean and sterilize, and therefore present issues related to the transfer of bacterial, fungal, or viral infection from one patient to another (Beilenhoff, U., et al. ESGE-ESGENA guideline: Cleaning and disinfection in gastrointestinal endoscopy Update 2008. *Endoscopy* 40:939-957 (2008); Banerjee, S., et al. Infection control during GI endoscopy. *Gastrointest Endosc* 67:781-790 (2008)). Further, endotracheal tubes, ventilators, and associated ventilator tubing are typically contaminated with persistent bacterial biofilms, and thus require frequent cleaning and replacement (Afessa, B., et al. Association Between a Silver-Coated Endotracheal Tube and Reduced Mortality in Patients With Ventilator-Associated Pneumonia. *Chest* 137: 1015-1021 (2010)).

Additionally, the success of implanted in vivo drug delivery devices is often limited by biofouling processes within the body, which reduces effectiveness of drug delivery (Bhardwaj, U, et al. A review of the development of a vehicle for localized and controlled drug delivery for implantable biosensors. *J Diabetes Sci Technol* 2:1016-1029 (2008); Voskerician, G., et al. Biocompatibility and biofouling of MEMS drug delivery devices. *Biomaterials* 24:1959-1967 (2003)).

SLIPS are used to prevent, reduce, or delay various fluids and other biological materials from wetting surfaces and particles from adhering to surfaces. For example, SLIPS can be incorporated into a microfluidic device, which controls the flow of minute amounts of fluids or gases (e.g., a lab-on-a-chip), for manipulating biological fluids. SLIPS surfaces are useful for preventing, reducing, or delaying inflammatory responses, blood coagulation, antifouling, and adhesion of other products of biological origin in and on devices including wound dressings catheters, stents, and other biomedical devices (e.g., stents, dialysis machines, central veno-venous hemofiltration device, extracorporeal membrane oxygenation equipment, and linking catheters), so that devices can support flow of fluids without permitting wetting of fluids, attachment, or adhesion of particles (see, e.g., FIG. 22A-B). Surfaces of medical instruments and medical devices attract a variety of biological adsorption events and biological responses that are difficult to prevent, reduce, and control. SLIPS can be applied to medical instruments and medical devices to reduce, prevent, or mediate processes associated with protein adsorption, cell attachment, bacterial infection, and inflammatory response.

For example, SLIPS can be used in wound care, including wounds caused by, e.g., cuts, bruises, punctures, scrapes, tears, and burns. In one embodiment, SLIPS is used to prevent or reduce further damage to damaged skin and to oxygenate the tissue that the SLIPS surface covers. One aspect of this embodiment is burn wound care. Burn wounds become hypoxic because of the layer of damaged tissue. Current burn treatments involve exposing the damaged tissue to high levels of oxygen. This can be accomplished in, e.g., a hyperbaric chamber. However, such wounds must either be covered by a wound dressing, which prevents or reduces the damaged tissue from being exposed to much needed oxygen, or be left exposed and vulnerable to infection. A SLIPS-treated wound dressing that has been infused with oxygenated lubricating fluid can be used to both protect the wound from infection caused by exposure to the environment without adhering to the wound, and provide the wound with oxygen to promote healing.

Medical/Surgical Instruments

An important consequence of bacterial contamination and population of surfaces is the infection of surgical instruments, biomedical materials and prosthetics such as catheters (Costerton, J. W., et al. Bacterial biofilms in nature and disease. *Ann. Rev. Microbiol.* 41:435-464 (1987); Gristina, A. G., Dobbins, J. J., Giammara, B., Lewis, J. C. & DeVries, W. C. Biomaterial-centered sepsis and the total artificial heart. Microbial adhesion vs tissue integration. *JAMA* 259: 870-874 (1988)). Bloodstream infection caused by surgical instrument-related bacterial contamination is a frequent and serious complication associated with procedures involving catheters and implants (Costerton et al., 1987; Gristina, 1988). Such infections trigger an immune response in the body, which can lead to inflammation of the infection site.

Surgical instruments and intravascular devices (IVD) such as catheters have many potential sources for infection. The adherence of microorganisms to catheter surfaces is among the most important characteristics associated with the pathogenesis of infection caused by catheter use. Even a single bacterium cell that successfully adheres to surface can develop into a robust and infectious bacterial film and cause disease. Therefore an effective strategy for prevention or reduction of bacterial adhesion is needed.

Wound Dressings

Figure 23:
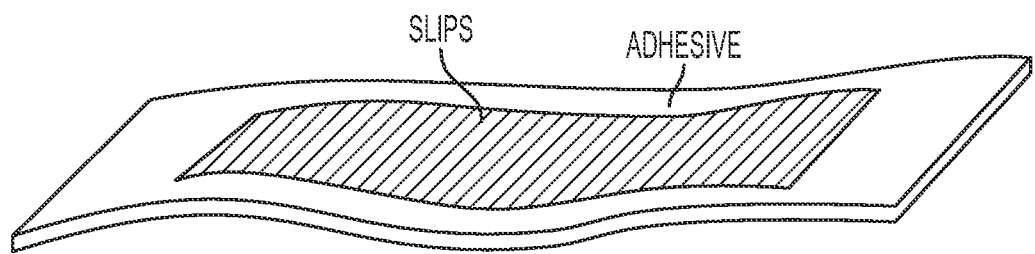
FIG. 23 is a schematic of a wound dressing with SLIPS.

In another embodiment, SLIPS is incorporated into a wound dressing. SLIPS surfaces do not permit adhesion of proteins or cells when contacted with biological fluids. Moreover, perfluorocarbons have a high solubility for oxygen (Clark, Leland C.; Gollan, F. *Science* 152(3720):1755-56 (1966); Shaffer, T. H. et al., *Pulmonol.* 14:102-109 (1992)). Thus, a wound dressing that incorporates SLIPS with, e.g., a perfluorocarbon substrate, provides a breathable surface that prevents adhesion of proteins or cells to promote faster wound healing (see, e.g., FIG. 23).

EXAMPLES

The following examples are presented for the purpose of illustration only and are not intended to be limiting.

Example 1

Figure 15:
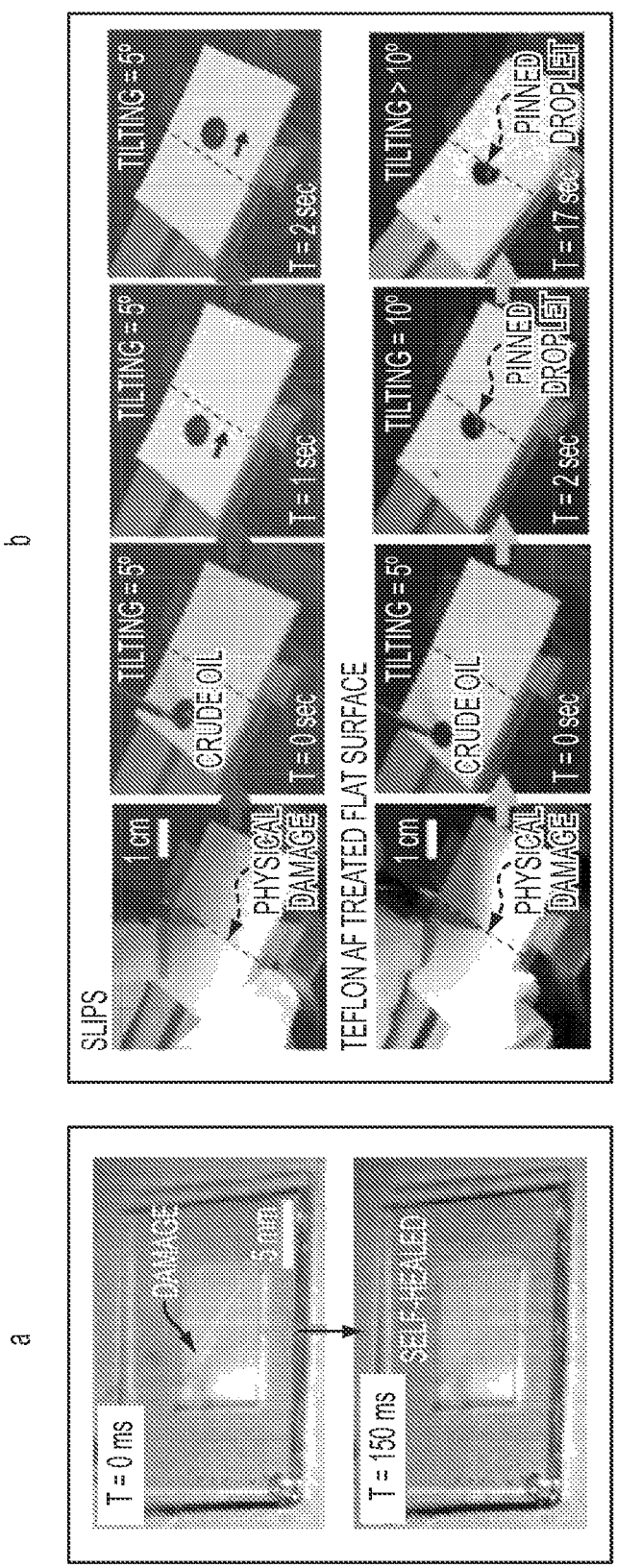
FIG. 15 is a series of images showing the self-healing and optical transparency properties of SLIPS. 15A. Time-lapse images showing self-healing capability of SLIPS from a ~50 μm-wide physical damage on a time scale on the order of 100 ms. 15B. Time-lapse images showing the restoration of liquid repellency of SLIPS after physical damage, as compared to a typical hydrophobic flat surface on which oil remains pinned at the damage site.
Figure 17:
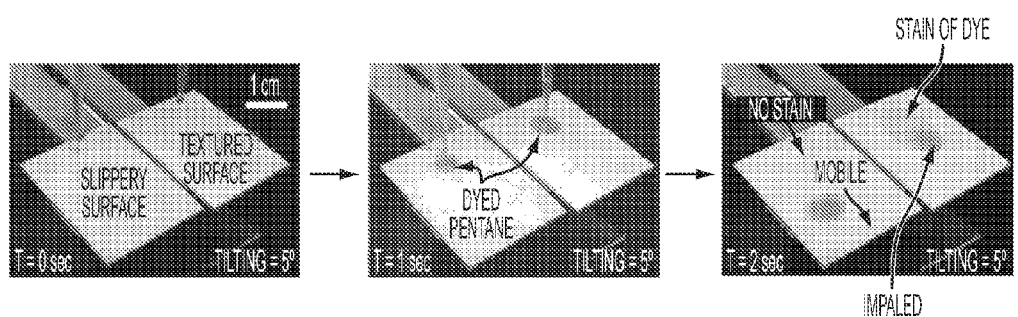
FIG. 17 is a series of images showing the omniphobicity and high pressure stability of SLIPS. Time sequence images comparing mobility of pentane droplets ($\gamma_A$=17.2±0.5 mN/m, volume≈30 μL) on a SLIPS and a super hydrophobic, air-containing Teflon porous surface. While pentane is repelled on the SLIPS, it wets and stains the traditional super hydrophobic surface.

A set of SLIPS was fabricated to repel fluids spanning a broad range of surface tensions. To generate roughness, two types of porous solids were tested. The porous solids were periodically ordered and random: (i) arrays of nanoposts functionalized with a low-surface-energy polyfluoroalkyl silane, and (ii) a random network of Teflon nanofibres distributed throughout the bulk substrate (FIG. 17). Low-surface-tension perfluorinated liquids (e.g. FC-70, $\gamma_B$=17.1 mN/m; or Dupont™ Krytox® oils) that are non-volatile and immiscible with both aqueous and hydrocarbon phases and therefore able to form a stable, slippery interface with substrates (i.e., $E_1$>0 and $E_2$>0) for a variety of polar and non-polar liquids including water, acids and bases, alkanes, alcohols, and ketones (FIG. 15 and FIG. 17) were chosen for the lubricating fluid. The SLIPS were generated through liquid infiltration into the porous materials, which resulted in a homogeneous and nearly molecularly smooth surface with a roughness of ~1 nm.

Figure 18:
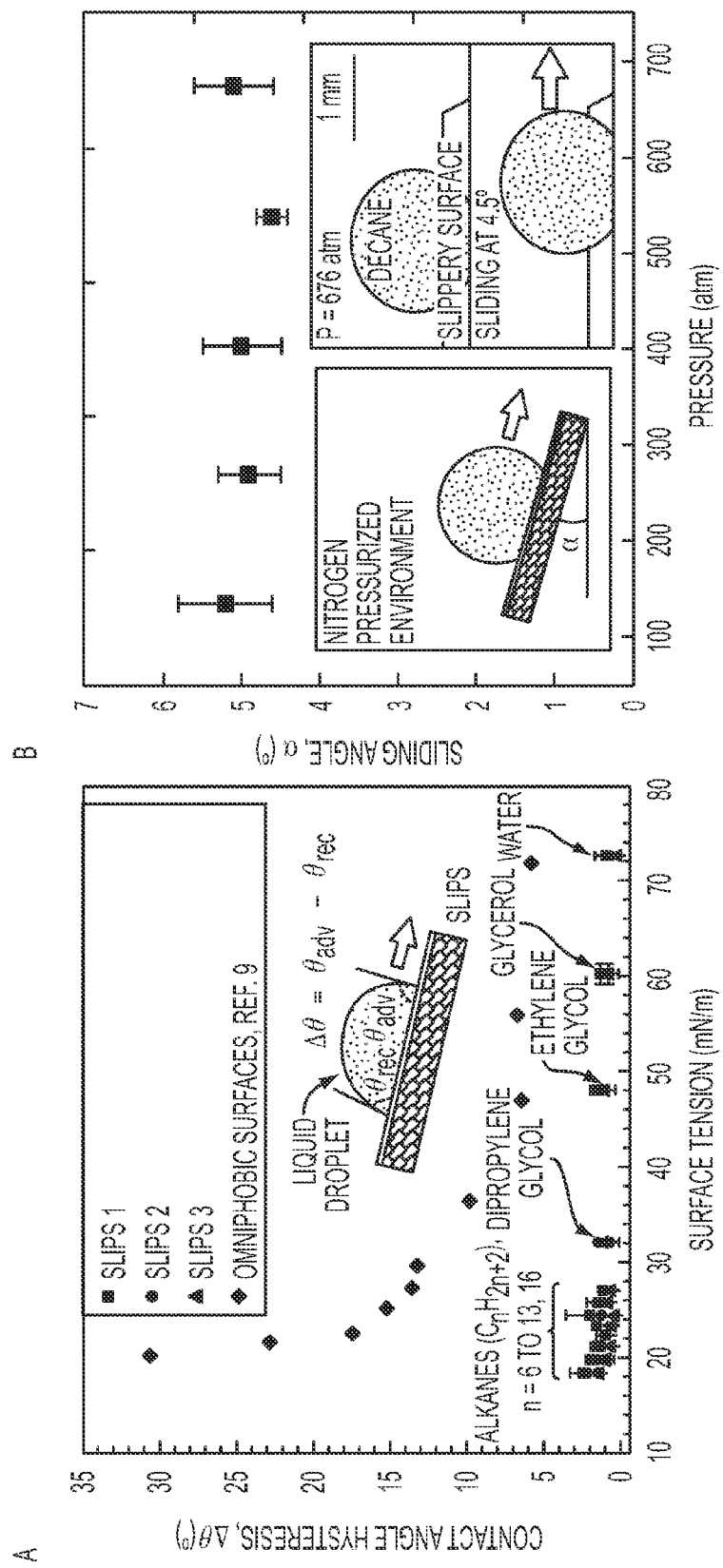
FIG. 18 is a set of graphs showing the contact angle hysteresis as a function of surface tension of test liquids (indicated) on SLIPS and on an omniphobic surface. In the inset (18A), advancing and receding contact angles of a liquid droplet are denoted as $\theta_{adv}$, and $\theta_{rec}$, respectively. SLIPS 1, 2, and 3 refer to the surfaces made of 1) Teflon porous membrane, 2) array of epoxy posts of geometry 1 (pitch=2 μm; height=5 μm; and post diameter=300 nm), and 3) array of epoxy posts of geometry 2 (pitch=900 nm; height=500 nm to 2 μm; and post diameter=300 nm), respectively. A plot (18B) showing the high pressure stability of SLIPS, as evident from the low sliding angle of a decane droplet ($\gamma_A$=23.6±0.1 mN/m, volume≈3 μL) subjected to pressurized nitrogen gas in a pressure chamber. Error bars indicate standard deviations from at least seven independent measurements.

Each of these SLIPS exhibited extreme fluid repellency as signified by very low contact angle hysteresis (CAH, $\Delta\theta$<2.5°, FIG. 17 and FIG. 18A) and by very low sliding angles ($\alpha \leq 5°$ for droplet volume≥2 μL) against fluids of surface tension ranging from ~17.2±0.5 mN/m (i.e., n-pentane) to 72.3±0.3 mN/m (i.e., water). CAH, the difference between the advancing and receding contact angles of a moving droplet, and sliding angle, the surface tilt required for droplet motion, directly characterize resistance to mobility; the low values therefore confirm a lack of pinning, consistent with a nearly defect-free surface. Based on the measured CAH and droplet volume (~4.5 μL), the estimated fluid retention force on SLIPS was 0.83±0.22 μN, n=6. This performance was nearly an order of magnitude better than the state-of-the-art lotus-leaf-inspired omniphobic surfaces, whose fluid retention forces are of the order of 5 μN for low-surface-tension fluids (i.e., $\gamma_A$<25 mN/m) at similar fluid volumes. Moreover, the fluid-repellency of SLIPS was insensitive to texture geometry (FIG. 18A), provided that the lubricating layer covered the textures. Additionally, unlike lotus-based omniphobic surfaces where CAH depends on fluid surface tension and increases dramatically upon decrease of surface tension (FIG. 18A), such a dependence was absent for SLIPS due to the chemical homogeneity and physical smoothness of the fluid-fluid interface.

Example 2

The disclosed surfaces provide an ultra-smooth surface capable of preventing, reducing, or delaying surface wetting of fluids that come into contact with SLIPS.

Figure 11:
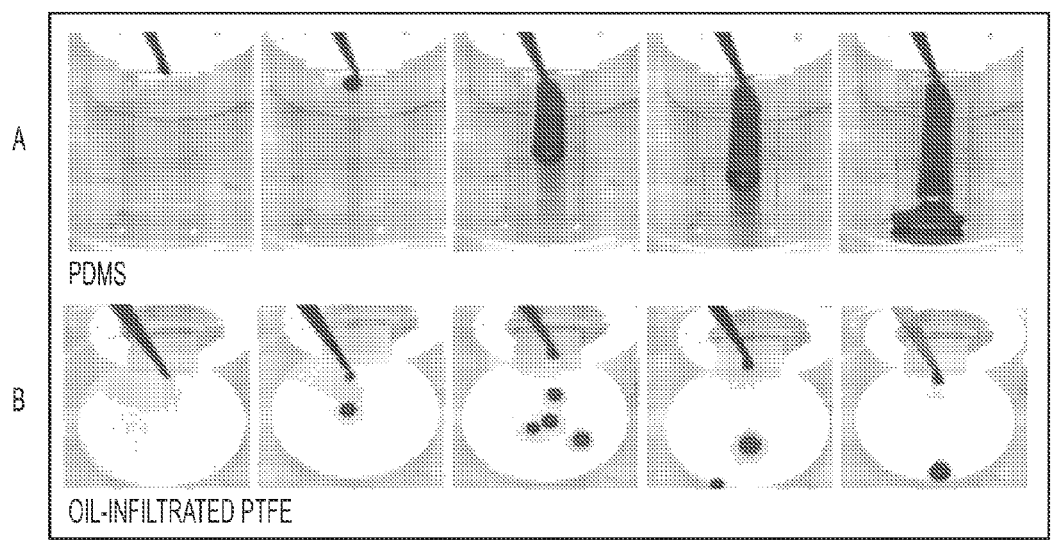
FIG. 11 shows sequential images of whole human blood without anticoagulants as it is pipetted onto PDMS (11A) and the oil-infiltrated PTFE (11B) surfaces.
Figure 12:
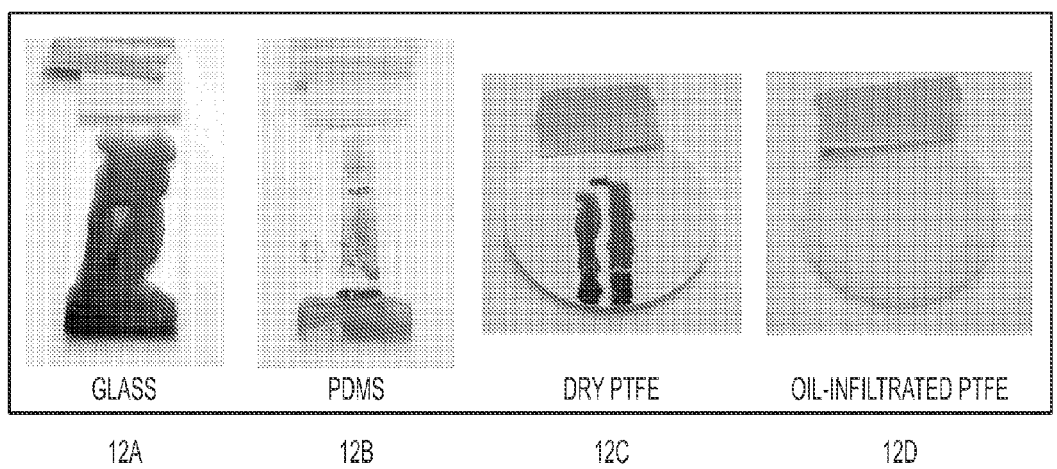
FIG. 12 is a series of images of control and test surfaces after exposure to 0.75 mL of blood flow, which show absorption of blood to the control surfaces (glass (12A), PDMS (12B), dry PTFE (12C)) but no apparent absorption to the oil-infiltrated PTFE (12D).

An experiment was conducted in which the difference in surface adhesion of blood on PDMS was compared to that of an oil-infiltrated PTFE surface. 0.75 mL of fresh whole blood from a human subject was used, without the addition of heparin. The whole blood was pipetted onto four surfaces, one consisted of microstructured PTFE (Teflon; 1 μm pore size) impregnated with perfluorinated oil (FC-70), the second consisted of untreated microstructured PTFE which served as the control, the third surface was untreated glass, and the fourth surface was untreated PDMS. FIG. 11 shows sequential images of the blood sample being added to PDMS (FIG. 11A) and microstructured PTFE impregnated with perfluorinated oil (FIG. 11B). The surfaces made of PDMS (FIG. 11A), microstructured PTFE (FIG. 12D), and glass (FIG. 12A), all allowed the blood sample to wet the surfaces and rapidly coagulate and adhere to these materials. The SLIPS that consisted of microstructured PTFE impregnated with perfluorinated oil (FIG. 11B) caused the blood sample to immediately bead into droplets and slide along SLIPS.

Figure 13:
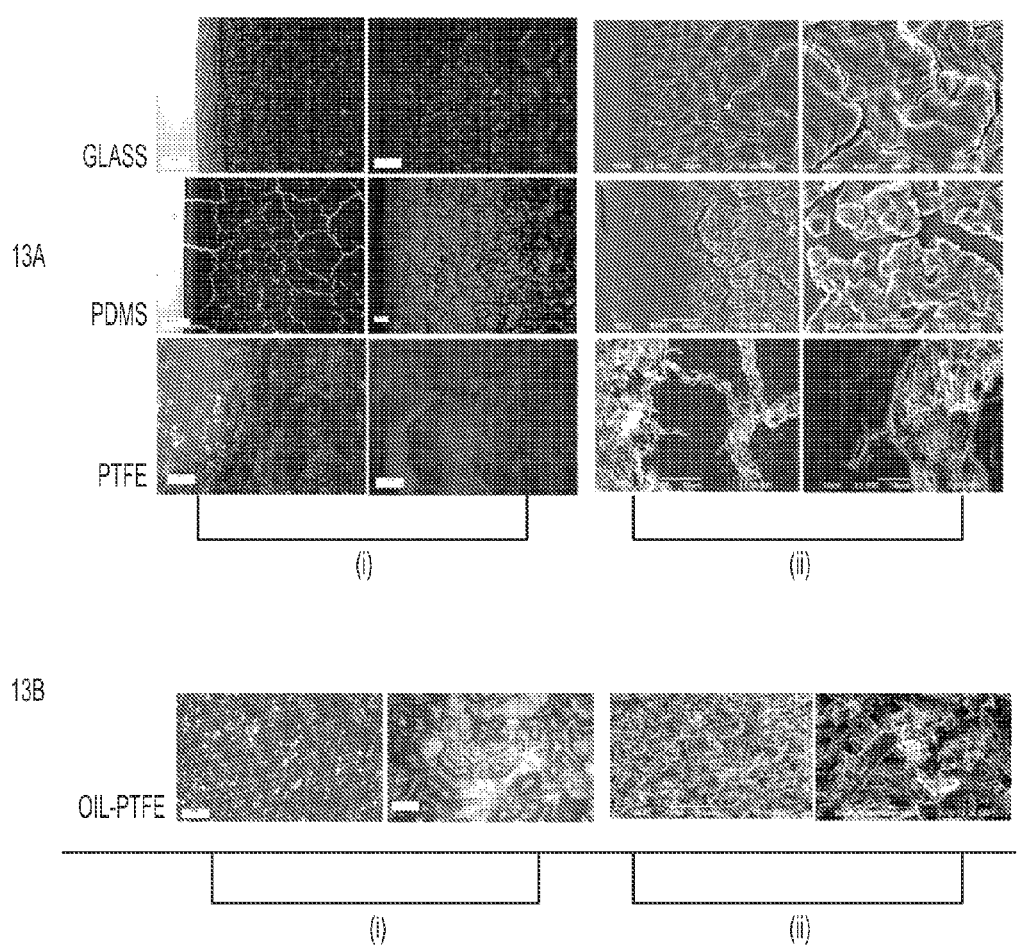
FIG. 13 shows optical (13A(i), 13B(i)) and scanning electron microscope (SEM, 13A(ii), 13B(ii)) surface analysis images of the control and oil-infiltrated PTFE samples from FIGS. 11A and 11B in which all the control materials showed evidence of adhered, dried blood species (a mixture of cells, platelets, proteins, see (13A)), while the oil-PTFE material (13B) showed no evidence of biological material.

Referring to FIG. 13, subsequent analysis of these surfaces using optical (FIGS. 12(A)(i), 12(B)(i)) and scanning (FIGS. 12(A)(ii), 12(B)(ii)) electron microscopy, to show that while blood species such as cells, platelets, and proteins are visibly deposited on the untreated glass, PDMS, and PTFE control surfaces, there is nothing visible on the oil-infiltrated PTFE material. Thus, this 'fluid-like' surface appears to be extremely effective at preventing or reducing adhesion of platelets and fibrin clot formation when in contact with fresh unheparinized human blood.

Example 3

Experiments using 2 μm polystyrene particles showed that force of adhesion to slippery surfaces was extremely low, such that the particles were easily dragged by a fluid/air boundary interface across SLIPS, and concentrated into the center of a drying droplet instead of leaving a 'coffee ring' deposition.

Example 4

Experiments were conducted to determine whether fluid from SLIPS leach into the surrounding biological fluid. A nanostructured post array surface (2 μm tall posts, 300 nm diameter, 0.9 μm spacing) with infiltrated perfluorinated oil (Fluorinert FC-70) was integrated into a microfluidic system. Deionized water flowed into the channel at a rate of 12 mL/min (i.e., 720 mL/hr) for 5 minutes. It was found that the perfluorinated oil remained intact on the nanostructured surface. The slipperiness of the surface was examined by putting a droplet of decane on the surface. If decane applied to the surface maintains its mobility on the surface, then the lubricants remain attached on the structured surface. However, if decane remains pinned on the surface, the lubricant layer has not been maintained. Leaching can also be monitored by extracting fluid that has passed over SLIPS into a fluorinated solvent followed by followed by chromatography and mass spectrometry and 19F-NMR.

Defining maximum leaching of the infiltrated fluid as the ratio between the total amounts of the perfluorinated oil infiltrated the surface and the volume of water processed in the microfluidic system, the maximum leaching was <0.2%. Because perfluorocarbons are already approved by the Food and Drug Administration as blood substitutes, leaching of this amount of oil is expected to be harmless. The effective viscosity can be increased to reduce the amount of leaching while maintaining the 'fluid-like' surface that resists blood clot attachment.

Example 5

The slippery surfaces produced in accordance with the present methods showed excellent prevention of attachment and/or facilitation of low-force detachment of mature bacterial biofilm incubated on the surface. Specifically, this capability is demonstrated for *Pseudomonas aeruginosa*, a human opportunistic pathogen, and one of the most common nosocomial infections in the lining of catheters and the lungs of cystic fibrosis patients.

The surface was fabricated by wicking 100 μL of various commercial fluids satisfying criteria for a lubricating fluid into 30 mm round Teflon filter membranes with 0.2 μm pore size, which were then mounted onto standard polystyrene Petri dishes. Atop the slippery surfaces, 2 mL tryptone broth puddles for 24 hours that were inoculated at 1% with *Pseudomonas aeruginosa* preculture were deposited and statically incubated. The bacteria formed a mature biofilm during this timeframe, and the slime-like matrix binding the constituent cells tends to gel the puddle.

Figure 19:
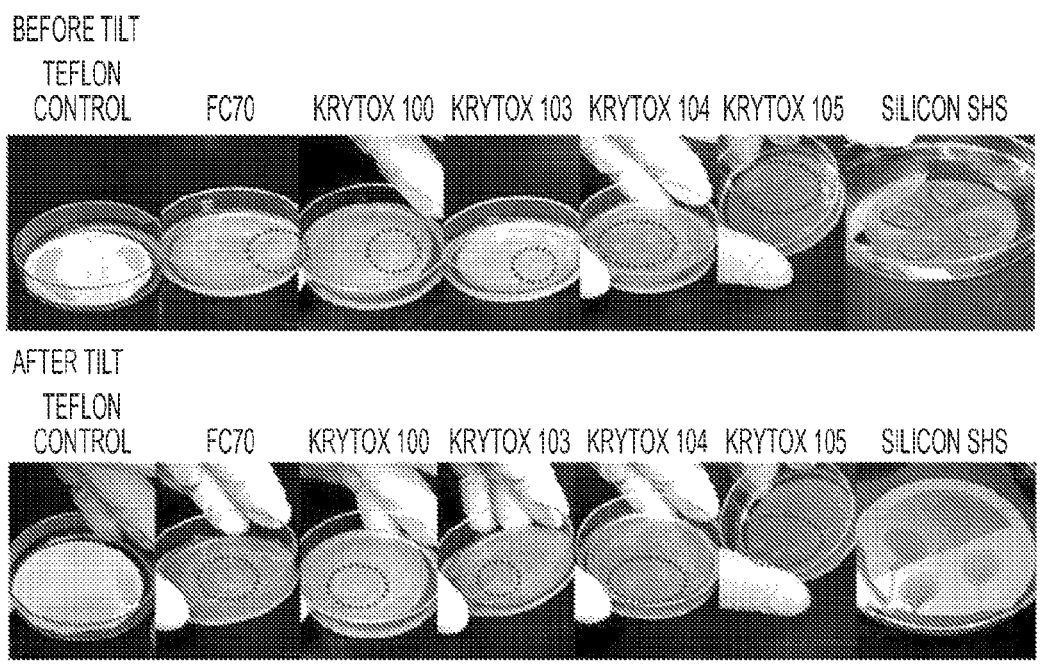
FIG. 19 is a series of images demonstrating low-tilt-angle sliding of *Pseudomonas aeruginosa* (PA14) biofilm growth in 2 mL tryptone broth puddles incubated for 24 hours atop liquid slippery surfaces in accordance with certain embodiments.

The slippery surfaces produced in accordance with the present disclosure caused the slimy mass to readily slide off when tilted, as shown in FIG. 19, even at tilt angles below 10°. The effective slide-off removal of biofilm slime on the slippery surfaces produced in accordance with the present disclosure contrasts to the adhesion and pinning of the basal layer of slime on unfilled 0.2 µm Teflon filters (left of FIG. 19) as well as on fluorosilanized super hydrophobic silicon micro/nanostructure arrays (right of FIG. 19), whose fluid repellency properties failed during the conditioning film and slime production of biofilm.

Figure 20:
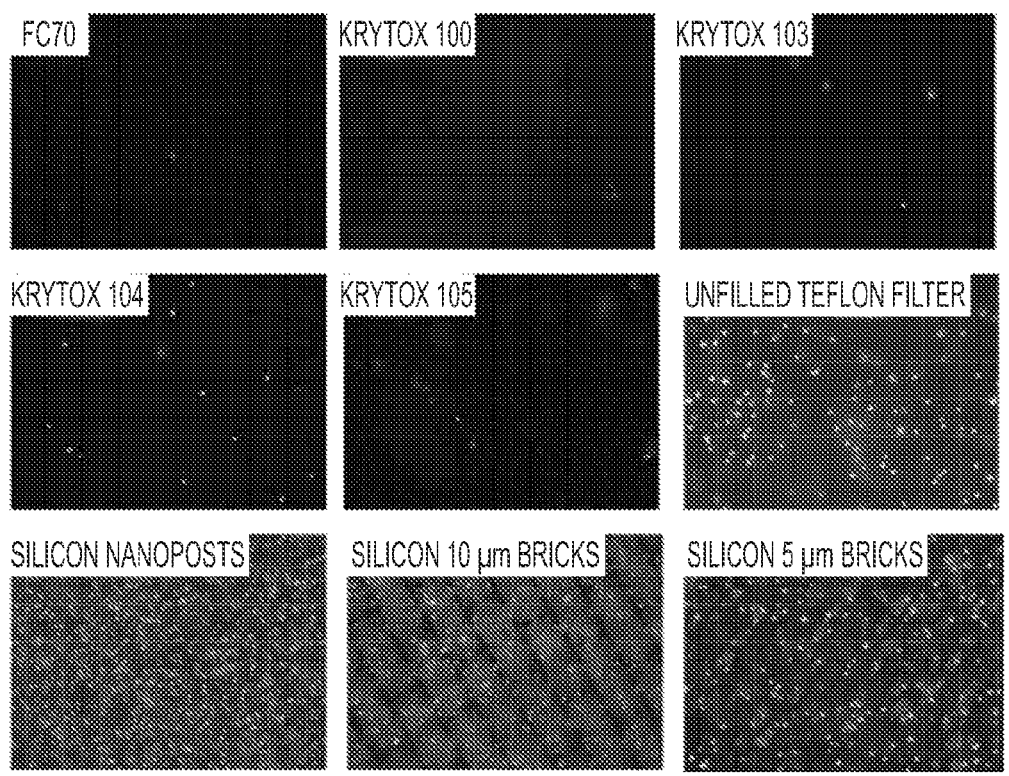
FIG. 20 is a series of fluorescence microscopy images of *Pseudomonas aeruginosa* (PA14) bacteria remaining on various slippery liquid surfaces after 2 mL of shaken culture was incubated for 24 hours on the surfaces and subsequently slid off by applying a tilt angle in accordance with certain embodiments.

In addition to the visually apparent slide-off of biofilm slime, the slippery surfaces produced in accordance with the present disclosure showed nearly no adherent bacteria on the surfaces. Any remaining adherent bacteria was fixed with 5% glutaraldehyde in phosphate buffered saline, permeabilized, and marked with a nucleic acid stain for fluorescent cell imaging. Fluorescent microscopy revealed a lack of biofilm structures or any microcolonies remaining on the slippery surfaces produced in accordance with the present methods following 24 hour incubation, as shown in FIG. 20. In contrast, significant remaining biomass was left on the unfilled 0.2 µm Teflon filters as well as on three different fluorosilanized super hydrophobic silicon micro/nanostructure arrays (submicron posts and 10 µm and 5 µm "brick wall" patterns).

Example 6

Figure 21:
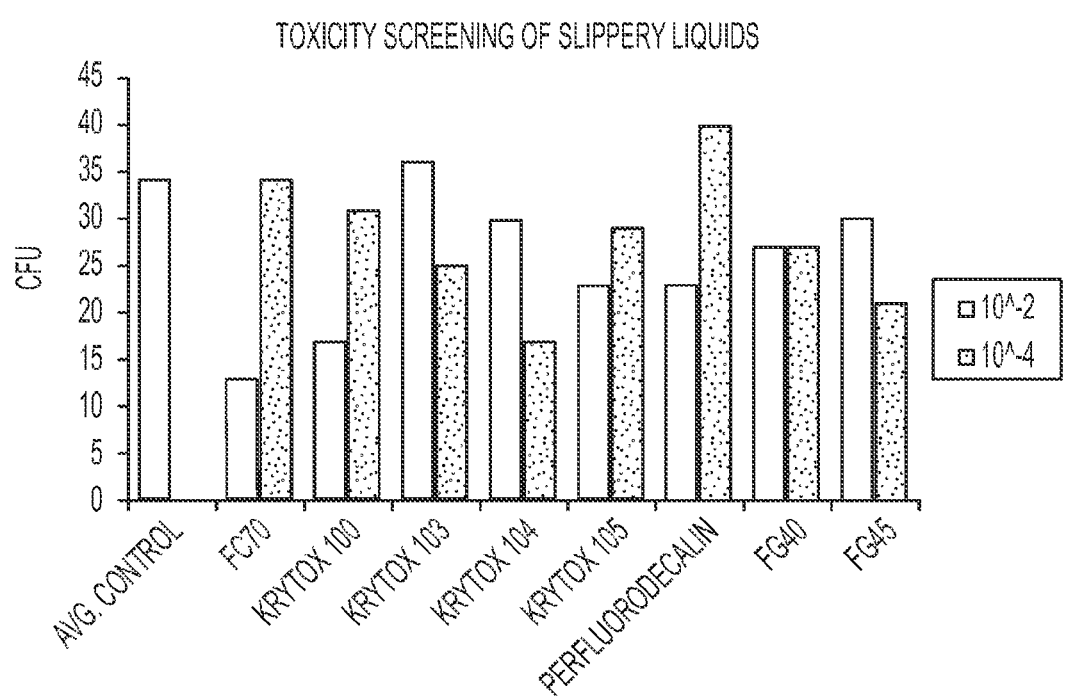
FIG. 21 show a toxicity screening of a number of commercially available products that can satisfy the requirements for the lubricating fluid in accordance with certain embodiments.

The slippery surfaces produced in accordance with the present disclosure can be designed to be nontoxic by appropriate selection of the lubricating fluid, enabling applications with medical and environmental requirements. Among the commercial fluids already available, eight products that can satisfy the requirements for a lubricating fluid were screened and five candidates were identified for low toxicity (see FIG. 21). The toxicity screening assay was based on adding 1% and 0.01% of each commercial product to 10 mL aliquots of tryptone broth, which were inoculated with 1% initial seeding concentration of Pseudomonas aeruginosa (PA-14) preculture and incubated at 37° C. overnight in an orbital shaker. The shaken culture was serially diluted, plated, and incubated for colony forming unit (CFU) quantification. Significantly reduced CFU at the 1% concentration versus 0.01% concentration of FC70, Krytox 100, and Perfluorodecalin indicated an inhibitive effect and screened out these products for toxicity-sensitive applications. The remaining five products—Krytox 103/104/105 and FG40/45—are viable candidates for slippery fluid surfaces designed to minimize bacterial adhesion as well as toxicity.

Example 7

Teflon and silicon wafer SLIPS surfaces prepared in accordance with the present disclosure were shown to prevent bacterial attachment.
SLIPS Fabrication To prepare SLIPS, lubricating liquid (Dupont™ Krytox® 100 and 103) was added onto the porous solids, Teflon membranes with average pore sizes of ≥200 nm and about 60-80 µm thick (Sterlitech Corporation, WA, USA), to form an over-coated layer. The fluid spread spontaneously onto the whole substrate through capillary wicking.

Silicon Microstructure Array Fabrication

Superhydrophobic microstructure arrays were fabricated on a 4" silicon wafer by the Bosch process (M. Sugawara, e.a., *Plasma Etching: Fundamentals and Applications*. Series on semiconductor science and technology. Vol. 7. 1998, New York: Oxford University Press). The microstructures consisted of four types of geometries: d=500 nm HAR nanoposts, 2 µm pitch; d=1 µm HAR microposts, p=3 µm; 5 µm T-shaped microposts; and 10 µm T-shaped microposts. The wafer was rinsed with EtOH, oxygen plasma treated for 30 seconds, and was rendered hydrophobic by putting the sample in a vacuum desiccator overnight with a glass vial containing 0.2 mL heptadecafluoro-1,1,2,2-tetrahydrodecyl-trichlorosilane (Gelest Inc).
Bacterial Preparation and Growth Bacterial strains *Pseudomonas aeruginosa* PA14, *Staphylococcus aureus* SC01, and *Escherichia coli* ZK2686 were each grown in LB medium (EMD LB Broth Miller) overnight at 37° C. in loosely capped tubes on an orbital shaker to the stationary phase. This LB preculture was then seeded at 1% concentration in one of the following: TB growth medium (BD Bacto Tryptone) for *P. aeruginosa*; TSB medium supplemented with 0.5% glucose and 3% NaCl for *S. aureus*; or M9 medium for *E. coli*. These cultures were incubated on the bench at room temperature during experiments.
Flow Cell Setup A Tygon tube of inner diameter ⅛" was mounted in a peristaltic pump (Cole Parmer) and connected via hose barb fittings (World Precision Instruments) to a dual-chamber 3D-printed flow cell (chamber dimensions l=10 cm, w=1 cm, h=1 mm).

The tubing was configured to allow flow in series through the two chambers. The bottom surface and sidewalls of each chamber were lined with press-fit porous Teflon membrane; one was infused with Krytox 103 to create a SLIPS and the other was left untreated as a control. Bacterial culture was pumped into each tube until the loop was full and trapped air had been eliminated though a bubble escape, after which the pump was operated at 10 mL/min.
Toxicity Screening Shaken cultures of 1% *P. aeruginosa* in TB were grown in triplicate with 1% by volume of the following reagents: Krytox 100, Krytox 103, Perfluorodecalin, FC70, bleach, and 0.1% of $AgNO_3$ and glutaraldehyde. Background samples containing only media and reagents were also prepared, as well as control cultures without added reagents. Samples were incubated in an orbital shaker at 37° C. at 200 rpm. Optical density measurements at 550 nm were taken at 3, 6, 9, and 30 hours on a Perkin Elmer Lambda 40 UV-Vis spectrometer. Optical densities were normalized by subtracting backgrounds, i.e., the reagents in TB only.
Imaging and Analysis For fluorescence imaging of attached bacterial cells, the PTFE substrates mounted in the flow cell were removed, gently rinsed in phosphate buffered saline (PBS) (1×) (Lonza Biowhittaker), and the adherent bacteria were fixed by 5% glutaraldehyde solution for at least 1 hour. 0.01% Triton X100 in PBS (PBST) was used to permeabilized the bacteria membranes over 15 minutes, after which the cells were stained with 0.5 µM SYTOX green nucleic acid stain (Invitrogen) in PBST for 30 minutes. Imaging was performed on a Leica DMX microscope.

To analyze the fluorescence intensity of the micrographs from the control and SLIPS flow cell substrates, the average intensity image of each sample's micrograph set was generated in ImageJ and the average [(R+G+B)/3] pixel value and standard deviation were computed for each average intensity image.

Biofilm Quantification by Crystal Violet Staining

PTFE substrates were carefully sectioned with a scalpel into 3×3 cm segments, removed from the flow cell, gently rinsed in PBS, and stained by 0.1% crystal violet for 20 minutes. The stained samples were rinsed in a DIW bath and the bound crystal violet on each was eluted into 4 mL of 100% EtOH. Absorbance values at 590 nm were measured on a Perkin Elmer Lambda 40 UV-Vis spectrometer.

Prevention of Biofilm Attachment/Formation

In a simple test scheme, Pseudomonas aeruginosa TB culture was deposited in puddles that were statically grown upon three surface typologies, two of which are shown in FIG. 36A. A porous PTFE membrane (0.2 μm pore size) served as a flat, conventional low-adhesive control surface; a fluorosilanized patterned silicon wafer (not shown) featuring four different high-aspect-ratio micropost arrays presented superhydrophobicity, the capacity to repel and roll off water; and a PTFE membrane infused with Krytox-103 provided a SLIPS liquid slippery surface. After 48 hours of room temperature growth, the viable cell concentration of the imposed bacterial cultures on both surfaces was on the order of $10^8$ mL$^{-1}$. The bacteria were fixed and stained, and the fluorescence micrographs of resulting growth are shown in FIG. 36A, insets. While robust and uniform biofilm coverage was observed on both flat PTFE and superhydrophobic silicon (not shown), only sparse and isolated cells were seen on the SLIPS (see, e.g., FIG. 36C).

The test surfaces were manually tilted to compare the adhesion of the macroscopic biofilm slime. Biofilm grown on the control and superhydrophobic substrates showed complete wetting of the surface and left a film of slime on the PTFE as it was tilted. In contrast, biofilm on the SLIPS substrate slid readily without leaving any slime film or other visible residue behind. Biofilm growing in contact with the bare polystyrene Petri dish at the edge of the SLIPS remained pinned. However, it was not attached to the SLIPS substrate underneath: when part of the pinned puddle was disconnected from the edge and manipulated toward the center, it became fully mobile.

The contact line pinning characteristics of the surfaces (i.e., SLIPS and porous Teflon) were characterized by monitoring the evaporation dynamics of the bacterial culture droplets as well as the stains that remained on the surfaces upon drying. In the absence of pinning, the droplet should follow a nearly constant contact angle mode of evaporation without the formation of a coffee ring stain.

These hypotheses were consistent with observations of the bacteria droplet's evaporation on SLIPS. The absence of the coffee ring formation also indicated that the adhesion of the bacteria on the SLIPS was small compared to the forces imparted by the meniscus of the droplet, and it was demonstrated that the dried biofilm was easily removed from SLIPS by adhesive tape. In contrast, an evaporating droplet on the porous Teflon was strongly pinned, leading to a constant contact area mode of evaporation which also resulted in the formation of an irremovable coffee ring. These demonstrations of biofilm non-attachment to SLIPS and resisting $3.5\times10^8$ mL$^{-1}$ bacterial liquid were consistent with both macroscopic and microscopic quantification data obtained herein.

Figure 37:
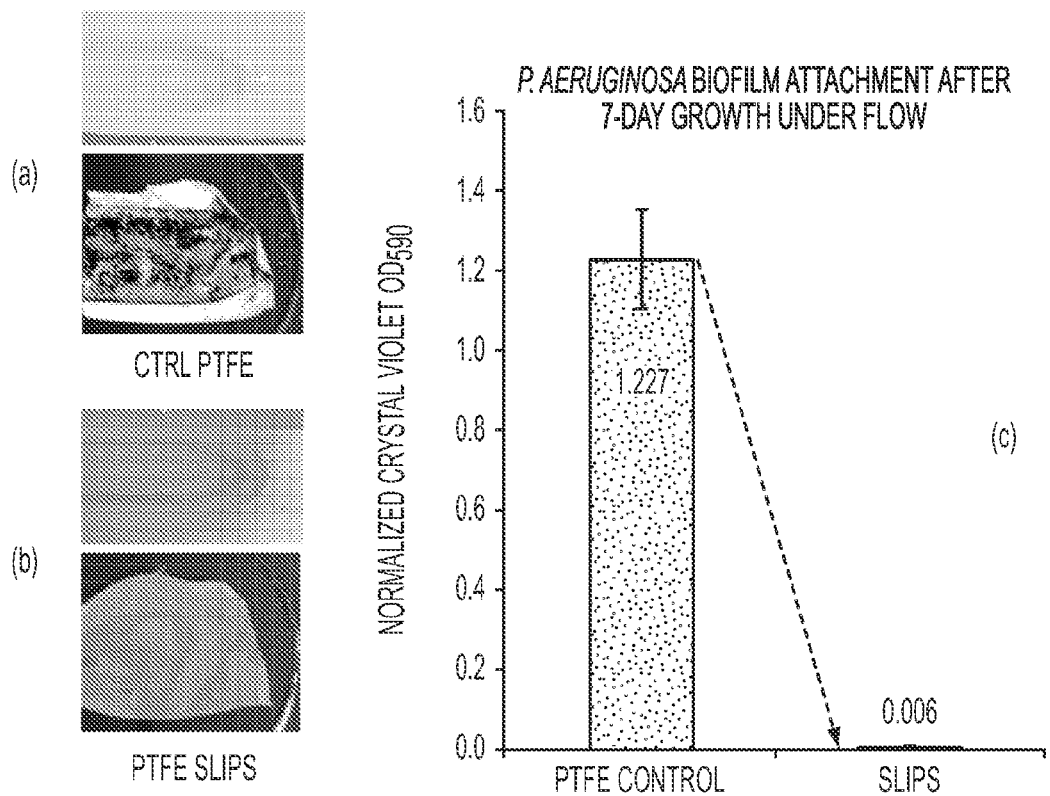
FIG. 37 shows images of a macroscale view of biofilm attachment inhibition on SLIPS. Growth was conducted in a peristaltic pump at 10 mL/min (velocity ~1 cm/s) and dual-chamber 3D-printed flow cells with h=1 mm, l=10 cm, w=1 cm channels. (A-B) Photographs of the control PTFE and SLIPS PTFE substrates after the flow cell was opened following 48 hour growth under 10 mL/min flow, both before crystal violet staining (top) and after (bottom). Equal-area samples of the substrates were eluted for crystal violet quantification, a measurement of attached biomass (C). Following 7 days of growth, crystal violet staining-based quantification showed a 99.6% reduction in attached biofilm on SLIPS versus control PTFE.

Most submerged biofilm formation occurs under various flow conditions, e.g., in plumbing, ship hulls, catheters, and the like. Accordingly, biofilm attachment was studied on test surfaces lining a dual 3D-printed flow cell, through which the bacterial culture was continuously circulated by a peristaltic pump. Under flow conditions of 10 mL/min and ~1 cm/s, both a control PTFE and SLIPS surface were exposed in parallel to PA14 bacterial culture for 24 hour, 48 hour, and 7-day (168 hour) periods. Photographs of the two substrates following 48 hour growth show a yellowish, slimy control substrate and a visually uncontaminated SLIPS (FIG. 37A-B).

When tilted, biofilm slime spread on the control substrate but slid off the SLIPS. The attached biofilm was also stained by crystal violet for both visual inspection and quantitative biomass comparison by optical density. This macroscopic assay showed a dramatic difference between the substrates, as shown in (FIG. 37A-B). Indeed, crystal violet absorbance, proportional to the attached biomass, showed a 99.6% average reduction in biofilm on SLIPS as compared to control PTFE following the 7-day bacterial growth (FIG. 37C). By comparison, PEGylated titanium surfaces have been reported to reduce biofilm attachment by 86% after 5 hours of growth. The 48 hour growth of P. aeruginosa on Ti-coated glass slides was found to differ by <19% from PTFE, indicating similar long-term biofilm attachment on these two controls and thus a similar starting point for attachment reduction. Even if PEG desorption is assumed to not occur due to recent advances in multi-tether attachment, and even if no chemical masking occurred after 7 days submerged in bacterial culture, the 14% of remaining biofilm would be ~35 times more than on the SLIPS substrate.

It is worth noting that the flow velocity in this experiment of ~1 cm/s is a conservatively gentle condition. In other environments where biofilms form, e.g., a ½-inch building water pipe or a ship hull at 20 knot cruise speed, typical flow velocities can be on the order of 1 m/s and 10 m/s respectively, with proportionately higher shear forces that would support biofilm removal from a SLIPS substrate. In biological and biomedical systems such as indwelling catheters, urinary tracts, and the human vascular system, flow velocities are also frequently more aggressive, on the order of 10-100 cm/s.

Figure 38:
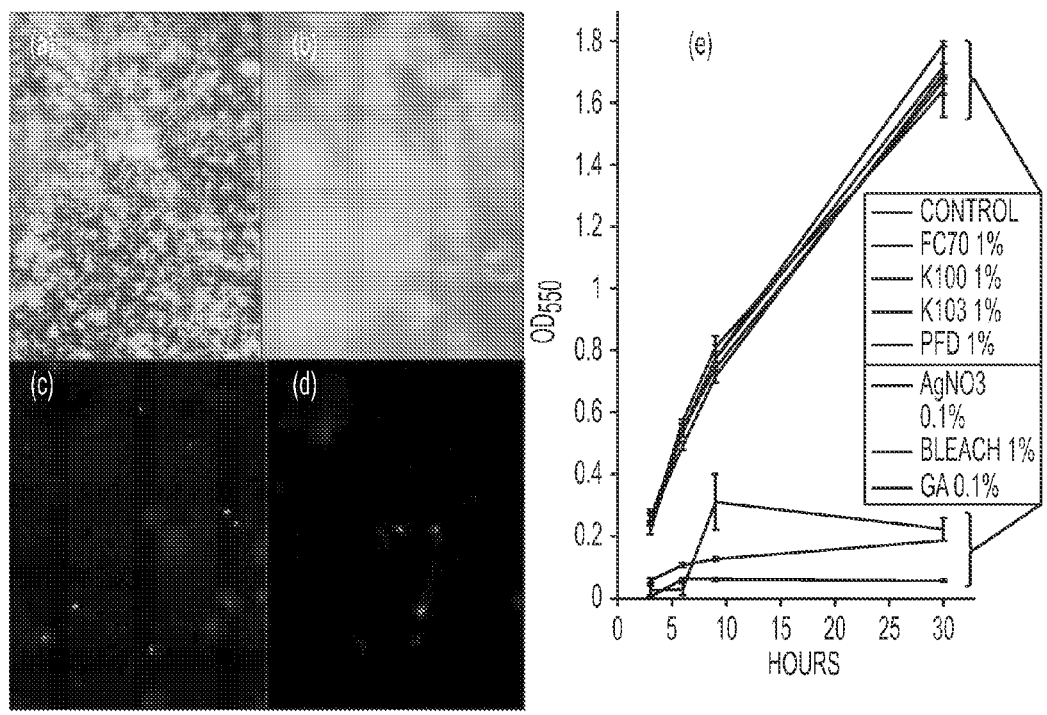
FIG. 38 shows images of a microscale view of *P. aeruginosa* biofilm attachment on SLIPS and control PTFE surfaces after 24 and 7-day growths in 10 mL/min flow. (A-B). Growth on the PTFE surface appeared dense, three-dimensional, and uniform (A-B), whereas on the SLIPS, only sparse, isolated single cells or microcolonies were observed (C-D). Referring to the graph, (E), these cells appeared to be unattached or poorly attached, i.e., drifting with convective currents in the fluid, further supporting that a liquid surface provides very low adhesion to the individual bacteria or micro-colonies.

To characterize biofilm attachment to PTFE and SLIPS substrates on the microscale, multiple sample areas following 24 hour, 48 hour, and 7-day flow condition growths were fluorescently imaged. The results were analogous to those achieved in the initial static growth experiment. Biofilm on the control surface appeared characteristically dense, three-dimensional, and uniform (FIG. 38A-B). On the SLIPS, only sparse, isolated single cells or microcolonies were observed (FIG. 38C-D), and these appeared to be unattached, i.e., drifting with convective currents in the ambient fluid. This observation further supports that a liquid surface provides very low adhesion to the individual bacteria or microcolonies. The average fluorescence intensities of 20 representative fields of view per substrate were computed as numeric pixel averages [(R+G+B)/3]. While not fully capturing intensity from out-of-focus biofilm structure on the control surface, the control values may be considered a lower bound; thus there is at least a 98% average intensity reduction in the fluorescence signal from PTFE to SLIPS, similar to the global quantification by crystal violet.

To confirm that the dramatic biofilm attachment inhibition on SLIPS substrates was not a result of cytotoxicity of the SLIPS liquids, four of the liquids were screened for effects on bacterial growth. These included the Krytox 103 used for SLIPS fabrication in this study, as well as FC70, Krytox 100, and perfluorodecalin (traditionally used as a blood-substitute). The growth curves of P. aeruginosa were measured following growth in shaken TB cultures—thereby assuring uniform exposure—with 1% and 0.1% concentrations of each SLIPS liquid. As seen in FIG. 38E, optical densities showed statistically indistinguishable bacterial growth at 3, 6, 9, and 30 hours for all tested SLIPS liquids and concentrations as compared to the control culture. Equivalent concentrations of three negative controls—silver nitrate (a common antiseptic compound and representative of silver impregnated surfaces), bleach, and glutaraldehyde (commonly used for clinical tool sterilization)—were also tested. As expected, all three exhibited massive toxicity within these timeframes, in contrast to the null effect of the SLIPS liquids.

Figure 39:
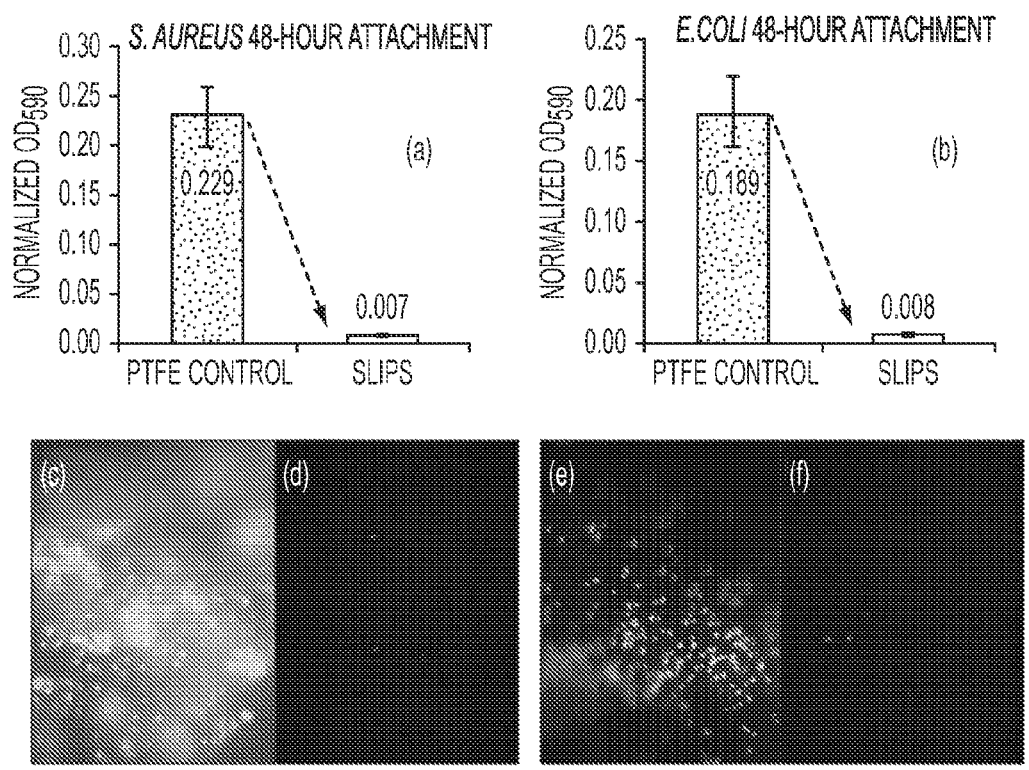
FIG. 39 shows images and graphs that demonstrate that biofilm attachment reduction by SLIPS is species independent. The attachment of *Staphylococcus aureus* (A) and *Escherichia coli* (B), was reduced by 97.2% and 96%, respectively, versus PTFE following 48 hour growth under identical flow conditions to *P. aeruginosa*. While neither of these species formed as robust biofilms as does, their final attachment to SLIPS was comparably minimal (C-F). Visualized by fluorescence, dense uniform biofilm coverage and sparse, isolated cells respectively attached to the control and SLIPS substrates.
Figure 40:
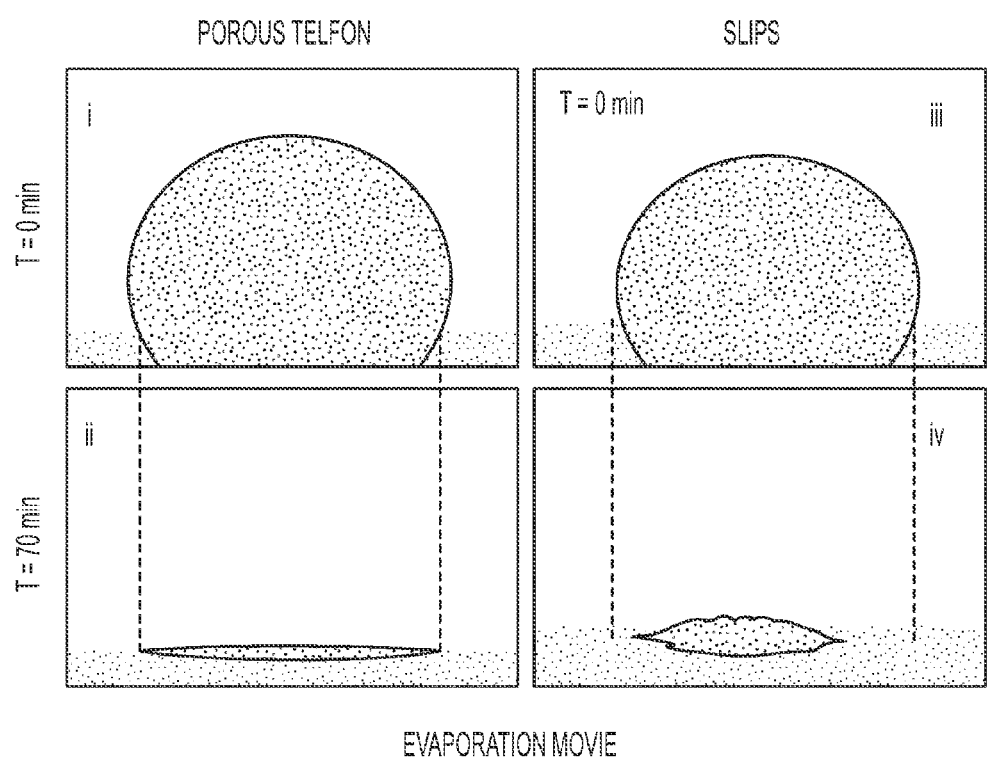
FIG. 40 is a set of images from a split-frame movie showing evaporation dynamics of *P. aeruginosa* culture droplets on a superhydrophobic PTFE porous surface (i-ii) and a PTFE SLIPS surface infused with Krytox 103 (iii-iv). The pinning characteristics as well as the stains remaining on the surfaces upon drying indicated the level of adhesion between the bacterial droplet and the substrate. In the absence of contact line pinning, the droplet follows a nearly constant contact angle mode of evaporation without the formation of a coffee ring stain (iv). The absence of the coffee ring formation also indicated that the adhesion of the bacteria on the SLIPS was small compared to the forces imparted by the meniscus of the droplet.
Figure 41:
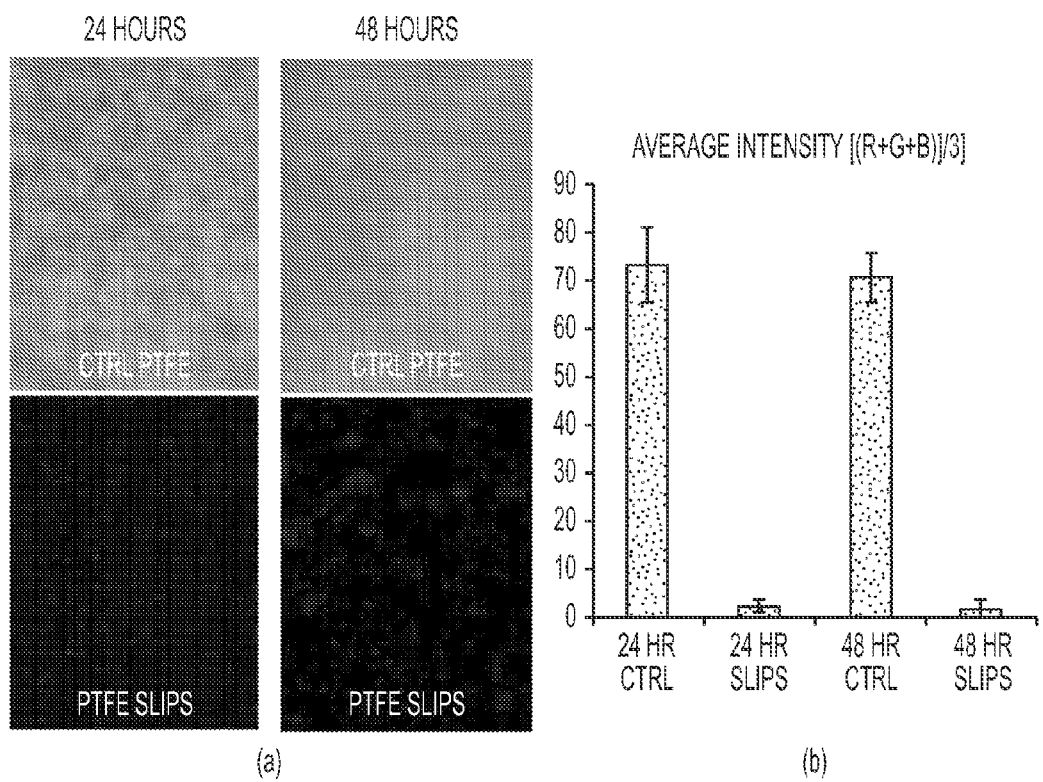
FIG. 41 shows images of a microview of *P. aeruginosa* biofilm attachment on SLIPS and control PTFE surfaces after 24 and 48 hr growths in 10 mL/min flow. (a) Fluorescence average intensities (b) average intensity graph showing a 97-98% average intensity reduction, analogous to the crystal violet global measurement.

The attachment of two other clinically important, pathogenic, biofilm-forming species, *Staphylococcus aureus* (SC01) and *Escherichia coli* (ZK2686) was studied for 48 hours under identical flow conditions. SLIPS performance comparable to that of *Pseudomonas aeruginosa* was observed. As shown in FIG. 39A-B, *S. aureus* attachment was reduced by 97.2% and *E. coli* by 96% versus PTFE. While neither of these species formed as robust biofilms as did *P. aeruginosa*, their final attachment to SLIPS was similarly low based on crystal violet absorbance. Visualized by fluorescence in FIG. 39D-F, dense uniform coverage and sparse, isolated cells respectively attached to the control surface and SLIPS. This indicated that SLIPS's anti-biofilm function was nonspecific and spanned phylogenetically diverse pathogenic bacteria.

Thus, it is apparent that the bacteria were presented with a smooth liquid "surface," and as such, were unable to anchor to the surface via pili and other cellular mechanisms as would be possible on a solid surface. The SLIPS lubricating liquid was also immiscible with the aqueous bacterial medium (Liquid A), and the surface tension at the interface (on the order of 50 mN/m) was likely difficult for bacteria to penetrate, even with bacterial surfactant production. Indeed, bacteria embedding within the SLIPS was not observe, which indicates that bacteria could not swim through the interface. Without access to the solid material beneath the lubricating liquid, bacteria were unable to attach, and remained subject to ambient flow and thus subject to passive removal.

Example 8

Figure 30:
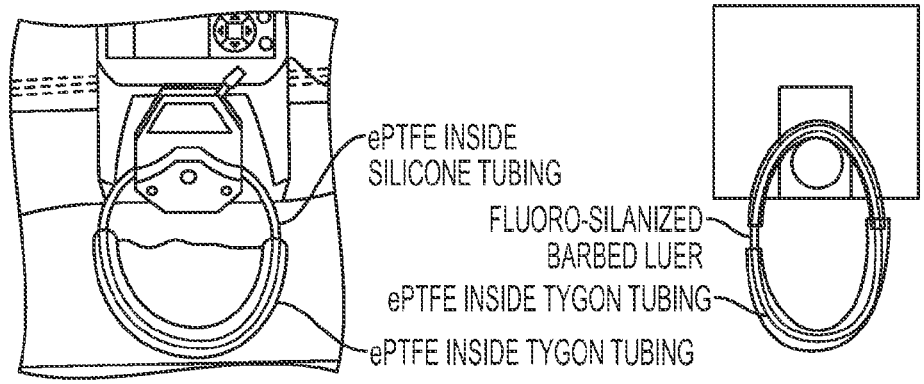
FIG. 30 shows images of non-anticoagulated whole human blood (diluted 1:1 with saline) flowing at 3,000 mL/hr using peristaltic pumping through SLIPS tubing for 20 min without producing clotting including the experimental setup (A) and results which showed no signs of clotting in the tubing (B).
Figure 30B:
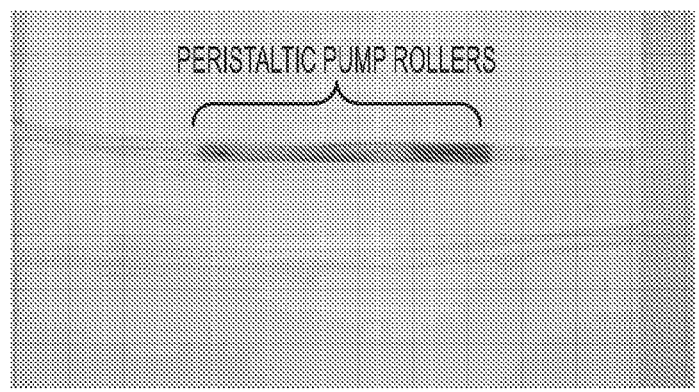
Figure 31:
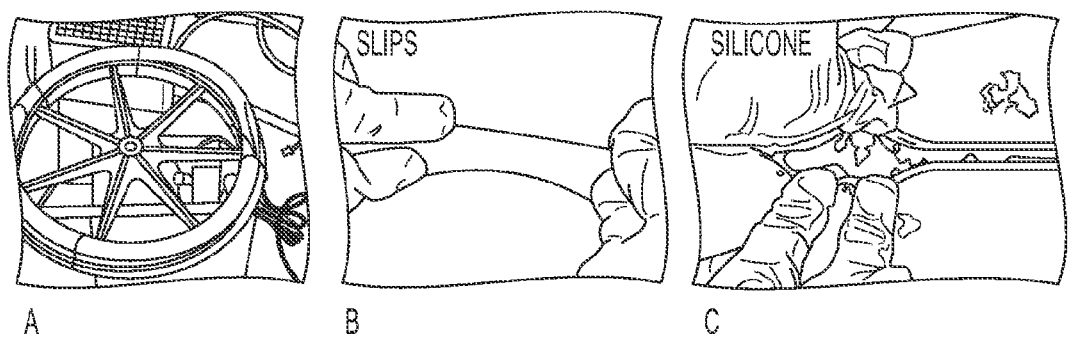
FIG. 31A-C shows images of the tubing of FIG. 33 after 20 minutes of 12 mL of fresh human blood free of anticoagulant was pumped through SLIPS tubing. The blood did not clot in the tubing.
Figure 32:
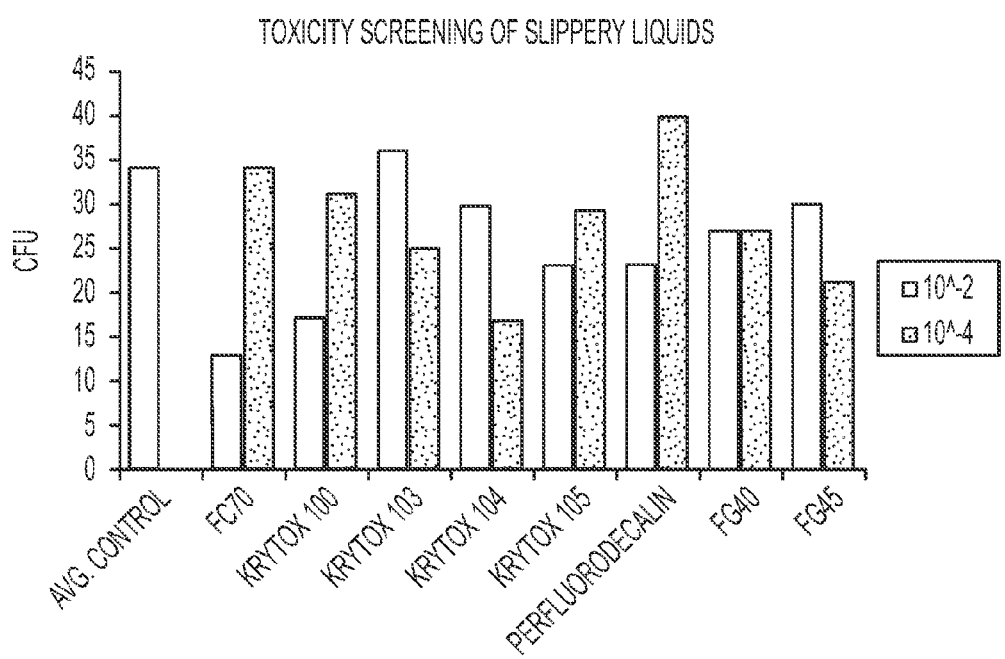
FIG. 32 is a graph showing the dependence of liquid repellency of SLIPS on the viscosity of Liquid B (here, Krytox 100, 103, and 105 (DuPont)). For constant viscosity of Liquid A (here, 25 µL of glycerol), Liquid A's mobility increases as the viscosity of Liquid A decreases. Likewise, for constant viscosity of Liquid B, the mobility of Liquid A increases with reducing viscosity. Thus viscous dissipation plays a major role in the liquid mobility on SLIPS.

SLIPS can be used to coat medical devices, including tubing, to prevent, reduce, or delay blood clot formation and cell adhesion. FIG. 31A shows the experimental setup in included a 24" loop of SLIPS tubing (ePTFE+FC70) and a 24" loop of standard silicone tubing (0.250"ID) as a control. The preformed ePTFE tube was saturated with PFC FC70 oil, and encased in a silicone tube to help prevent oil loss and evaporation. Both the ePTFE SLIPS tube and the silicone tube control were filled with 12 mL of the diluted blood. A 24" preformed ePTFE tube was saturated with PFC FC-70, and encased in a silicone tube where it interfaced with a peristaltic pump and Tygon tubing in other regions to create an FC-70 reservoir. Fresh whole human blood (12 mL, diluted 1:1 with saline) free of anticoagulant was pumped through both sets of tubing at 3,000 mL/hr. After 20 minutes, there was no sign of clotting within the entire length of tubing (FIG. 30 and FIG. 31B). There was some staining (surface adsorption) in the region of the peristaltic pump roller contact (FIG. 30B), suggesting potential mechanical damage and infiltration of blood into the ePTFE at this site. After 30 min of flow there was no sign of clotting and minimal surface adhesion within the entire length of SLIPS tubing (FIG. 31C). In the silicone tubing there were signs of clotting and significant surface adhesion within the tube.

As will be apparent to one of ordinary skill in the art from a reading of this disclosure, aspects of the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

What is claimed is:

1. A method of preventing, reducing, or delaying adhesion, adsorption, surface-mediated clot formation, or coagulation of a biological material onto a device in contact therewith, comprising:
    providing the device comprising a substrate comprising a roughened surface, wherein the roughened surface comprises one or more functional groups chemically attached to the roughened surface, wherein the roughened surface has a roughness factor, R, greater than or equal to 1, where the roughness factor is defined as the ratio between the real surface area and the projected surface area; and a lubricating liquid wetting and adhering to the roughened surface to form a stabilized liquid overlayer, wherein the lubricating liquid covers the roughened surface, and wherein the one or more functional groups attached to the roughened surface and the lubricating liquid have an affinity for each other and the roughness factor is selected such that the lubricating liquid is immobilized in, on and over the functionalized roughened surface; and
    contacting the biological material to the device so that the stabilized liquid overlayer prevents, reduces, or delays adhesion, adsorption, surface-mediated clot formation or coagulation of the biological material onto the device.

2. The method of claim 1, wherein the device is selected from the group consisting of a cannula, connector, catheter, needle, capillary tube, tubing, syringe and combinations thereof.

3. The method of claim 1, wherein the device is selected from the group consisting of a slide, plate, film, work surface, well, well plate, Petri dish, tile, jar, flask, beaker, vial, test tube, column, container, cuvette, bottle, drum, vat, tank, and combinations thereof.

4. The method of claim 1, wherein the device is selected from the group consisting of an organ, artificial organ, implant, stent and combinations thereof.

5. The method of claim 1, wherein the substrate is roughened using photolithography, projection lithography, e-beam writing or lithography, depositing nanowire arrays, growing nanostructures on the surface of a substrate, soft lithography, replica molding, solution deposition, solution polymerization, electropolymerization, electrospinning, electroplating, vapor deposition, layered deposition, rotary jet spinning of polymer nanofibers, contact printing, etching, transfer patterning, microimprinting, self-assembly, boehmite (γ-AlO(OH)) formation, spray coated, and combinations thereof.

6. The method of claim 1, wherein the substrate comprises polymers, metals, sapphire, glass, diamond, graphite, black carbon, or ceramics.

7. The method of claim 1, wherein the biological material comprises a simple aqueous fluid, a complex aqueous fluid, a solidified fluid, whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, or combinations thereof.

8. The method of claim 1, wherein the biological material is a natural or synthetic solution used in medicines, intravenous solutions, pharmaceutical manufacturing, or medication delivery systems.

9. The method of claim 1, wherein the substrate comprises one or more of polydimethylsiloxane, polypropylene, polytetrafluoroethylene, fluoro-silanized metals, fluoro-silanized natural polymers, fluoro-silanized synthetic polymers, polytetrafluoroethylene (PTFE), polyvinylfluoride, polyvinylidene fluoride, and fluorinated ethylene propylene.

10. The method of claim 1, wherein the lubricating liquid has a density greater than the density of the biological material.

11. The method of claim 1, wherein the lubricating liquid comprises a fluid selected from the group consisting of tertiary perfluoroalkylamines, perfluorotri-n-butylamine, perfluoroalkylsulfides, perfluoroalkylsulfoxides, perfluoroalkylethers, perfluorocycloethers, perfluoropolyethers, perfluoroalkylphosphines, and perfluoroalkylphosphineoxides, and combinations thereof.

12. The method of claim 1, wherein the method prevents, reduces, or delays bacterial contamination or biofilm formation onto the device.

13. The method of claim 1, wherein the biological material comprises blood and the stabilized liquid overlayer prevents coagulation of blood onto the device.

14. The method of claim 1, wherein the device is selected from the group consisting of a clamp, skin hook, cuff, retractor, shunt, needle, capillary tube, tubing, and combinations thereof.

15. The method of claim 1, wherein the device is selected from the group consisting of an endotracheal tube, ventilator, associated ventilator tubing, drug delivery vehicle, intrauterine device, syringe, endoscope, and combinations thereof.

16. The method of claim 1, wherein the device is selected from a biosensor, an optical window, endoscope, colonoscope or combinations thereof.

17. The method of claim 1, wherein the device is a wound dressing.

18. The method of claim 1, wherein the substrate is a roughened surface comprising a porous material.

19. The method of claim 1, wherein the lubricating liquid infiltrates the substrate by capillary action.

20. The method of claim 1, wherein the lubricating liquid is capable of self-healing by wicking back to any damaged region of the substrate after physical damage.

21. The method of claim 1, wherein the substrate is silanized.

22. The method of claim 1, wherein the lubricating liquid comprises a perfluorinated liquid, liquid silicone elastomers, vegetable or mineral oil, liquid hydrocarbons, or combinations thereof.

23. The method of claim 1, wherein the biological material comprises a simple aqueous fluid, a complex aqueous fluid, a solidified fluid, whole blood, plasma, serum, sweat, feces, urine, saliva, tears, vaginal fluid, prostatic fluid, gingival fluid, amniotic fluid, intraocular fluid, cerebrospinal fluid, seminal fluid, sputum, ascites fluid, pus, nasopharengal fluid, wound exudate fluid, aqueous humour, vitreous humour, bile, cerumen, endolymph, perilymph, gastric juice, mucus, peritoneal fluid, pleural fluid, sebum, vomit, or combinations thereof.

24. The method of claim 1, wherein the biological material is a solution or suspension containing particles selected from the group consisting of normal cells, diseased cells, parasitized cells, cancer cells, foreign cells, stem cells, and infected cells, microorganisms, viruses, virus-like particles, bacteria, bacteriophages, proteins, cellular components, cell organelles, cell fragments, cell membranes, cell membrane fragments, viruses, virus-like particles, bacteriophage, cytosolic proteins, secreted proteins, signaling molecules, embedded proteins, nucleic acid/protein complexes, nucleic acid precipitants, chromosomes, nuclei, mitochondria, chloroplasts, flagella, biominerals, protein complexes, and minicells.

25. The method of claim 1, wherein said contacting the biological material to the device is carried out without forcing the biological material against the device by an opposing device.

26. The method of claim 2, wherein the device is a catheter.

27. The method of claim 2, wherein the device is a tubing.

* * * * *